(12) United States Patent
Masat et al.

(10) Patent No.: US 7,531,166 B2
(45) Date of Patent: May 12, 2009

(54) IL-1β BINDING ANTIBODIES AND FRAGMENTS THEREOF

(75) Inventors: Linda Masat, Oakland, CA (US); Mary Haak-Frendscho, Newark, CA (US); Gang Chen, San Diego, CA (US); Arnold Horwitz, San Leandro, CA (US); Marina Roell, Concord, CA (US)

(73) Assignee: XOMA Technology, Ltd., Berkely, CA (US)

( * ) Notice: Subject to any disclaimer, the term of this patent is extended or adjusted under 35 U.S.C. 154(b) by 253 days.

(21) Appl. No.: 11/472,813

(22) Filed: Jun. 21, 2006

(65) Prior Publication Data

US 2008/0044414 A1    Feb. 21, 2008

Related U.S. Application Data

(60) Provisional application No. 60/692,830, filed on Jun. 21, 2005.

(51) Int. Cl.
C07K 16/24 (2006.01)
A61K 39/395 (2006.01)

(52) U.S. Cl. ................. 424/85.2; 530/387.1; 530/388.1

(58) Field of Classification Search .................... None
See application file for complete search history.

(56) References Cited

U.S. PATENT DOCUMENTS

| | | | |
|---|---|---|---|
| 4,762,914 | A | 8/1988 | Auron et al. |
| 4,766,069 | A | 8/1988 | Auron et al. |
| 4,772,685 | A | 9/1988 | Schmidt et al. |
| 4,935,343 | A | 6/1990 | Allison et al. |
| 5,001,057 | A | 3/1991 | Auron et al. |
| 5,077,219 | A | 12/1991 | Auron et al. |
| 5,122,459 | A | 6/1992 | Conlon et al. |
| 5,286,847 | A | 2/1994 | Gehrke et al. |
| 5,348,858 | A | 9/1994 | Uetsuki et al. |
| 5,474,899 | A | 12/1995 | Lisi |
| 5,484,887 | A | 1/1996 | Kronheim et al. |
| 5,510,462 | A | 4/1996 | Auron et al. |
| 5,658,570 | A | 8/1997 | Newman et al. |
| 5,681,933 | A | 10/1997 | Auron et al. |
| 5,766,886 | A | 6/1998 | Studnicka et al. |
| 5,789,185 | A | 8/1998 | Lisi |
| 5,869,619 | A | 2/1999 | Studnicka |
| 5,885,793 | A | 3/1999 | Griffiths |
| 5,959,085 | A | 9/1999 | Garrone et al. |
| 6,899,878 | B2 | 5/2005 | Graham et al. |
| 2003/0022869 | A1 | 1/2003 | Wiemer et al. |
| 2003/0026806 | A1 | 2/2003 | Witte et al. |
| 2003/0124617 | A1 | 7/2003 | Gram et al. |
| 2003/0166069 | A1 | 9/2003 | Amgen |
| 2004/0023869 | A1 | 2/2004 | Sims et al. |
| 2004/0063913 | A1 | 4/2004 | Gram et al. |
| 2005/0084493 | A1 | 4/2005 | Witte |
| 2005/0152850 | A1 | 7/2005 | Engebretson |
| 2005/0186615 | A1 | 8/2005 | Lin et al. |
| 2005/0256197 | A1 | 11/2005 | Engebretson |
| 2006/0094663 | A1 | 5/2006 | Chemtob |

FOREIGN PATENT DOCUMENTS

| | | |
|---|---|---|
| EP | 0267611 B1 | 5/1993 |
| EP | 0 161 901 | 12/1993 |
| EP | 0364778 B1 | 3/1996 |
| EP | 0 569 687 | 8/2002 |
| WO | WO 95/01997 | 1/1995 |
| WO | 02/16436 A2 | 2/2002 |
| WO | WO 02/16436 A1 | 2/2002 |
| WO | WO 03/010282 | 2/2003 |
| WO | WO 03/010282 A1 | 2/2003 |
| WO | WO 03/034984 | 5/2003 |
| WO | WO 03/073982 | 9/2003 |
| WO | 2004/002512 A1 | 1/2004 |
| WO | 2004022718 A2 | 3/2004 |
| WO | WO 2004/067568 | 8/2004 |
| WO | WO 2004/067568 A1 | 8/2004 |
| WO | WO 2004/072116 | 8/2004 |
| WO | 2005019259 A2 | 3/2005 |
| WO | 2005084696 A1 | 9/2005 |
| WO | WO 2006/081139 | 8/2006 |
| WO | 2007002261 A2 | 1/2007 |

OTHER PUBLICATIONS

Mikayama et al. Proc. Natl. Acad. Sci. USA vol. 90, pp. 10056-10060.*

Voet et al. Biochemistry John Wiley & Sons, Inc., pp. 126-128 and 228-234.*

(Continued)

Primary Examiner—Prema Mertz
(74) Attorney, Agent, or Firm—John Polo; K&L Gates LLP

(57) ABSTRACT

An IL-1β binding antibody or IL-1β binding fragment thereof comprising the amino acid sequence of SEQ ID NO: 2, and related nucleic acids, vectors, cells, and compositions, as well as method of using same to treat or prevent a disease, and a method of preparing an affinity matured IL-1β binding polypeptide. IL-1β binding antibodies or IL-1β binding fragments thereof are provided which have desirable affinity and potency.

10 Claims, 15 Drawing Sheets

OTHER PUBLICATIONS

Mikayama et al. Proc. Natl. Acad. Sci. USA vol. 90, pp. 10056-10060, 1993.*

Voet et al. Biochemistry John Wiley & Sons, Inc., pp. 126-128 and 228-234, 1990.*

Bloomgarden, "Concepts of Insulin Resistance", Metabolic Syndrome and Related Disorders, 3(4):284-293 (2005).

Johnson, et al, "Inhibition of vagally mediated immune-to-brain signalling by vanadyl sulfate speeds recovery from sickness", PNAS 102: 15184-89 (2005).

Scheen et al., "Internal carotid artery occlusion detected with nonmydriatic fundus photography: a case report" Diabetes Care, 22(9):1568-1577 (1999).

Maedler et al, "Glucose-induced B cell production of IL-1B contributes to glucose toxicity in human pancreatic islets", J Clin Invest 110:851-860 (2002).

Donath et al, "Inflammatory mediators and islet Bcell failure; a link between type 1 and type 2 diabetes", J Mol Med 81:455-470 (2003).

Larsen et al, "Interleukin-1-receptor antagonist in type 2 diabetes mellitus", New England Journal of Medicine 356:1517-1526 (2007).

Maybee, et al "Is anti-inflammatory therapy for type-2 diabetes mellitus ready for routine clinical practice?", Nature Clinical Practice, 3(12): 806-7 (2007).

Trayhurn et al., "Adipokines: inflammation and the pleiotropic role of white adipose tissue" Br. J. Nutr. 92:347-355, 2004.

Wisse, "The inflammatory syndrome: the role of adipose tissue cytokines in metabolic disorders linked to obesity", J. Am. Soc. Nephrol. 15:2792-2800, 2004.

Fantuzzi, "Adipose tissue, adipokines, and inflammation", J. Allergy Clin. Immunol. 115:911-919 (2005).

Matsuzawa, "The metabolic syndrome and adipocytokines", FEBS Lett. 580:2917-2921 (2006).

Greenberg et al., "Identifying the links between obesity, insulin resistance and beta-cell function: potential role of adipocyte-derived cytokines in the pathogenesis of type 2 diabetes", Eur J. Clin. Invest. 32 Suppl.3:24-34 (2002).

Jager, et al., "Interleukin-1Beta-Induced Insulin Resistance in Adipocytes Through Down-Regulation of Insulin Receptor Substrate-1 Expression", Endocrinology 148:241-251 (2007).

Kern et al., "Adiponectin expression from human adipose tissue: relation to obesity, insulin resistance, and tumor necrosis factor-alpha expression", Diabetes 52:1779-1785 (2003).

Alheim, et al., Hyperresponsive febrile reactions to interleukin (IL) 1alpha and IL-1beta, and altered brain cytokine mRNA and serum cytokine levels in IL 1 beta deficient mice. Proc. Natl. Acad. Sci. 94:2681-686 (1997).

Kaizer, et al., "Gene Expression in Peripheral Blood Mononuclear Cells From Children With Diabetes", J Clin Endocrin Metab. 92(9):3705-3711 (2007).

O'Connor, et al., "IL-1Beta-Mediated Innate Immunity is Amplified in the db/db Mouse Model of Type 2 Diabetes", Journal of Immunology 174:4991-4997 (2005).

Studnicka et al. "Human-engineered monoclonal antibodies retain full specific binding activity by preserving non-CDR complementarity-modulating residues", Protein Engineering, 7: 805-814 (1994).

Yanofsky et al., "High affinity type I interleukin 1 receptor antagonists discovered by screening recombinant peptide libraries", Proc. Natl. Acad. Sci. USA 93:7381-7386 (1996).

Vigers et al., "X-ray crystal structure of a small antagonist peptide bound to interleukin-1 receptor type 1", J. Biol. Chem. 275:36927-36933 (2000).

Mellgren et al., "The renal subcapsular site offers better growth conditions for transplanted mouse pancreatic islet cells than the liver or spleen", Diabetologia 29:670-2 (1986).

Nicoletti, et al., "Protection from experimental autoimmune diabetes in the non-obese diabetic mouse with soluble interleukin-1 receptor", Eur J Immunol 24:1843-7 (1994).

Ruggiero et al., "Inhibitory activity of IL-1 receptor antagonist depends on the balance between binding capacity for IL-1 receptor type I and IL-1 receptor type II", J. Immunol. 158:3881-3887 (1997).

Guo et al., "Fluorescence resonance energy transfer reveals interleukin (IL)-1-dependent aggregation of IL-1 type I receptors that correlates with receptor activation", J. Biol. Chem. 270:27562-27568 (1995).

Svenson et al., "Differential binding of human interleukin-1 (IL-1) receptor antagonist to natural and recombinant soluble and cellular IL-1 type I receptors.", Eur. J. Immunol. 25:2842-2850 (1995).

Sandberg, et al., "IL-1 receptor antagonist inhibits recurrence of disease after syngeneic pancreatic islet transplantation to spontaneously diabetic non-obese diabetic (NOD) mice", Clin Exp Immunol 108:314-7 (1997).

Nathan, Thiazolidinediones for initial treatment of type 2 diabetes?, N. Engl. J. Med. 355:2477-2480 (2006).

Kahn, et al., "Glycemic Durability of Rosiglitazone, Metformin, or Glyburide Monotherapy", N. Engl. J. Med. 355 (23):2427-2443 (2006).

Donath, et al., "Mechanisms of B-Cell Death in Type 2 Diabetes", Diabetes, 54(2):108-113 (2005).

Donath, et al., "Decreased beta-cell mass in diabetes: significance, mechanisms and therapeutic implications", Diabetologia, 47:581-589 (2004).

Feingold, et al., "Effect of Interleukin-1 on Lipid Metabolism in the Rat. Similarities to and differences from tumor necrosis factor", Arteriosclerosis and Thrombosis and Vascular Biology, Am Heart Assoc., 11(3):495-500 (1991).

Maedler et al., "Leptin modulates beta cell expression of IL-1 receptor antagonist and release of IL-1beta in human islets", Proc. Natl. Acad. Sci. USA 101:8138-8143 (2004).

Donath et al., "Hyperglycemia-induced beta-cell apoptosis in pancreatic islets of Psammomys obesus during development of diabetes", Diabetes 48:738-744 (1999).

Reddy et al., "Immunoexpression of interleukin-1beta in pancreatic islets of NOD mice during cyclophosphamide-accelerated diabetes: co-localization in macrophages and endocrine cells and its attenuation with oral nicotinamide" Histochem J. 33:317-32, (2001).

Cailleau et al., "Treatment with neutralizing antibodies specific for IL-1beta prevents cyclophosphamide-induced diabetes in nonobese diabetic mice" Diabetes 46:937-940 (1997).

Reddy et al., "Immunoexpression of interleukin-1beta in pancreatic islets of NOD mice during cyclophosphamide-accelerated diabetes: co-localization in macrophages and endocrine cells and its attenuation with oral nicotinamide", Histochem J., 34:1-12 (2002).

Harada et al., "Promotion of spontaneous diabetes in non-obese diabetes-prone mice by cyclophosphamide" Diabetologia 27:604-606 (1984).

Dinarello, "Biologic basis for interleukin-1 in disease", Blood, J Amer Soc Hematology, 87(6):2095-147 (1996).

Khovidhunkit, et al., "Effects of infection and inflammation on lipo and lipoprotein metabolism; mechanisms and consequences to the host", J Lipid Research, 45:1169-96 (2004).

Thomas, et al., "Il-1 Receptor Deficiency Slows Progression to Diabetes in the NOD Mouse", Diabetes, 53: 113-121 (2004).

Tilg, et al., "Adipocytokines; mediators linking adipose tissue, inflammation and immunity" Nature Rev Immun, 6:772-83 (2006).

Dinarello, C.A., "IL-1beta", in Cytokine Reference: A compendium of cytokines and other mediators of host defense, Academic Press, p. 351-374 (2001).

Faggioni, et al., "IL-1 mediates leptin induction during inflammation" American Journal of Physiology-Regulatory 274:204-08 (1998).

Fantuzzi, et al., "Response to local inflammation of IL-1beta converting enzyme-deficient mice" J Immunology 158:1818-824 (1997).

Fantuzzi, et al. "Physiological and cytokine responses in interleukin-1beta deficient mice after zymosan-induced inflammation". American Journal of Physiology (1997).

Fantuzzi, et al., "Effect of endotoxin in IL-1beta deficient mice" Journal of Immunology 157:291-96 (1996).

Grundy, S.M., "Metabolic syndrome: connecting and reconciling cardiovascular and diabetes worlds", J. Am. Coll. Cardiol. 47:1093-1000 (2006).

Hoffman, et al., "Prevention of cold-associated acute inflammation in familial cold autoinflammatory syndrome by interleukin-1 receptor antagonist" Lancet 364:1779-85 (2004).
Kozak, et al. "IL-6 and IL-1beta in fever: studies using cytokine-deficient (knockout) mice" Annals of the New York Academy of Sciences 856:33-47 (1998).
Lovell, et al., "Interleukin-1 blockade by anakinra improves clinical systems in patients with neonatal-onset multisystem inflammatory disease" Athritis and Rheumatism 52(4):1283-86 (2005).
Sakuraba, et al., Reduced beta-cell mass and expression of oxidative stress-related DNA damage in the islet of Japanese type II diabetic patients. Diabetologia 45:85-96 (2002).
Mayfield, Diagnosis and classification of diabetes mellitus: new criteria. Am Fam Physician 58:1355-62 (1998).
Kim, et al., Comparison of the 1997 and 2003 American Diabetes Association classification of impaired fasting glucose. Journal of the American College of Cardiology 48(2):293-97 (2006).
Butler, et al., Beta-cell deficit and increased beta-cell apoptosis in humans with type 2 diabetes. Diabetes 52:102-10 (2003).
Barzilay, et al., Cardiovascular disease in older adults with glucose disorders: comparison of American Diabetes Association criteria for diabetes mellitus with WHO criteria. Lancet 354:622-25 (1999).
Zheng, et al., Resistance to fever induction and impaired acute-phase response in interleukin-1beta deficient mice. Immunity 3:9-19 (1995).
Reznikov, et al., "Utilization of endoscopic inoculation in a mouse model of intrauterin infection-induced preterm birth: role of interleukin 1beta" Biology Reproduction 60:1231-238 (1999).
Perrier, et al., IL-1 Receptor antagonist in metabolic disease: Dr. Jekyll or Mr. Hyde?, FEBS Letters 580:6289-94 (2006).
Rydgren, et al., Complete protection against interleukin-1beta-induced functional suppression and cytokine-mediated cytotoxity in rat pancreatic islets in votro using an interleukin-1 cytokine trap. Diabetes, 55(5): 1407-12 (2006).
Vincent, et al., Inhibition of Caspase-1/Interleukin-1beta Signaling Prevents Degeneration of Retinal Capillaries in Diabetes and Gakactosemia. Diabetes, 56(1):224-30 (2007).
Akahoshi, et al., Recent advances in crystal-induced acute inflammation, Current Opinion in Rheumatology 19:146-150 (2007).
Eggebeen, Gout: An Update, Am. Family Physician 76(6): 801-8, 811-2 (2007).
Cronstein, et al., The Inflammatory Process of Gout and its Treatment, Arthrities Research & Therapy 8(Suppl 1): S3 (2006).
Dinarello, Therapeutic strategies to reduce IL-1 activity in treating local and systemic inflammation, Current Opinion in Pharmacology 4:378-385 (2004).
Economides, et al., Cytokine traps: multi-component, high affinity blockers of cytokine action, Nature Medicine 9 (1):47-52 (2003).
Emad, et al., The Diagnostic dilemma of undifferentiated inflammatory synovitis of the knee joint/joints: a comprehensive approach, APLAR Journal of Rheumatology 10:182-189 (2007).
Martinon, et al., Gout: New insights into an old disease, J. Clin. Invest. 116:2073-2075 (2006).
Martinon, et al., Gout associated uric-acid crystals activate the NALP3 inflammasome, Nature 440:237-241 (2006).
Petrilli and Martinon., The inflammasome, autoimflammatory diseases and gout, Joint Bone Spine 74:571-576 (2007).
McGonagle, et al., Management of treatment resistant inflammation of acute on chronic tophaceous gout with anakinra, Ann. Rheum. Dis. 66:1683-1684 (2007).
Pope and Tschopp, The Role of Interleukin-1 and the Inflammasome in Gout, Arthritis and Rheumatism 56 (10):3183-88 (2007).
Schlesinger, Management of Acute and Chronic Gouty Arthritis, Drugs 64(21): 2399-2416 (2004).
So, et al., A pilot study of IL-1 inhibition by anakinra in acute gout, Arthritis Research & Therapy 9:R28 (2007).
Bieber and Terkeltaub, On the Brink of Novel Therapeutic Options for an Ancient Disease, Arthritis & Rheumatism 50 (8):2400-2414 (2004).
Chen, et al., MyD88 dependent IL-1 receptor signalling is essential for gouty inflammation stimulated by monosodium urate crystals, J. Clin. Investig. 116(8): 2262-71 (2006).

Di Giovine, et al., Urate Crystals Stimulate Production of Tumor Necrosis Factor Alpha from Human Blood Monocytes and Synovial Cells, J. Clin. Invest. 87:1375-1381 (1991).
Di Giovine, et al., Interleukin 1 (IL-1) as a mediator of crystal arthritis, J. Immunology 138(10): 3213-3218 (1987).
Liu-Bryan, et al., Innate Immunity Conferred by Toll-like Receptors 2 and 4 and Myeloid Differentiation Factor 88 Expression is Pivotal to Monosodium Urate Monohydrate Crystal-induced Inflammation, Arthritis & Rheumatism 52 (9):2936-46 (2005).
Liu-Bryan, et al., TLR2 Signaling in Chondrocytes Drives Calcium Pyrophosphate Dihydrate and Monosodium Urate Crystal-Induced Nitric Oxide Generation, J. Immunology 174:5016-5023 (2005).
Nuki and Simkin, A concise history of gout and hyperuricmia and their treatment, Arthritis Research & Therapy 8(Suppl 1):S1 (2006).
Guerne, et al., Inflammatory microcrystals stimulate interleukin-6 production and secretion by human monocytes and synoviocytes. Arthritis and Rheumatism 32(11):1443-452 (1989).
Simkin PA, The pathogenesis of podagra. Annals of Internal Medicine 86:230-33 (1977).
Terkeltaub, et al., Monocyte-derived neutrophil chemotactic factor/interleukin-8 is a potential mediator of crystal-induced inflammation. Arthritis and Rheumatism 34(7):894-903 (1991).
Arend et al., Binding of IL-1α, IL-1β, and IL-1 receptor antagonist by soluble IL-1 receptors and levels of soluble IL-1 receptors in synovial fluids. J. Immunol. 153:4766-4774 (1994).
D'Ettorre et al., Functional epitope mapping of human interleukin-1β by surface plasmon resonance. Eur. Cytokine Netw. 8:161-171 (1997).
Boraschi et al., Differential inhibition of IL-1β activities and receptor binding of monoclonal antibodies mapping within a discrete region of the protein. Lymphokine Cytokine Res. 10:377-384 (1991).
Towbin et al., Neoepitope immunoassay: An assay for human interleukin 1β based on an antibody induced conformational change. J. Immunoassay 17:353-369 (1996).
Jackson et al., In vitro antibody maturation: Improvement of a high affinity, neutralizing antibody against IL-1β. J. Immunol. 154:3310-3319 (1995).
Kock et al., Characterization of a monoclonal antibody directed against the biologically active site of human interleukin 1. J. Exp. Med. 163:463-468 (1986).
Dinarello et al., The production of antibody against human leukocytic pyrogen. J. Clin. Invest. 60:465-472 (1977).
Dinarello et al., Human leukocytic pyrogen: purification and development of a radioimmunoassay. Proc. Natl. Acad. Sci. USA 74:4624-4627 (1977).
Lu et al., IL-1beta epitope mapping using site-directed mutagenesis and hydrogen-deuterium exchange mass spectrometry analysis. Biochemistry 44:11106-11114 (2005).
Garrone et al., Generation and characterization of a human monoclonal autoantibody that acts as a high affinity interleukin-1 alpha specific inhibitor. Mol. Immunol. 33:649-658 (1996).
McIntyre et al., Inhibition of interleukin 1 (IL-1) binding and bioactivity in vitro and modulation of acute inflammation in vivo by IL-1 receptor antagonist and anti-IL-1 receptor monoclonal antibody. J. Exp. Med. 173:931-939 (1991).
Gershenwald et al., Interleukin 1 receptor blockade attenuates the host inflammatory response. Proc. Natl. Acad. Sci. USA 87:4966-4970 (1990).
Haraoui et al., Biologic agents in the treatment of rheumatoid arthritis. Curr. Pharm. Biotechnol. 1:217-233 (2000).
Herzbeck et al., Functional and molecular characterization of a monoclonal antibody against the 165-186 peptide of human IL-1 beta. Scand. J. Immunol. 30:549-562 (1989).
Fredericks et al., Identification of potent human anti-IL-1RI antagonist antibodies. Protein Eng. Des. Sel. 17:95-106 (2004).
Boraschi et al., A monoclonal antibody to the IL-1 beta peptide 163-171 blocks adjuvanticity but not pyrogenicity of IL-1 beta in vivo. J. Immunol. 143:131-134 (1989). Erratum in: J. Immunol. 143:1403 (1989).
Chen et al., Effects of Interleukin-1alpha, interleukin-1 receptor antagonist, and neutralizing antibody on proinflammatory cytokine expression by human squamous cell carcinoma lines. Cancer Res. 58:3668-3676 (1998).

Evans et al., Mapping receptor binding sites in interleukin (IL)-1 receptor antagonist and IL-1 beta by site-directed mutagenesis. Identification of a single site in IL-1ra and two sites in IL-1 beta. J. Biol. Chem. 270:11477-11483 (1995).

Slack et al., Independent binding of interleukin-1 alpha and interleukin-1 beta to type I and type II interleukin-1 receptors. J. Biol. Chem. 268:2513-2524 (1993).

Vigers et al., Crystal structure of the type-I interleukin-1 receptor complexed with interleukin-1beta. Nature 386:190-194 (1997).

Dinarello, The many worlds of reducing interleukin-1. Arthritis Rheum. 52:1960-1967 (2005).

Pascual et al., Role of interleukin-1 (IL-1) in the pathogenesis of systemic onset juvenile idiopathic arthritis and clinical response to IL-1 blockade. J. Exp. Med. 201:1479-1486 (2005).

Kenney et al., Monoclonal antibodies to human recombinant interleukin 1 (IL 1)β: Quantitation of IL 1β and inhibition of biological activity. J. Immunol. 138:4236-4242 (1987).

Dinarello, Therapeutic strategies to reduce IL-1 activity in treating local and systemic inflammation. Curr. Opin. Pharmacol. 4:378-385 (2004).

Dinarello, Blocking IL-1 in systemic inflammation. J. Exp. Med. 201:1355-1359 (2005).

Smith et al., A single amino acid difference between human and monkey interleukin (IL)-1β dictates effective binding to soluble type II IL-1 receptor. J. Biol. Chem. 277:47619-47625 (2002).

Abramson et al., Blocking the effects of IL-1 in rheumatoid arthritis protects bone and cartilage. Rheumatology 41:972-980 (2002).

Dayer, The pivotal role of interleukin-1 in the clinical manifestations of rheumatoid arthritis. Rheumatology 42(Suppl.2):ii3-ii10 (2003).

Joosten et al., IL-1αβ blockade prevents cartilage and bone destruction in murine type II collagen-induced arthritis, whereas TNF-a blockade only ameliorates joint inflammation. J. Immunol. 163:5049-5055 (1999).

Yang et al., IL-1 receptor antagonist-mediated therapeutic effect in murine myasthenia gravis is associated with suppressed serum proinflammatory cytokines, C3 and anti-acetylcholine receptor IgG1. J. Immunol. 175:2018-2025 (2005).

Osnes, et al., Inhibition of IL-1 induced tissue factor (TF) synthesis and procoagulant activity (PCA) in purified human monocytes by IL-4, 1L-10 and IL-13. Cytokine 8, No. 11 [822-7] (1996).

Napoleone, et al., Monocytes Upregulate Endothelial Cell Expression of Tissue Factor: A Role for Cell-Cell Contact and Cross-Talk. Blood, 89, No. 2 [541-9] (1997).

Kuhns, et al., Ca2+-Dependent Production and Release of IL-3 in Human Neutrophils. J. Immuno. 161, No. 8 [4332-39] (1998).

Dezzutti, et al., Involvement of Matrix Metalloproteinases in Human Immunodeficiency Virus Type 1-Induced Replication by Clinical Mycobacterium avium Isolates. J. Infect. Dis. 180 [1142-52] (1999).

Grunstein, et al., Autocrine cytokine signaling mediates effects of rhinovirus on airway responsiveness. Am. J. Physiol Lung Cell Mol. Physiol. 278 [L1146-53] (2000).

Hedges, et al., Mitogen-Activated Protein Kinases Regulate Cytokine Gene Expression in Human Airway Myocytes. Am. J. Respir. Cell Mol. Bio. 23 [86-94] (2000).

Morisaki, et al., A combination of Cyclosporin-A (CsA) and InterferonGamma (INF-y) Induces Apoptosis in Human Gastric Carcinoma Cells. Anticancer Research 20 [3363-74] (2000).

Yates, et al., Amyloid β and Amylin Fibrils Induce Increases in Proinflammatory Cytokine and Chemokine Production by THP-1 Cells and Murine Microglia. J. Neurochem. 74 [1017-25] (2000).

Moldovan, et al., Diacerhein and rhein reduce the ICE-induced 1L-1β and IL-18 activation in human osteoarthritic cartilage. Osteoarthritis and Cartilage 8 [186-96] (2000).

Yoshiie, et al., Intracellular Infection by the Human Granulocytic Ehrlichiosis Agent Inhibits Human Neutrophil Apoptosis. Infection and Immunity 68, No. 3 [1125-33] (Mar. 2000).

Kawakami, et al., CD4+ T Cell Mediated Cytotoxicity Toward Thyrocytes: The Importance of Fas/Fas Ligand Interaction Inducing Apoptosis of Thyrocytes and the Inhibitory Effect of Thyroid-Stimulating Hormone. Lab. Invest. 80, No. 4 [471-84] (Apr. 2000).

Novak et al., Engagement of FceRI on Human Monocytes Induces the Production of IL-10 and Prevents Their Differentiation in Dendritic Cells. J. Immuno. 167, No. 2 [797-804] (2001).

Levesque, et al., Activated T Lymphocytes Regulate Hyaluronan Binding to Monocyte CD44 Via Production of IL-2 and IFN-y. J. Immuno. 166, No. 1 [188-96] (2001).

Sennikov, et al., Production of cytokines by immature erythroid cells derived from human embryonic liver. Eur. Cytokine Netw. 12, No. 2 [274-9] (2001).

Lin, et al., Pseudomonas aeruginosa Activates Human Mast Cells to Induce Neutrophil Transendothelial Migration Via Mast Cell-Derived IL-1α and β. J. Immuno. 169 [4522-30] (2002).

Li, et al., Expression of caspase-1 in synovial membrane-like interface tissue around loosened hip prostheses. Rhem. Int. 22 [97-102] (2002).

Rawlins, et al., Inhibition of endotoxin-induced TNF-α production in macrophages by 5Z 7-oxo-zeaenol and other fungal resorcyclic acid lactones. Int. J. Irnmunopharm. Acol. 21, No. 12 [712-814] (1999).

Gracie, et al., A proinflammatory role for IL-18 in rheumatoid arthritis. J. Clin, Invest. 104, No. 10 [1393-401] (1999).

Trindade, et al., Interleukin-4 Inhibits Granulocyte-Macrophage Colony-Stimulating Factor, Interleukin-6, and Tumor Necrosis Factor-Alpha Expression by Human Monocytes in Response to Polymethylethacrylate Particle Challenge in Vitro. J. Orthop. Res. 17, No. 6 [797-302] (1999).

Ledingham, et al., Nitric oxide donors stimulate prostaglandin F2α and inhibit thromboxane B2 production in the human cervix during the first trimester of pregnancy. Mol, Hum. Reprod. 5, No. 10 [973-82] (1999).

Gustafsson, et al., Cytokine, elastase and oxygen radical release by Fusobacterium nucleatum-activated leukocytes: a possible pathogenic factor in periodontitis. J. Clin, Periodontol. 27, No. 10 [756-62] (2000).

Marovich, et al., IL-12p70 Production by Leishmania major-Harboring Human Dendritic Cells Is a CD40/CD40 Ligand-Dependent Process. J. Immuno. 164, No. 11 [5658-65] (2000).

Christodoulides, et al., Interaction of primary human endometrial cells with Neisseria gonorrhoeae expressing green fluorescent protein. Mol. Microbiol 35, No. 1 [32-43] (2002).

Park, et al., TGF-β1 down-regulates inflammatory cytokine-induced VCAM-1 expression in cultured human glomerular-endothelial cells. Nephrol. Dial Transplant 15, No. 5 [596-604] (2000).

Hultin, et al., Microbiological findings and host response in patients with peri-implantitis. Clin. Oral Implants Res. 13 [349-56] (2002).

Brand, et al., Activation and Translocation of p38 Mitogen-Activated Protein Kinase After Stimulation of Monocytes With Contact Sensitizers. J. Invest. Dermatol. 119 [99-106] (2002).

Yoon, et al., Antibodies to Domains II and III of IL-1 Receptor Accessory Protein Inhibit IL-1β Activity But Not Binding: Regulation of IL-1 Responses is Via Type I Receptor, Not the Accessory Protein. J. Immuno. [3171-79] (1998).

Massone, et al., Mapping of Biologically Relevant Sites of Human IL-1β Using Monoclonal Antibodies. J. Immuno. 140, No. 11 [3812-3816] (1988).

Darling, et al., Kinetic Exclusion Assay Technology: Characterization of Molecular Interactions. Assay and Drug Dev. Tech., vol. 2, No. 6 [647-657] (2004).

Khilko, et al., Measuring Interactions of MHC Class I Molecules Using Surface Plasmon Resonance. J. Immum. Methods., 183 [77-94] (1995).

Faggioni, et al., ABX10-0031, a High Affinity Fully Human Anti-IL-1b Monoclonal Antibody for the Treatment of Inflammatory Diseases. Abstract for Presentation at 7th World Congress on Inflammation. Aug. 20-24, 2005 (Melbourne, Australia).

Arnett FC, Edworthy SM, Bloch, et al. The American Rheumatism Association 1987 revised criteria for the classification of rheumatoid arthritis. Arthritis and Rheumatism 1988;31:315-324.

Inoue K, Masuko-Hongo K., Okamoto M., Nishiota K., Efficacy of daily compared to intermittent administration of IL-1Ra for protection against bone and cartilage destruction in collagen-challenged mice. Clin Exp Rheumatol 2003:21(1):33-9.

Goupile P., et al., Safety and efficacy of intra-articular injection of IL-1ra (IL-1 receptor antagonist) in patients with painful osteoarthritis of the knee: a multicenter, double blind study. Arthritis and Rheumatism 2003;48(9).

Gruver D., Living With Rheumatoid Arthritis: Unmet Needs 2004.

Jacques, C., et al.. The role of IL-1 and IL-Ra in joint inflammation and cartilage degradation. Vitam Horm 2006;74:371-404.

Keystone EC and Strond V., Emerging Therapies in Rheumatoid Arthritis. In: Kelley's Textbook of Rheumatology. Harris E, Jr., M.D., Budd R, M.D., Genovese M, M.D., Firestein GS, M.D., Sargent J, M.D. and Sledge C, M.D., eds. Philadelphia, Elsevier Saunders. 2005:951-60 (chapter 62).

Joosten LA, et al., Anticytokine treatment of established type II collagen-induced arthritis in DBA/1 mice. A comparative study using anti-TNF alpha, anti-IL-1 alpha/beta, and IL-1Ra. Arthritis Rheum. 1996;39(5):797-809.

Lipsky PE, Rheumatoid arthritis. In: Harrison's principles of internal medicine. Wilson J, Braunwald E, Isselbacher K, et al., eds, McGraw-Hill, Inc. 1998: Ch 313: 1880-1888.

Lovell DJ, et al., Preliminary evidence for bioactivity of IL-1 trap (rilonacept), a long acting IL-1 inhibitor, in systemic juvenile idiopathic arthritis (sJIA). Arthritis and Rheumatism 2006;54(9).

Abbott RD, Gout and coronary heart disease: the Framingham Study. J Clin Epidemiol 1988;41:237-242.

Choi HK., et al., Purine-rich foods, dairy and protein intake, and the risk of gout in men. N Engl J Med 2004;2004 (350):1093-1103.

Geiger T, et al. Neutralization of interleukin-1 beta activity in vivo with a monoclonal antibody alleviates collagen-induced arthritis in DBA/1 mice and prevents the associated acute-phase response. Clin Exp Rheumatol. 1993;11 (5):515-22.

Hochberg MC., Racial differences in the incidence of gout. The role of hypertension. Arthritis and Rheumatism 1995;38:628-632.

Kim KY, A literature review of the epidemiology and treatment of acute gout. ClinTher 2003;25:1593-1616.

Klemp P., Gout is on the increase in New Zealand. Ann Rheum Dis 1997;56:22-26.

Martinon F, et al., Gout-associated uric acid crystals activate the nalp3 inflammasome. Nature 2006;440(9):237-41.

Nuki G and Simkin PA, A concise history of gout and hyperuricemia and their treatment. Arthritis Research and Therapy 2006;8(1):1-5.

Lichtman AH, et al., Role of interleukin 1 in the activation of T lymphocytes. PNAS. 1988;85:9699-9703.

Dinarello CA, Interleukin-1, inteleukin-1 receptors and interleukin-1 receptor antagonist. Intern Rev Immunol. 1998;16:457-499.

Hawkins, PN awkins PN, Lachmann HJ, Aganna E, McDermott MF. Spectrum of clinical features in muckle-wells syndrome and response to anakinra. Arthritis and Rheumatism. 2004;50:607-612.

Sutton C., et al., A crucial role for interleukin (IL)-1 in the induction of IL-17-producing T cells that mediate autoimmune encephalomyelitis. J Exp Med. 2006;203:1685-91.

Grutter, MG, et al., A mutational analysis of receptor binding sites of interleukin-1β:differences in binding of human interleukin-1β muteins to human and mouse receptors. Protein Eng. 1994;7:663-671.

Punzi L., et al., Pro-inflammatory interleukins in the synovial fluid of rheumatoid arthritis associated with joint hypermobility. Rheumatology. 2001;40:202-204.

Harris ED, et al., Overview of the management of rheumatoid arthritis. UptoDate®. Feb. 4, 2008.

Firestein GS. Rheumatoid Arthritis. ACPMedicine. 2007;15(II):1-18.

Bresnihan B., et al. Treatment of rheumatoid arthritis with recombinant human interleukin-1 receptor antagonist. Arthritis Rheum. 1998;41(12):2196-204.

Wooley PH, et al., The effect of an interleukin-1 receptor antagonist protein on type II collagen-induced arthritis and antigen-induced arthritis in mice. Arthritis Rheum. 1993;36(9):1305-14.

* cited by examiner

LIGHT CHAIN

DIQMTQX1TSSLSASX2GDRVTIX1CRASQDISNYLSWYQQKPX3X4X5VKLLIYYTSKLHSGVPSRFSGSGSGTDYX1LTISNLEQEDIATYFC
                                                        CDR1                                  CDR2

LQGKMLPWTFGGGTKLEIK (SEQ ID NO: 1)
CDR3

X1 is T or S; X2 is L or V; X3 is D or G; X4 is G or K; X5 is T or A;

HEAVY CHAIN

QVX10LX11ESGPGX12X13KPSQTLSLTCSFSGFSLSTSGMGVGWIRQPSGKGLEWLAHIWWDGDESYNPSLKX14X15LTISKDTSX16NQVX17LKI
                                                   CDR1                                                          CDR2

TSVX18X19X20DTAX21YFCARX22X23YDPPWFVDWGQGTLVTVSS (SEQ ID NO: 2)
                                  CDR3

X10 is T or Q; X11 is K or Q; X12 is I or L; X13 is L or V; X14 is T or S; X15 is Q or R; X16 is R or K; X17 is F or S; X18 is D or T; X19 is T or A; X20 is V or A; X21 is T or V; X22 is A, V, F, K, or N; X23 is R or K

HEAVY CHAIN CDR3

X22X23YDPPWFVD (SEQ ID NO: 3)

*LIGHT CHAIN*
DIQMTQTTSSLSASLGDRVTISCRASQDISNYLSWYQQKPDGTVKLLIYYTSKLHSGVPSRFSGSGSGTDYSLTISNLEQEDIATYFCLQGKMLPWTFGGG
TKLEIK (SEQ ID NO: 9)

*HEAVY CHAIN*
QVTLKESGPGILKPSQTLSLTCSFSGFSLSTSGMGVGWIRQPSGKGLEWLAHIWWDGDESYNPSLKTQLTISKDTSRNQVFLKITSVDTVDTATYFCARA
RYDPPWFVDWGQGTLVTVSS (SEQ ID NO: 4)

AB2

*LIGHT CHAIN*
DIQMTQTTSSLSASLGDRVTISCRASQDISNYLSWYQQKPDGTVKLLIYYTSKLHSGVPSRFSGSGSGTDYSLTISNLEQEDIATYFCLQGKMLPWTFGGG
TKLEIK (SEQ ID NO: 9)

*HEAVY CHAIN*
QVTLKESGPGILKPSQTLSLTCSFSGFSLSTSGMGVGWIRQPSGKGLEWLAHIWWDGDESYNPSLKTQLTISKDTSRNQVFLKITSVDTVDTATYFCARV
RYDPPWFVDWGQGTLVTVSS (SEQ ID NO: 5)

AB3

*LIGHT CHAIN*
DIQMTQTTSSLSASLGDRVTISCRASQDISNYLSWYQQKPDGTVKLLIYYTSKLHSGVPSRFSGSGSGTDYSLTISNLEQEDIATYFCLQGKMLPWTFGGG
TKLEIK (SEQ ID NO: 9)

*HEAVY CHAIN*
QVTLKESGPGILKPSQTLSLTCSFSGFSLSTSGMGVGWIRQPSGKGLEWLAHIWWDGDESYNPSLKTQLTISKDTSRNQVFLKITSVDTVDTATYFCARE
RYDPPWFVDWGQGTLVTVSS (SEQ ID NO: 6)

AB4

*LIGHT CHAIN*
DIQMTQTTSSLSASLGDRVTISCRASQDISNYLSWYQQKPDGTVKLLIYYTSKLHSGVPSRFSGSGSGTDYSLTISNLEQEDIATYFCLQGKMLPWTFGGG
TKLEIK (SEQ ID NO: 9)

*HEAVY CHAIN*
QVTLKESGPGILKPSQTLSLTCSFSGFSLSTSGMGVGWIRQPSGKGLEWLAHIWWDGDESYNPSLKTQLTISKDTSRNQVFLKITSVDTVDTATYFCARK
KYDPPWFVDWGQGTLVTVSS (SEQ ID NO: 7)

*LIGHT CHAIN*
DIQMTQTTSSLSASLGDRVTISCRASQDISNYLSWYQQKPDGTVKLLIYYTSKLHSGVPSRFSGSGSGTDYSLTISNLEQEDIATYFCLQGKMLPWTFGGGTKLEIK (SEQ ID NO: 9)

*HEAVY CHAIN*
QVTLKESGPGILKPSQTLSLTCSFSGFSLSTSGMGVGWIRQPSGKGLEWLAHIWWDGDESYNPSLKTQLTISKDTSRNQVFLKITSVDTVDTATYFCARNRYDPPWFVDWGQGTLVTVSS (SEQ ID NO: 8)

AB5.1

*LIGHT CHAIN*
DIQMTQSTSSLSASLGDRVTITCRASQDISNYLSWYQQKPGKTVKLLIYYTSKLHSGVPSRFSGSGSGTDYTLTISSLQQEDFATYFCLQGKMLPWTFGQGTKLEIK (SEQ ID NO: 10)

*HEAVY CHAIN*
QVQLQESGPGLLKPSQTLSLTCSFSGFSLSTSGMGVGWIRQPSGKGLEWLAHIWWDGDESYNPSLKSQLTISKDTSKNQVSLKITSVTAADTATYFCARX1X2YDPPWFVDWGQGTLVTVSS (SEQ ID NO: 12)

X1 is A, V, F, K, or N; X2 is R or K;

AB5.2

*LIGHT CHAIN*
DIQMTQSTSSLSASVGDRVTITCRASQDISNYLSWYQQKPGKAVKLLIYYTSKLHSGVPSRFSGSGSGTDYTLTISSLQQEDFATYFCLQGKMLPWTFGQGTKLEIK (SEQ ID NO: 11)

*HEAVY CHAIN*
QVQLQESGPGLVKPSQTLSLTCSFSGFSLSTSGMGVGWIRQPSGKGLEWLAHIWWDGDESYNPSLKSRLTISKDTSKNQVSLKITSVTAADTAVYFCARX1X2YDPPWFVDWGQGTLVTVSS (SEQ ID NO: 13)

*LIGHT CHAIN*
DIQMTQSTSSLSASLGDRVTITCRASQDISNYLSWYQQKPGKTVKLLIYYTSKLHSGVPSRFSGSGSGTDYTLTISSLQQEDFATYFCLQGKMLPWTFG
QGTKLEIK (SEQ ID NO: 10)

*HEAVY CHAIN*
QVQLQESGPGLLKPSQTLSLTCSFSGFSLSTSGMGVGWIRQPSGKGKGLEWLAHIWWDGDESYNPSLKSQLTISKNTSKNQVSLKITSVTAADTATYFC
ARX1X2YDPPWFVDWGQGTLVTVSS (SEQ ID NO: 23)

X1 is A, V, F, K, or N; X2 is R or K;

AB5.4

*LIGHT CHAIN*
DIQMTQSTSSLSASVGDRVTITCRASQDISNYLSWYQQKPGKAVKLLIYYTSKLHSGVPSRFSGSGSGTDYTLTISSLQQEDFATYFCLQGKMLPWTF
GQGTKLEIK (SEQ ID NO: 11)

*HEAVY CHAIN*
QVQLQESGPGLVKPSQTLSLTCSFSGFSLSTSGMGVGWIRQPSGKGLEWLAHIWWDGDESYNPSLKSRLTISKNTSKNQVSLKITSVTAADTAVYFC
ARX1X2YDPPWFVDWGQGTLVTVSS (SEQ ID NO: 24)

LIGHT CHAIN
DIQMTQSTSSLSASLGDRVTITCRASQDISNYLSWYQQKPGKTVKLLIYYTSKLHSGVPSRFSGSGSGTDYTLTISSLQQEDFATYFCLQGKMLPWTF
GQGTKLEIK (SEQ ID NO: 10)

HEAVY CHAIN
QVQLQESGPGLLKPSQTLSLTCSFSGFSLSTSGMGVGWIRQPSGKGLEWLAHIWWDGDESYNPSLKSQLTISKDTSKNQVSLKITSVTAADTATYF
CARNRYDPPWFVDWGQGTLVTVSS (SEQ ID NO: 14)

AB7

LIGHT CHAIN
DIQMTQSTSSLSASVGDRVTITCRASQDISNYLSWYQQKPGKAVKLLIYYTSKLHSGVPSRFSGSGSGTDYTLTISSLQQEDFATYFCLQGKMLPWT
FGQGTKLEIK (SEQ ID NO: 11)

HEAVY CHAIN
QVQLQESGPGLVKPSQTLSLTCSFSGFSLSTSGMGVGWIRQPSGKGLEWLAHIWWDGDESYNPSLKSRLTISKDTSKNQVSLKITSVTAADTAVYF
CARNRYDPPWFVDWGQGTLVTVSS (SEQ ID NO: 15)

LIGHT CHAIN
DIQMTQSTSSLSASLGDRVTITCRASQDISNYLSWYQQKPGKTVKLLIYYTSKLHSGVPSRFSGSGSGTDYTLTISSLQQEDFATYFCLQGKMLPWTF
GQGTKLEIK  (SEQ ID NO: 10)

HEAVY CHAIN
QVQLQESGPGLLKPSQTLSLTCSFSGFSLSTSGMGVGWIRQPSGKGLEWLAHIWWDGDESYNPSLKSQLTISKNTSKNQVSLKITSVTAADTATYF
CARNRYDPPWFVDWGQGTLVTVSS  (SEQ ID NO: 11)

AB9

LIGHT CHAIN
DIQMTQSTSSLSASVGDRVTITCRASQDISNYLSWYQQKPGKAVKLLIYYTSKLHSGVPSRFSGSGSGTDYTLTISSLQQEDFATYFCLQGKMLPWT
FGQGTKLEIK  (SEQ ID NO: 25)

HEAVY CHAIN
QVQLQESGPGLVKPSQTLSLTCSFSGFSLSTSGMGVGWIRQPSGKGLEWLAHIWWDGDESYNPSLKSRLTISKNTSKNQVSLKITSVTAADTAVYF
CARNRYDPPWFVDWGQGTLVTVSS  (SEQ ID NO: 26)

Fig. 4B

IL-1β BINDING ANTIBODIES AND FRAGMENTS THEREOF

CROSS-REFERENCE TO RELATED APPLICATION

This application claims priority of U.S. provisional application Ser. No. 60/692,830 filed Jun. 21, 2005, the disclosure of which is incorporated herein by reference.

FIELD OF INVENTION

The invention relates to IL-1β binding antibodies and including fragments thereof, and nucleic acids encoding such antibodies, as well as to vectors, cells, and compositions comprising the antibodies or nucleic acids, and uses thereof.

BACKGROUND OF THE INVENTION

The interleukin-1 (IL-1) family of cytokines has been implicated in disease states such as rheumatoid arthritis (RA), osteoarthritis, Crohn's disease, ulcerative colitis (UC), septic shock, chronic obstructive pulmonary disease (COPD), asthma, graft versus host disease, atherosclerosis, adult T-cell leukemia, multiple myeloma, multiple sclerosis, stroke, and Alzheimer's disease. IL-1 family members include IL-1α, IL-1β, and IL-1Ra. Although related by their ability to bind to IL-1 receptors (IL-1R1 and IL-1R2), each of these cytokines is expressed by a different gene and has a different primary amino acid sequence. Furthermore, the physiological activities of these cytokines can be distinguished.

Compounds that disrupt IL-1 receptor signaling have been investigated as therapeutic agents to treat IL-1 mediated diseases. These compounds include recombinant IL-1Ra (Amgen Inc., Thousand Oaks, Calif.) and IL-1 receptor "trap" peptide (Regeneron Inc., Tarrytown, N.Y.). Animal-derived monoclonal antibodies that bind IL-1 cytokines also have been investigated. However, their clinical value can be limited due to their immunogenicity. For example, human subjects administered with mouse monoclonal antibodies have been known to produce human anti-mouse antibodies (HAMA). HAMA have been reported to reduce the efficacy of monoclonal antibody therapy and to produce adverse reactions, including kidney damage. Other IL-1β antibodies may be limited by their binding affinity and/or their potency. Accordingly, additional compounds that disrupt IL-1 receptor signaling are needed. The invention provides such compounds, as well as methods for preparing and using such compounds.

BRIEF SUMMARY

The invention provides an IL-1β binding antibody or IL-1β binding fragment thereof comprising the amino acid sequence of SEQ ID NO: 2. Also provided herein is a nucleic acid encoding the antibody or antibody fragment, as well as a vector comprising the nucleic acid, a cell comprising the nucleic acid or vector, and a composition comprising the antibody, nucleic acid, or vector.

The invention further provides a method of treating or preventing a disease in a mammal comprising administering an effective amount of an antibody or antibody fragment, nucleic acid, or vector of the invention to a mammal in need thereof, whereby a disease is treated or prevented in the mammal.

The invention provides a method of preparing an affinity matured IL-1β binding polypeptide comprising (a) providing a first nucleic acid comprising a nucleic acid sequence encoding an IL-1β binding polypeptide that comprises the amino acid sequence of any of SEQ ID NOS: 1-26 and a second nucleic acid comprising a nucleic acid sequence that differs from the first nucleic acid sequence by at least one nucleotide, (b) performing nucleic acid shuffling to provide two or more mutated nucleic acids, (c) selecting for a mutated nucleic acid that encodes a polypeptide that (i) binds to IL-1β with a greater affinity than the polypeptide encoded by the first nucleic acid, (ii) has a selectivity for IL-1β over IL-1α that is greater than that of the polypeptide encoded by the first nucleic acid, (iii) has an equilibrium binding dissociation constant ($K_D$) for IL-1β that is lower than that of the polypeptide encoded by the first nucleic acid, or (iv) inhibits IL-1β induced expression of serum IL-6 in an animal to a greater degree than the polypeptide encoded by the first nucleic acid, and (d) expressing the selected mutated nucleic acid, whereby an affinity matured IL-1β binding polypeptide is produced.

The invention provides novel IL-1β binding antibodies or IL-1β binding fragments thereof, which bind to human IL-1β with a dissociation constant lower than 3 pM, alternatively about 2 pM or less, preferably about 1 pM or less. Such high affinity antibodies are contemplated as being useful for various methods of treating or preventing IL-1 related diseases or conditions. Alternatively or additionally, the IL-1β binding antibodies or IL-1β binding fragments bind to an IL-1β epitope such that the bound antibody or fragment does not substantially prevent the IL-1β from binding to IL-1 receptor type I. Alternatively or additionally, the IL-1β binding antibodies or IL-1β binding fragments bind to substantially the same epitope as one or more of the exemplary antibodies described herein, such as the antibody designated AB7 which comprises a heavy chain variable region. Alternatively or additionally, the IL-1β binding antibodies or IL-1β binding fragments compete with the binding of an antibody having the light chain variable region of SEQ ID NO:11 and the heavy chain variable region of SEQ ID NO:15. Alternatively or additionally, the present invention encompasses IL-1β binding antibodies or IL-1β binding fragments that bind to an epitope contained in the sequence ESVDPKNYPKKK-MEKRFVFNKIE (SEQ ID NO:36). Exemplary IL-1β binding antibodies include the antibodies designated AB5 and AB7 herein.

The invention also provides IL-1 binding antibodies or IL-1β binding fragments thereof having a dissociation constant of less than 3 pM, alternatively about 1 pM or less, alternatively any of the other dissociation constants disclosed herein, and comprising a heavy chain variable region comprising one of the amino acid sequences of SEQ ID NO: 12, 13, 21, 23 or 24, or alternatively the amino acid sequence of SEQ ID NO: 12, 13 or 21, or alternatively the amino acid sequence of SEQ ID NO: 13 or 21, or alternatively the amino acid sequence of SEQ ID NO: 8, 14 or 15, or alternatively the amino acid sequence of SEQ ID NO: 8 or 15. The IL-1β binding antibody or IL-1β binding fragment can also comprise light chain variable region comprising the amino acid sequence of SEQ ID NO: 9, SEQ ID NO: 10, or SEQ ID NO: 11.

As another embodiment of the present invention, novel IL-1β binding antibodies, or IL-1β binding fragments thereof, are provided which bind IL-1β with a dissociation constant between about 6 pM and about 50 pM, alternatively between about 13 pM and about 25 pM, alternatively about 19 pM, and where the antibody or fragment has an $IC_{50}$ less than 0.5 nM (500 pM), alternatively between about 5 pM and about 200 pM, alternatively between about 10 pM and about 100 pM, alternatively about 30 pM, for inhibiting IL-1β stimulated release of IL-6 from human fibroblasts. $IC_{50}$ for inhibiting IL-1β stimulated release of IL-6 from human fibroblasts refers the concentration required to inhibit 50% of IL-6 released by IL-1β stimulation of the human fibroblasts. Exemplary antibodies include the antibody designated AB1 herein.

The present invention also provides IL-1 binding antibodies or IL-1β binding fragments thereof having a dissociation constant between about 6 and about 50 pM and comprising a heavy chain variable region comprising one of the amino acid sequences of SEQ ID NOS: 4, 5 or 6, alternatively one of the amino acid sequences of SEQ ID NOS: 4 or 5, alternatively the amino acid sequences of SEQ ID NO: 4. It is contemplated that in some circumstances, an IL-1β binding antibody or IL-1β binding fragment having a relatively higher dissociation constant may be desirable, for example, for some methods of treating or preventing IL-1 related diseases or conditions where a relatively lower degree of affinity is desirable.

Exemplary antibodies include the antibodies designated AB1, AB2, AB3, AB4, AB5, AB6, AB7, AB8, and AB9. AB1 comprises a heavy chain variable region comprising the amino acid sequence of SEQ ID NO:4 and a light chain variable region comprising the amino acid sequence of SEQ ID NO:9. AB2 comprises a heavy chain variable region comprising the amino acid sequence of SEQ ID NO:5 and a light chain variable region comprising the amino acid sequence of SEQ ID NO:9. AB3 comprises a heavy chain variable region comprising the amino acid sequence of SEQ ID NO:6 and a light chain variable region comprising the amino acid sequence of SEQ ID NO:9. AB4 comprises a heavy chain variable region comprising the amino acid sequence of SEQ ID NO:7 and a light chain variable region comprising the amino acid sequence of SEQ ID NO:9. AB5 comprises a heavy chain variable region comprising the amino acid sequence of SEQ ID NO:8 and a light chain variable region comprising the amino acid sequence of SEQ ID NO:9. AB6 comprises a heavy chain variable region comprising the amino acid sequence of SEQ ID NO:14 and a light chain variable region comprising the amino acid sequence of SEQ ID NO:10. AB7 comprises a heavy chain variable region comprising the amino acid sequence of SEQ ID NO:15 and a light chain variable region comprising the amino acid sequence of SEQ ID NO:11. AB8 comprises has a heavy chain variable region comprising the amino acid sequence of SEQ ID NO:25 and a light chain variable region comprising the amino acid sequence of SEQ ID NO:10. AB9 comprises a heavy chain variable region comprising the amino acid sequence of SEQ ID NO:26 and a light chain variable region comprising the amino acid sequence of SEQ ID NO:11.

The present invention encompasses IL-1β binding antibodies or IL-1β binding fragments having a heavy chain variable region that comprises any one of the sequences set forth in SEQ ID NO:2, 4-8, 12-15, 21, 23-26, 28-35, or 42-57, alternatively any one of the sequences set forth in SEQ ID NO: 21, alternatively any one of the sequences set forth in SEQ ID NO: 4, SEQ ID NO: 5, SEQ ID NO: 6, SEQ ID NO: 7, or SEQ ID NO: 8, alternatively any one of the sequences set forth in SEQ ID NO: 12 or SEQ ID NO: 13, alternatively any one of the sequences set forth in SEQ ID NO: 14, SEQ ID NO: 15, SEQ ID NO: 25, or SEQ ID NO: 26.

The invention also encompasses IL-1β binding antibodies or IL-1β binding fragments having a light chain variable region that comprises any one of the sequences set forth in SEQ ID NO:1, 9-11, or 27, alternatively any one of the sequences set forth SEQ ID NO: 1, alternatively any one of the sequences set forth in SEQ ID NO: 9, alternatively any one of the sequences set forth in SEQ ID NO: 10 or SEQ ID NO: 11.

The present invention also encompasses IL-1β antibodies or IL-1β binding fragments comprising one of the heavy chain variable regions of the sequences set forth in SEQ ID NO:2, 4-8, 12-15, 21, 23-26, 28-35, or 42-57, and one of the light chain variable regions of the sequences set forth in SEQ ID NO:1, 9-11, or 27.

The present invention also encompasses IL-1β binding antibodies or IL-1β binding fragments comprising portions that do not bind IL-1β but instead are responsible for other functions, such as circulating half-life, direct cytotoxic effect, detectable labeling, or activation of a recipient's endogenous complement cascade or endogenous cellular cytotoxicity. Antibodies of the invention may comprise all or a portion of a constant region of an antibody. The constant region may be selected from any isotype, including IgA (e.g., IgA1 or IgA2), IgD, IgE, IgG (e.g. IgG1, IgG2, IgG3 or IgG4), or IgM. For example, the antibody may comprise an IgG2 region. In addition to, or instead of, comprising a constant region, the antibodies and fragments of the invention may include an epitope tag, a salvage receptor epitope, a label moiety for diagnostic or purification purposes, or a cytotoxic moiety such as a radionuclide or toxin.

The present invention also encompasses pharmaceutical compositions comprising any one of the IL-1β binding antibodies or IL-1β binding fragments and a pharmaceutically suitable carrier, excipient or diluent. Preferably the antibodies and compounds of the invention can be administered in a therapeutically effective amount, that is, an amount sufficient to ameliorate a clinical sign or symptom of a condition or disorder associated with the target protein expression, to a subject in need of such treatment. In a related embodiment, the pharmaceutical composition further comprises a second active agent. In yet another related embodiment, the pharmaceutical composition is provided wherein the second active agent is an antibody to or antagonist of growth factor or, a cytokine. In another embodiment the second active agent is another antibody.

In another embodiment of the present invention, the use of the IL-1β antibodies or IL-1β binding fragments is contemplated in the manufacture of a medicament for preventing or reducing a condition or disorder associated with IL-1. In any of the uses, the medicament can be coordinated with treatment using a second active agent. In another embodiment of the invention, the use of a synergistic combination of an antibody of the invention for preparation of a medicament for treating a patient exhibiting symptoms of a IL-1 related condition or disorder disclosed herein wherein the medicament is coordinated with treatment using a second active agent is contemplated. In a related embodiment, the second active agent is an antibody to or antagonist of cytokine or, a growth factor. Embodiments of any of the aforementioned uses are contemplated wherein the amount of the IL-1β binding antibody or fragment in the medicament is at a dose effective to reduce the dosage of second active agent required to achieve a therapeutic effect.

Kits are also contemplated by the present invention. In one embodiment, a kit comprises a therapeutically or prophylactically effective amount of a compound or composition of the invention (such as an antibody, fragment, nucleic acid, vector or cell), packaged in a container, such as a vial or bottle, and further comprising a label attached to or packaged with the container, the label describing the contents of the container and providing indications and/or instructions regarding use of the contents of the container to prevent or reduce a condition or disease associated with target protein expression.

BRIEF DESCRIPTION OF THE SEVERAL VIEWS OF THE DRAWING(S)

FIG. 1 is a pair of amino acid sequences corresponding to the light chains and heavy chains of the variable region of some of the antibodies described herein. The underlined portions of the amino acid sequences indicate complementarity determining regions (CDRs).

FIG. 2 is a set of amino acid sequences corresponding to the light chain and heavy chain variable regions of antibodies AB1, AB2, AB3, and AB4. The underlined portions of the amino acid sequences indicate complementarity determining regions (CDRs).

FIG. 3 is a set of amino acid sequences corresponding to the light chain and heavy chain variable regions of antibodies AB5, AB5.1, and AB5.2. The underlined portions of the amino acid sequences indicate complementarity determining regions (CDRs).

FIG. 4 is a set of amino acid sequences corresponding to the light chain and heavy chain variable regions of antibodies AB5.3 and AB5.4. The underlined portions of the amino acid sequences indicate complementarity determining regions (CDRs).

FIG. 4A is a set of amino acid sequences corresponding to the light chain and heavy chain variable regions of antibodies AB6 and AB7. The underlined portions of the amino acid sequences indicate complementarity determining regions (CDRs).

FIG. 4B is a set of amino acid sequences corresponding to the light chain and heavy chain variable regions of antibodies AB8 and AB9. The underlined portions of the amino acid sequences indicate complementarity determining regions (CDRs).

DETAILED DESCRIPTION

Figure 5:
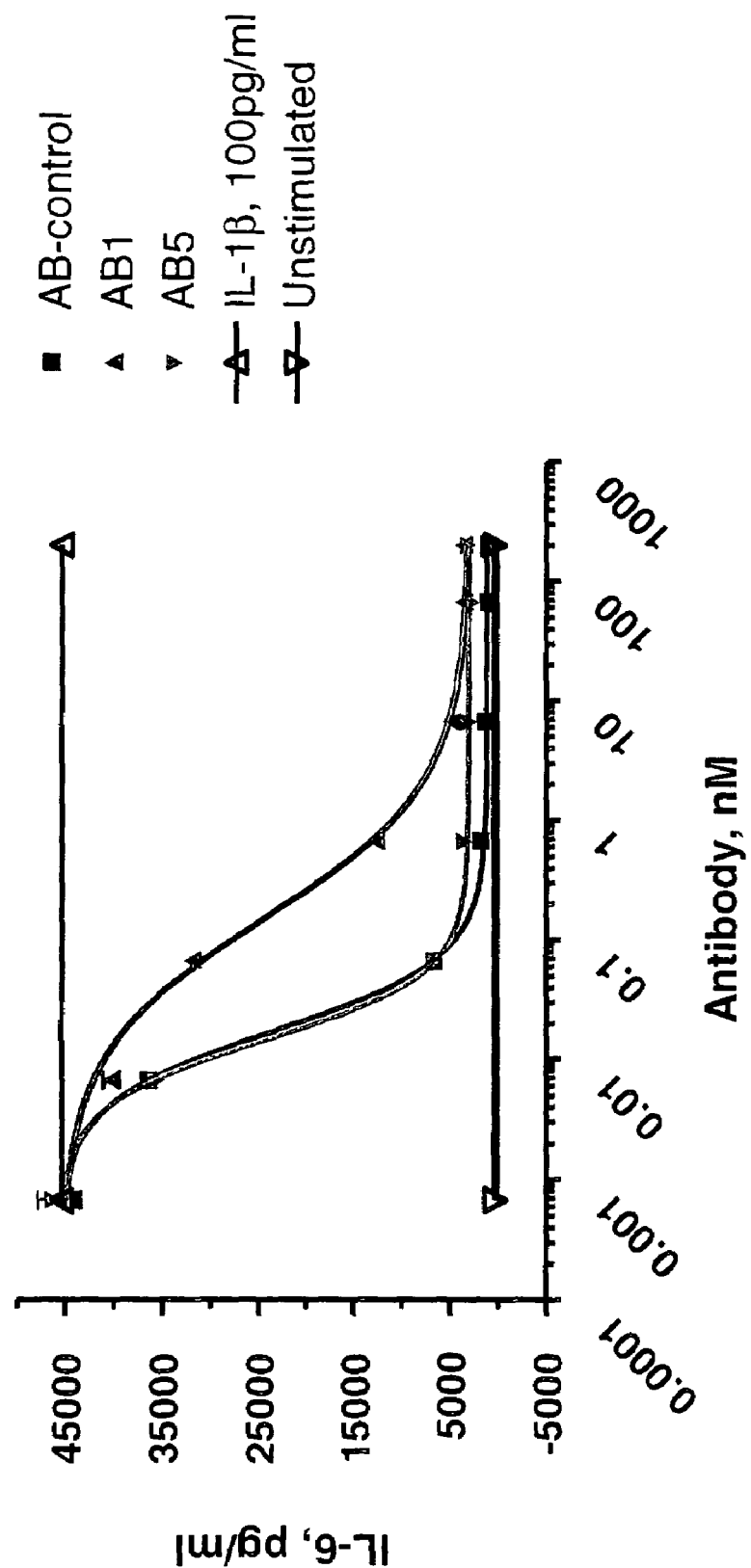
FIG. 5 is graph showing the results of an in vitro IL-1β stimulation experiment.

The present invention encompasses novel IL-1β antibodies and fragments having desirable affinity and potency. As one aspect of the present invention, IL-1β binding antibodies are provided which have unexpectedly high affinity and low dissociation constants (for example, less than 3 pM, alternatively about 1 pM or less) compared to known IL-1β binding antibodies. Exemplary antibodies include the antibodies designated AB5 and AB7 herein. As another aspect of the present invention, IL-1β binding antibodies are provided having a desirable dissociation constant (for example, between about 6 pM and about 50 pM) and a desirable $IC_{50}$ (for example, less than 500 pM) for inhibiting IL-1β stimulated release of IL-6 from human fibroblasts. Exemplary antibodies include the antibody designated AB1 herein.

The present invention also encompasses IL-1β binding antibodies or IL-1β binding fragments that bind selectively to IL-1β, in that they bind to IL-1β with greater affinity than to other antigens. The IL-1β binding antibodies or IL-1β binding fragments may bind selectively to human IL-1β, but also bind detectably to non-human IL-1β. Alternatively or additionally, the antibodies or fragments may bind to human IL-1β and to IL-1β of at least one other mammal (a first mammal) and not to IL-1β of at least one other mammal (a second mammal). For example, the antibodies or fragments may bind to one or more of rodent IL-1β, primate IL-1β, dog IL-1β, and rabbit IL-1β, and/or not bind to guinea pig IL-1β. Alternatively or additionally, the antibodies or fragments may bind to mouse IL-1β with higher affinity than to rat IL-1β. Alternatively or additionally, the IL-1β binding antibodies or IL-1β binding fragments may have the same or substantially the same potency against human IL-1β and primate IL-1β. Alternatively or additionally, the IL-1β binding antibodies or IL-1β binding fragments may have the same or substantially the same potency against recombinant human IL-1β and endogenous human IL-1β. Alternatively or additionally, the IL-1β binding antibodies or IL-1β binding fragments may neutralize mouse IL-1β.

As used herein, an antibody or fragment that specifically binds with a target antigen refers to an antibody that binds the target antigen with greater affinity than with similar antigens. For example, an antibody or fragment is specific for its cognate antigen when the variable regions of the antibody or fragment recognize and bind the cognate antigen with a detectable preference (distinguishing the antigen from other known polypeptides of the same family, by virtue of measurable differences in binding affinity, despite the possible existence of localized sequence identity, homology, or similarity between family members). It will be understood that specific antibodies and fragments may also interact with other proteins (for example, *S. aureus* protein A or other antibodies in ELISA techniques) through interactions with sequences outside the variable region of the antibodies, and in particular, in the constant region of the antibody or fragment. Screening assays to determine binding specificity of an antibody are well known and routinely practiced in the art. For a comprehensive discussion of such assays, see Harlow et al. (Eds), *Antibodies A Laboratory Manual*; Cold Spring Harbor Laboratory; Cold Spring Harbor, N.Y. (1988), Chapter 6.

An aspect of the present invention encompasses IL1β binding antibodies and IL1β binding fragments thereof having unexpectedly low dissociation constants ($K_D$), for example, less than 3 pM, alternatively 2 pM or less, alternatively 1 pM or less, alternatively 0.8 pM or less, alternatively 0.74 pM or less, alternatively 0.72 pM or less, alternatively 0.7 pM or less, alternatively 0.6 pM or less, alternatively 0.56 pM or less, alternatively 0.5 pM or less, alternatively 0.3 pM or less, alternatively 0.26 pM or less, alternatively 0.24 pM or less, alternatively 0.2 pM or less. Thus, in some embodiments of the present invention, IL1β binding antibodies and fragments may be described by reference to a high end of a range of dissociation constants. Additionally or alternatively, in some embodiments of the present invention, IL1β binding antibodies and fragments may be described by reference to a low end of a range of dissociation constants, such as for example, an antibody or fragment having a dissociation constant of 0.07 pM or higher, alternatively 0.1 pM or higher, alternatively 0.11 pM or higher, alternatively 0.15 pM or higher, alternatively 0.2 pM or higher, alternatively 0.24 pM or higher, alternatively 0.26 pM or higher, alternatively 0.3 pM or higher, alternatively 0.5 pM or higher, alternatively 0.7 pM or higher. Any higher dissociation constant and lower dissociation constant, as specified above, may be combined to define a range of dissociation constants, providing that the lower value selected is equal to or less than the higher value selected.

Another aspect of the present invention provides novel IL-1β binding antibodies, and IL-1β binding fragments thereof, which bind IL-1β with a dissociation constant greater than 6 pM and less than or equal to 50 pM, alternatively between about 13 pM and about 25 pM, and where the antibody or fragment has an $IC_{50}$ for inhibiting IL-1β stimulated release of IL-6 from human fibroblasts that is less than 0.5 nM (500 pM), alternatively between about 5 pM and about 200 pM, alternatively between about 10 pM and about 100 pM, alternatively about 30 pM. It is contemplated that it may be desirable to provide an IL-1β binding antibody or fragment having the foregoing binding affinity and potency for some methods of treating or preventing IL-1β mediated conditions or diseases. Exemplary antibodies include the antibody designated AB1 herein.

The present antibodies and fragments bind to IL-1β with high affinity, as indicated by the dissociation constants set forth herein. Affinity constants characterizing the affinities of antibodies to antigens may be association constants measured by the kinetics of antigen-antibody complex formation. Alternatively, binding affinity may be characterized by a dissociation constant which is the inverse of the association constant. The term $K_D$, as used herein, is intended to refer to the dissociation constant of an antibody-antigen interaction.

The present invention also encompasses neutralizing antibodies or neutralizing fragments thereof which bind to IL-1β so as to neutralize biological activity of the IL-1. Neutralization of biological activity of IL-1β can be assessed by assays for one or more indicators of IL-1β biological activity, such as IL-1β stimulated release of IL-6 from human fibroblasts or other cells, IL-1β induced release of IL-8 from blood cells, or IL-1 induced proliferation of T helper cells. Preferably the IL-1β binding antibodies and fragments of the present invention neutralize the biological activity of IL-1β connected with the signaling function of IL-1 receptor type I (IL-1RI) bound by the IL-1β.

In general, the neutralizing antibodies and fragments of the present invention can neutralize the biological activity of IL-1β, regardless of whether the binding of IL-1β to IL1 receptor type I is blocked. More preferably, the IL-1β binding antibodies or IL-1β binding fragments neutralize the biological activity of IL-1β by binding to IL-1β, without substantially preventing the binding of the bound IL-1β to IL-1 receptor type I. A potential advantage of such antibodies and fragments is that they can bind and neutralize IL-1β while still permitting the IL-1β to bind to IL-1RI. This can result in an effective reduction in IL-1α biological activity as well as IL-1β biological activity, since there are fewer unbound IL-1RI sites for IL-1α to bind to. Thus, IL-1β binding antibodies and fragments of the present invention are useful in methods where it is desirable to neutralize IL-1 biological activity in vitro an in vivo.

The present antibodies or fragments may be neutralizing antibodies or fragments which bind specifically to IL-1β epitope that affects biological activity of IL-1β. The present antibodies or fragments can bind to a neutralization-sensitive epitope of IL-1β. When a neutralization-sensitive epitope of IL-1β is bound by one of the present antibodies or fragments, the result is a loss of biological activity of the IL-1β containing the epitope.

In some embodiments, the IL-1β binding antibodies or IL-1β binding fragments may have an $IC_{50}$ for inhibiting IL-1β stimulated release of IL-1β from blood cells that is less than 50 pM, alternatively about 25 pM or less, alternatively about 10 pM or less, alternatively about 2 pM or less. $IC_{50}$ for inhibiting IL-1β stimulated release of IL-1β from blood cells refers the concentration required to inhibit 50% of IL-8 released by IL-1β stimulation of blood cells. Exemplary antibodies include the antibody designated AB7 herein.

The present invention also encompasses an IL-1β binding antibody or IL-1β binding fragment thereof, comprising a changed amino acid sequence, wherein the changed amino acid has one or at least one substitution, addition or deletion from a starting amino acid sequence selected from SEQ ID NOS:27 or 28 (or any of the other sequences disclosed herein), where the changed antibody or fragment has the same or substantially the same affinity and specificity of epitope binding as the starting amino acid sequence. It is contemplated that one or more substitutions, deletions, or additions may be made to the IL-1β binding antibodies or IL-1β binding fragments provided herein, such as antibodies or fragments comprising SEQ ID NO:28 and/or SEQ ID NO:27, while maintaining the same or substantially the same affinity and specificity of epitope binding of the starting antibody or fragment. For example, the present invention encompasses an IL-1β binding antibody or IL-1β binding fragment thereof, comprising a changed amino acid sequence, wherein the changed amino acid has one or at least one substitution, addition or deletion from a starting amino acid sequence comprising SEQ ID NO:8 (or any of the other sequences disclosed herein can be used as a starting sequence), where the changed antibody or fragment has the same or substantially the same affinity and specificity of epitope binding as the starting amino acid sequence comprising SEQ ID NO:8 (or the particular sequence that is used as the starting amino acid sequence). By the phrase "substantially the same" affinity, it is meant that the affinity or dissociation constant as determined by the teachings herein, is not increased or decreased more than inherent variation in the assay for an antibody or fragment comprising SEQ ID NOS:28 or 27, such as the variation observed when the assay is performed three or more independent times. By the phrase "substantially the same" epitope specificity, it is meant that binding to an amino acid sequence containing the epitope as determined by the teachings herein is within inherent variation in the assay for an antibody or fragment comprising SEQ ID NOS:28 or 27, such as the variation observed when performed three or more independent times. When comparing to an antibody or fragment comprising SEQ ID NOS:28 or 27, it is meant that the comparison should be made between the changed amino acid sequence and the starting amino acid sequence from which the one or more substitutions, deletions, or additions were made, such starting sequence being identical at all other amino acids.

Antibodies, Humanized Antibodies, and Human Engineered Antibodies

The IL-1β binding antibodies of the present invention may be provided as polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Antibodies generally comprise two heavy chain polypeptides and two light chain polypeptides, though single domain antibodies having one heavy chain and one light chain and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain. The constant region need not be present in an antigen binding fragment of an antibody. Antigen binding fragments of an antibody disclosed herein can include Fab, Fab', F(ab')$_2$, and F(v) antibody fragments. As discussed in more detail below, IL-1β binding fragments encompass antibody fragments and antigen-binding polypeptides that will bind IL-1β.

Each of the heavy chain and light chain sequences of an antibody, or antigen binding fragment thereof, includes a variable region with three complementarity determining regions (CDRs) as well as non-CDR framework regions (FRs). The terms "heavy chain" and "light chain," as used herein, mean the heavy chain variable region and the light chain variable region, respectively, unless otherwise noted. Heavy chain CDRs are referred to herein as CDR-H1, CDR-H2, and CDR-H3. Light chain CDRs are referred to herein as CDR-L1, CDR-L2, and CDR-L3. Variable regions and CDRs in an antibody sequence can be identified (i) according to general rules that have been developed in the art or (ii) by aligning the sequences against a database of known variable regions. Methods for identifying these regions are described in Kontermann and Dubel, eds., *Antibody Engineering*, Springer, New York, N.Y., 2001, and Dinarello et al., *Current Protocols in Immunology*, John Wiley and Sons Inc., Hoboken, N.J., 2000. Databases of antibody sequences are described in and can be accessed through "The Kabatman" database at www.bioinf.org.uk/abs (maintained by A. C. Martin in the Department of Biochemistry & Molecular Biology University College London, London, England) and VBASE2 at www.vbase2.org, as described in Retter et al., *Nucl. Acids Res.*, 33(Database issue): D671-D674 (2005). The "Kabatman" database web site also includes general rules of thumb for identifying CDRs. The term "CDR," as used herein, is as defined in Kabat et al., *Sequences of Immunological Interest*, 5$^{th}$ ed., U.S. Department of Health and Human Services, 1991, unless otherwise indicated.

The present invention encompasses IL-1β binding antibodies that include two full length heavy chains and two full length light chains. Alternatively, the IL-1β binding antibodies can be constructs such as single chain antibodies or "mini" antibodies that retain binding activity to IL-1β. Such constructs can be prepared by methods known in the art such as, for example, the PCR mediated cloning and assembly of single chain antibodies for expression in *E. coli* (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, for example, in a second PCR step, through a linker DNA that encodes a flexible protein linker composed of the amino acids Gly and Ser. This linker allows the variable heavy and light chain portions to fold in such a way that the antigen binding pocket is regenerated and antigen is bound with affinities often comparable to the parent full-length dimeric immunoglobulin molecule.

The IL-1β binding antibodies and fragments of the present invention encompass variants of the exemplary antibodies, fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment comprising one or more of amino acid sequence of SEQ ID NOS:1-35 or 42-57, where the changed antibody or fragment has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the present antibodies and IL-1β binding fragments may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of IL-1β binding antibodies and IL-1β binding fragments may also be prepared by mutagenesis techniques. For example, amino acid changes may be introduced at random throughout an antibody coding region and the resulting variants may be screened for binding affinity for IL-1β or for another property. Alternatively, amino acid changes may be introduced in selected regions of an IL-1β antibody, such as in the light and/or heavy chain CDRs, and/or in the framework regions, and the resulting antibodies may be screened for binding to IL-1β or some other activity. Amino acid changes encompass one or more amino acid substitutions in a CDR, ranging from a single amino acid difference to the introduction of multiple permutations of amino acids within a given CDR, such as CDR3. In another method, the contribution of each residue within a CDR to IL-1β binding may be assessed by substituting at least one residue within the CDR with alanine. Lewis et al. (1995), Mol. Immunol. 32: 1065-72. Residues which are not optimal for binding to IL-1β may then be changed in order to determine a more optimum sequence. Also encompassed are variants generated by insertion of amino acids to increase the size of a CDR, such as CDR3. For example, most light chain CDR3 sequences are nine amino acids in length. Light chain sequences in an antibody which are shorter than nine residues may be optimized for binding to IL-1β by insertion of appropriate amino acids to increase the length of the CDR.

Variants may also be prepared by "chain shuffling" of light or heavy chains. Marks et al. (1992), Biotechnology 10: 779-83. A single light (or heavy) chain can be combined with a library having a repertoire of heavy (or light) chains and the resulting population is screened for a desired activity, such as binding to IL-1β. This permits screening of a greater sample of different heavy (or light) chains in combination with a single light (or heavy) chain than is possible with libraries comprising repertoires of both heavy and light chains.

The IL-1β binding antibodies and fragments of the present invention encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The IL-1β binding antibodies and fragments of the present invention can be bispecific. Bispecific antibodies or fragments can be of several configurations. For example, bispecific antibodies may resemble single antibodies (or antibody fragments) but have two different antigen binding sites (variable regions). Bispecific antibodies can be produced by chemical techniques (Kranz et al. (1981), Proc. Natl. Acad. Sci. USA, 78: 5807), by "polydoma" techniques (U.S. Pat. No. 4,474,893) or by recombinant DNA techniques. Bispecific antibodies of the present invention can have binding specificities for at least two different epitopes, at least one of which is an epitope of IL-1β. The IL-1β binding antibodies and fragments can also be heteroantibodies. Heteroantibodies are two or more antibodies, or antibody binding fragments (Fab) linked together, each antibody or fragment having a different specificity.

Techniques for creating recombinant DNA versions of the antigen-binding regions of antibody molecules which bypass the generation of monoclonal antibodies are contemplated for the present IL-1β binding antibodies and fragments. DNA is cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind IL-1β. Such IL-1β binding agents (Fab fragments with specificity for an IL-1β polypeptide) are specifically encompassed within the IL-1β binding antibodies and fragments of the present invention.

The present IL-1β binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA,* 81: 6841-6855 (1984), Boulianne, et al., *Nature,* 312: 643-646 (1984), and PCT Application Publication WO 86/01533. Although, they can be less immunogenic than a mouse monoclonal antibody, administrations of chimeric antibodies have been associated with human immune responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), Proc. Natl. Acad. Sci., 81: 6851; Neuberger et al. (1984), Nature, 312: 604. One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature,* 321: 522-525 (1986), Riechmann et al., *Nature,* 332: 323-327 (1988), and Verhoeyen et al., *Science,* 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature,* 332: 323-327 (1988), and Verhoeyen et al., *Science,* 239: 1534-1536 (1988).

Human engineered antibodies include "veneered" antibodies and antibodies prepared using HUMANENGINEERING™ technology (XOMA (US) LLC, Berkeley, Calif.). HUMANENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or antigen-binding properties. Thus, a low risk position is one for which a substitution is predicted to be beneficial because it is predicted to reduce immunogenicity without significantly affecting antigen binding properties. A moderate risk position is one for which a substitution is predicted to reduce immunogenicity, but is more likely to affect protein folding and/or antigen binding. High risk positions contain residues most likely to be involved in proper folding or antigen binding. Generally, low risk positions in a non-human antibody are substituted with human residues, high risk positions are rarely substituted, and humanizing substitutions at moderate risk positions are sometimes made, although not indiscriminately. Positions with prolines in the non-human antibody variable region sequence are usually classified as at least moderate risk positions.

The particular human amino acid residue to be substituted at a given low or moderate risk position of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., *Protein Engineering,* 7: 805-814 (1994), U.S. Pat. Nos. 5,766,886, 5,770, 196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMANENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering,* Springer, New York, N.Y., 2001.

Exemplary humanized or human engineered antibodies include IgG, IgM, IgE, IgA, and IgD antibodies. The present antibodies can be of any class (IgG, IgA, IgM, IgE, IgD, etc.) or isotype and can comprise a kappa or lambda light chain. For example, a human antibody can comprise an IgG heavy chain or defined fragment, such as at least one of isotypes, IgG1, IgG2, IgG3 or IgG4. As a further example, the present antibodies or fragments can comprise an IgG1 heavy chain and an IgG1 light chain.

The present antibodies and fragments can be human antibodies, such as antibodies which bind IL-1β polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies can also be generated through the in vitro screening of phage display antibody libraries. See Hoogenboom et al. (1991), J. Mol. Biol. 227: 381; and Marks et al. (1991), J. Mol. Biol. 222: 581. Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify selective binding agents of IL-1β.

The IL-1β binding antibodies and fragments may comprise one or more portions that do not bind IL-1β but instead are responsible for other functions, such as circulating half-life, direct cytotoxic effect, detectable labeling, or activation of the recipient's endogenous complement cascade or endogenous cellular cytotoxicity. The antibodies or fragments may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

The constant region (when present) of the present antibodies and fragments may be of the γ1, γ2, γ3, γ4, μ, β2, or δ or ε type, preferably of the γ type, more preferably of the y, type, whereas the constant part of a human light chain may be of the κ or λ type (which includes the $\lambda_1$, $\lambda_2$ and $\lambda_3$ subtypes) but is preferably of the κ type.

Variants also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity.

For example, the present IL-1β binding antibodies and fragments may comprise a modified Fc region. Fc region refers to naturally-occurring or synthetic polypeptides homologous to the IgG C-terminal domain that is produced upon papain digestion of IgG. IgG Fc has a molecular weight of approximately 50 kD. In the present antibodies and fragments, an entire Fc region can be used, or only a half-life enhancing portion. In addition, many modifications in amino acid sequence are acceptable, as native activity is not in all cases necessary or desired.

The Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Various mutations for human IgG also are known (see, e.g., Morrison et al., 1994, The Immunologist 2: 119 124 and Brekke et al., 1994, The Immunologist 2: 125).

In some embodiments, the present an antibodies or fragments are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG$_1$, IgG$_2$, IgG$_3$, or IgG$_4$) that is responsible for increasing the in vivo serum half-life of the IgG molecule.

A salvage receptor binding epitope can include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the C$_L$ region or V$_L$ region, or both, of the antibody fragment. See also International applications WO 97/34631 and WO 96/32478 which describe Fc variants and their interaction with the salvage receptor.

Mutation of residues within Fc receptor binding sites can result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position). For example it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., *Mol. Immunol.* 30:105-8, 1993).

Preferably, the antibody or antibody fragment of the present invention does not cross-react with any target other than IL-1β. For example, the present antibodies and fragments preferably do not detectably bind to IL-1α.

IL-1β Binding Antibody or Antibody Fragment

Antibody fragments are portions of an intact full length antibody, such as an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, and multi-specific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; V$_{HH}$ containing antibodies; and any other polypeptides formed from antibody fragments.

The invention provides an IL-1β binding antibody or IL-1β binding fragment thereof comprising SEQ ID NO: 2. FIG. 1 illustrates the amino acid sequence of SEQ ID NO: 2. Preferably, the antibody or antibody fragment comprises the amino acid sequence of SEQ ID NO: 21, and more preferably comprises the amino acid sequence of SEQ ID NO: 4, SEQ ID NO: 5, SEQ ID NO: 6, SEQ ID NO: 7, or SEQ ID NO: 8. Antibodies of the invention also can comprise the amino acid sequence of SEQ ID NO: 12 or SEQ ID NO: 13, and preferably comprise SEQ ID NO: 14 or SEQ ID NO: 15. Typically, the antibody or antibody fragment comprises a light chain variable region and a heavy chain variable region, and the heavy chain variable region comprises the amino acid sequence of SEQ ID NO: 2 (e.g., comprises the amino acid sequence of SEQ ID NOS: 4-8, 12-15, or 21). The light chain of the antibody preferably comprises, consists essentially of, or consists of the amino acid sequence of SEQ ID NO: 1. Thus, for example, the light chain of the antibody can comprise, consist essentially of, or consist of the amino acid sequence of SEQ ID NO: 9, SEQ ID NO: 10, or SEQ ID NO: 11. Also preferred is an antibody or antibody fragment (e.g., a heavy chain variable region of an antibody or antibody fragment that comprises, consists essentially of, or consists of the amino acid sequence of SEQ ID NO: 23 or SEQ ID NO: 24 (e.g., SEQ ID NO: 25 or SEQ ID NO: 26).

The invention provides an IL-1β binding antibody or IL-1β binding fragment thereof comprising a heavy chain variable region comprising one of the amino acid sequences of SEQ ID NO: 2, 23 or 24, alternatively one of the amino acid sequence of SEQ ID NO: 12, 13, 21, 23 or 24, or alternatively the amino acid sequence of SEQ ID NO: 12, 13 or 21, or alternatively the amino acid sequence of SEQ ID NO: 13 or 21, or alternatively the amino acid sequence of SEQ ID NO: 8, 14 or 15, or alternatively the amino acid sequence of SEQ ID NO: 8 or 15. Typically, the antibody or antibody fragment comprises a light chain variable region, preferably comprising of the amino acid sequence of SEQ ID NO: 9, SEQ ID NO: 10, or SEQ ID NO: 11. As one example, a preferred antibody comprises a heavy chain variable region comprising the amino acid sequence of SEQ ID NO: 8 and a light chain variable region comprising the amino acid sequence of SEQ ID NO: 11.

The invention also provides an IL-1β binding antibody or IL-1β binding fragment thereof comprising one of the amino acid sequences of SEQ ID NO: 28. Preferably, the antibody or fragment further comprises one of the amino acid sequences of SEQ ID NO: 27.

The invention also provides an IL-1β binding antibody or IL-1β binding fragment thereof comprising, consists essentially of, or consists of SEQ ID NO: 29. Preferably, the antibody or antibody fragment comprises, consists essentially of, or consists of the amino acid sequence of SEQ ID NO: 31-35, or alternatively the amino acid sequence of SEQ ID NO: 31, 32 or 33, or alternatively the amino acid sequence of SEQ ID NO: 32 or 33. Preferably, the antibody or antibody fragment further comprises a light chain variable region comprising one of the amino acid sequences of SEQ ID NO: 27, alternatively one of the amino acid sequences of SEQ ID NO: 9, SEQ ID NO: 10, or SEQ ID NO: 11.

FIGS. 2, 3, and 4 set forth the heavy and light chain variable regions of exemplary antibodies of the invention, which sequences correspond to antibodies referred to herein as AB1, AB2, AB3, AB4, AB5, AB5.1, AB5.2, AB5.3, and AB5.4. The AB5.1, AB5.2, AB5.3, and AB5.4 sequences contain variable positions, designated as X1 and X2, in the heavy chain CDR3 region. These variable positions can be any of the indicated amino acids. Preferably X1 and X2 are, respectively, alanine and arginine, valine and arginine, phenylalanine and arginine, lysine and lysine, or asparagine and arginine.

AB5.1 comprises a heavy chain variable region comprising the amino acid sequence of SEQ ID NO:12 and a light chain variable region comprising the amino acid sequence of SEQ ID NO:10. AB5.2 comprises a heavy chain variable region comprising the amino acid sequence of SEQ ID NO:13 and a light chain variable region comprising the amino acid sequence of SEQ ID NO:11. AB5.3 comprises a heavy chain variable region comprising the amino acid sequence of SEQ ID NO:23 and a light chain variable region comprising the amino acid sequence of SEQ ID NO:10. AB5.4 comprises a heavy chain variable region comprising the amino acid sequence of SEQ ID NO:24 and a light chain variable region comprising the amino acid sequence of SEQ ID NO:11.

The present invention encompasses IL-1β binding antibody fragments comprising any of the foregoing heavy or light chain sequences and which bind IL-1β. The term fragments as used herein refers to any 3 or more contiguous amino acids (e.g., 4 or more, 5 or more 6 or more, 8 or more, or even 10 or more contiguous amino acids) of the antibody and encompasses Fab, Fab', F(ab')$_2$, and F(v) fragments, or the individual light or heavy chain variable regions or portion thereof. IL-1β binding fragments include, for example, Fab, Fab', F(ab')$_2$, Fv and scFv. These fragments lack the Fc fragment of an intact antibody, clear more rapidly from the circulation, and can have less non-specific tissue binding than an intact antibody. See Wahl et al. (1983), J. Nucl. Med., 24: 316-25. These fragments can be produced from intact antibodies using well known methods, for example by proteolytic cleavage with enzymes such as papain (to produce Fab fragments) or pepsin (to produce F(ab')$_2$ fragments).

Figure 19:
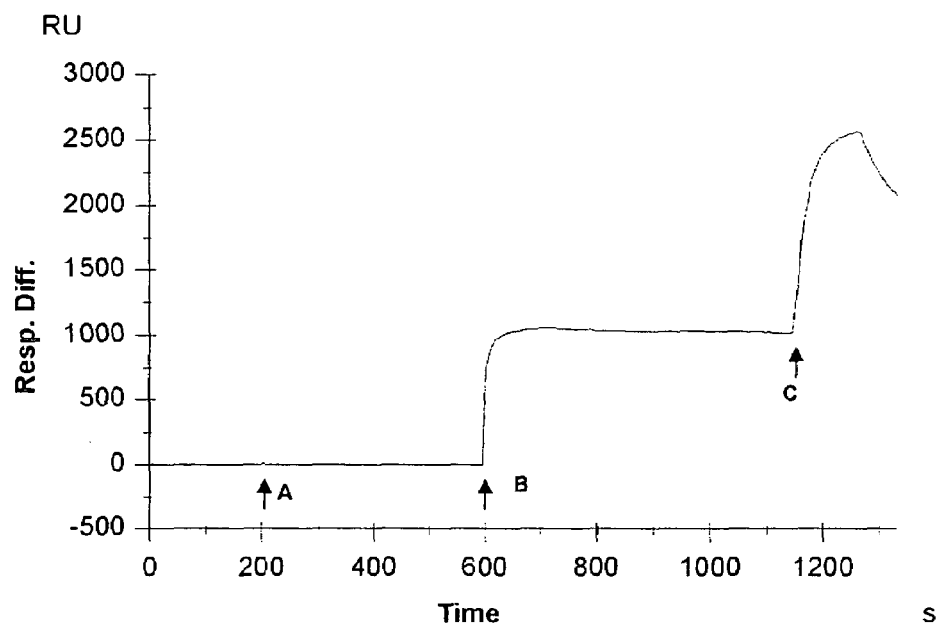
FIG. 19 is a graph showing the results of an assay to examine whether the present antibodies prevent IL-1β from binding to IL-1 receptor type I.
Figure 20:
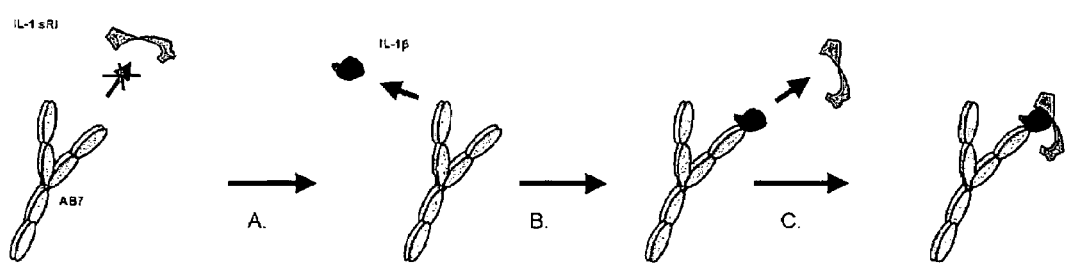
FIG. 20 is an illustration of an assay to examine whether the present antibodies prevent IL-1β from binding to IL-1 receptor type I.

The present invention encompasses IL-1β binding antibodies and IL-1β binding fragments thereof that selectively bind to the IL-1β ligand, but permit or substantially permit the binding of the bound IL-1β ligand to IL-1 receptor type I (IL-1RI) (see Example 14 and FIGS. 19 and 20). In contrast to many antibodies, including several known IL-1β binding antibodies, the antibodies designated AB5 and AB7 selectively bind to the IL-1β ligand, but they do not block or substantially block the binding of IL-1β to IL-1RI, as demonstrated in Example 14. For example, the antibody designated AB7 binds to an IL-1β epitope but still permits the bound IL-1β to binds to IL-1RI. Thus, the present invention encompasses IL-1β binding antibodies or fragments that bind to an IL-1β epitope such that the bound antibody or fragment permits or substantially permits the IL-1β from binding to IL-1 receptor I (IL-1RI), and the antibody or fragment binds to human IL-1β with a dissociation constant less than 3 pM.

In vitro and cell based assays are well described in the art for use in determining binding of IL-1β to IL-1 receptor type I, including assays that determining in the presence of molecules (such as antibodies, antagonists, or other inhibitors) that bind to IL-1β or IL-1RI. (see for example Evans et al., (1995), J. Biol. Chem. 270:11477-11483; Vigers et al., (2000), J. Biol. Chem. 275:36927-36933; Yanofsky et al., (1996), Proc. Natl. Acad. Sci. USA 93:7381-7386; Fredericks et al., (2004), Protein Eng. Des. Sel. 17:95-106; Slack et al., (1993), J. Biol. Chem. 268:2513-2524; Smith et al., (2003), Immunity 18:87-96; Vigers et al., (1997), Nature 386:190-194; Ruggiero et al., (1997), J. Immunol. 158:3881-3887; Guo et al., (1995), J. Biol. Chem. 270:27562-27568; Svenson et al., (1995), Eur. J. Immunol. 25:2842-2850; Arend et al., (1994), J. Immunol. 153:4766-4774). Recombinant IL-1 receptor type I, including human IL-1 receptor type I, for such assays is readily available from a variety of commercial sources (see for example R&D Systems, SIGMA). IL-1 receptor type I also can be expressed from an expression construct or vector introduced into an appropriate host cell using standard molecular biology and transfection techniques known in the art. The expressed IL-1 receptor type I may then be isolated and purified for use in binding assays, or alternatively used directly in a cell associated form.

For example, the binding of IL-1β to IL-1 receptor type I may be determined by immobilizing an IL-1β binding antibody, contacting IL-1β with the immobilized antibody and determining whether the IL-1β was bound to the antibody, and contacting a soluble form of IL-1RI with the bound IL-1β antibody complex and determining whether the soluble IL-1RI was bound to the complex. The protocol may also include contacting the soluble IL-1RI with the immobilized antibody before the contact with IL-1β, to confirm that the soluble IL-1RI does not bind to the immobilized antibody. This protocol can be performed using a Biacore® instrument for kinetic analysis of binding interactions. Such a protocol can also be employed to determine whether an antibody or other molecule permits or blocks the binding of IL-1β to IL-1 receptor type I.

For other IL-1β/IL-1RI binding assays, the permitting or blocking of IL-1β binding to IL-1 receptor type I may be determined by comparing the binding of IL-1β to IL-1RI in the presence or absence of IL-1β antibodies or IL-1β binding fragments thereof. Blocking is identified in the assay readout as a designated reduction of IL-1β binding to IL-1 receptor type I in the presence of anti-IL-1β antibodies or IL-1β binding fragments thereof, as compared to a control sample that contains the corresponding buffer or diluent but not an IL-1β antibody or IL-1β binding fragment thereof. The assay readout may be qualitatively viewed as indicating the presence or absence of blocking, or may be quantitatively viewed as indicating a percent or fold reduction in binding due to the presence of the antibody or fragment.

Alternatively or additionally, when an IL-1β binding antibody or IL-1β binding fragment substantially blocks IL-1β binding to IL1RI, the IL-1β binding to IL1RI is reduced by at least 10-fold, alternatively at least about 20-fold, alternatively at least about 50-fold, alternatively at least about 100-fold, alternatively at least about 1000-fold, alternatively at least about 10000-fold, or more, compared to binding of the same concentrations of IL-1β and IL1RI in the absence of the antibody or fragment. As another example, when an IL-1β binding antibody or IL-1β binding fragment substantially permits IL-1β binding to IL1RI, the IL-1β binding to IL1RI is at least about 90%, alternatively at least about 95%, alternatively at least about 99%, alternatively at least about 99.9%, alternatively at least about 99.99%, alternatively at least about 99.999%, alternatively at least about 99.9999%, alternatively substantially identical to binding of the same concentrations of IL-1β and IL1RI in the absence of the antibody or fragment.

The present invention encompasses IL-1β binding antibodies or IL-1β binding fragments that bind to the same epitope or substantially the same epitope as one or more of the exemplary antibodies described herein. Alternatively or additionally, the IL-1β binding antibodies or IL-1β binding fragments compete with the binding of an antibody having the light chain variable region of SEQ ID NO:11 and the heavy chain variable region of SEQ ID NO:15. Alternatively or additionally, the present invention encompasses IL-1β binding antibodies and fragments that bind to an epitope contained in the amino acid sequence ESVDPKNYPKKKMEKRFVFNKIE (SEQ ID NO:36), an epitope that the antibodies designated AB5 and AB7 bind to. As contemplated herein, one can readily determine if an IL-1β binding antibody or fragment binds to the same epitope or substantially the same epitope as one or more of the exemplary antibodies, such as for example the antibody designated AB7, using any of several known methods in the art.

For example, the key amino acid residues (epitope) bound by an IL-1β binding antibody or fragment may be determined using a peptide array similar to the method described in Example 11. A peptide array, such as for example, a PepSpot™ peptide array (JPT Peptide Technologies, Berlin, Germany), wherein a scan of twelve amino-acid peptides, spanning the entire IL-1β amino acid sequence, each peptide overlapping by 11 amino acid to the previous one, is synthesized directly on a membrane. The membrane carrying the peptides is then probed with the antibody for which epitope binding information is sought, for example at a concentration of 2 μg/ml, for 2 hr at room temperature. Binding of antibody to membrane bound peptides may be detected using a secondary HRP-conjugated goat anti-human (or mouse, when appropriate) antibody, followed by enhanced chemiluminescence (ECL). The peptides spot(s) corresponding to particular amino acid residues or sequences of the mature IL-1β protein, and which score positive for antibody binding, are indicative of the epitope bound by the particular antibody.

Alternatively or in addition, antibody competition experiments may be performed and such assays are well known in the art. For example, to determine if an antibody or fragment binds to an epitope contained in a peptide sequence comprising the amino acids ESVDPKNYPKKKMEKRFVFNKIE, which corresponds to residues 83-105 of the mature IL-1β protein, an antibody of unknown specificity may be compared with any of the exemplary of antibodies (e.g., AB7) of the present invention that are known to bind an epitope contained within this sequence. Binding competition assays may be performed, for example, using a Biacore® instrument for kinetic analysis of binding interactions or by ELISA. In such an assay, the antibody of unknown epitope specificity is evaluated for its ability to compete for binding against the known comparator antibody (e.g., AB7). Competition for binding to a particular epitope is determined by a reduction in binding to the IL-1β epitope of at least about 50%, or at least about 70%, or at least about 80%, or at least about 90%, or at least about 95%, or at least about 99% or about 100% for the known comparator antibody (e.g., AB7) and is indicative of binding to substantially the same epitope.

In view of the identification in this disclosure of IL-1β binding regions in exemplary antibodies and/or epitopes recognized by the disclosed antibodies, it is contemplated that additional antibodies with similar binding characteristics and therapeutic or diagnostic utility can be generated that parallel the embodiments of this disclosure.

Furthermore, the IL-1β antibodies and fragments of the present invention encompass any of the foregoing amino acid sequences of the light or heavy chains with one or more conservative substitutions (e.g., 1, 2, 3, 4, 5, 6, 7, 8, 9, 10, 11, 12, 13, 14, or 15 conservative substitutions). In light of the present disclosure, one can determine the positions of an amino acid sequence that are candidates for conservative substitutions, and one can select synthetic and naturally-occurring amino acids that effect conservative substitutions for any particular amino acids. Consideration for selecting conservative substitutions include the context in which any particular amino acid substitution is made, the hydrophobicity or polarity of the side-chain, the general size of the side chain, and the pK value of side-chains with acidic or basic character under physiological conditions. For example, lysine, arginine, and histidine are often suitably substituted for each other. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine, and tryptophan; and the group consisting of serine, threonine, and, optionally, tyrosine.

By making conservative modifications to the amino acid sequence or corresponding modifications to the encoding nucleotides, one can produce IL-1β binding antibodies or IL-1β binding fragments having functional and chemical characteristics similar to those of the exemplary antibodies and fragments disclosed herein. In contrast, substantial modifications in the functional and/or chemical characteristics of IL-1β binding antibodies or IL-1β binding fragments may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

Antigen-binding fragments of an antibody include fragments that retain the ability to specifically bind to an antigen, generally by retaining the antigen-binding portion of the antibody. It is well established that the antigen-binding function of an antibody can be performed by fragments of a full-length antibody. Examples of antigen-binding portions include (i) a Fab fragment, which is a monovalent fragment consisting of the VL, VH, CL and CH1 domains; (ii) a F(ab')$_2$ fragment, which is a bivalent fragment comprising two Fab fragments linked by a disulfide bridge at the hinge region; (iii) a Fd fragment which is the VH and CH1 domains; (iv) a Fv fragment which is the VL and VH domains of a single arm of an antibody, (v) a dAb fragment (Ward et al., (1989) Nature 341:544-546), which is a VH domain; and (vi) an isolated complementarity determining region (CDR). Single chain antibodies are also encompassed within the term antigen-binding portion of an antibody. The IL-1β binding antibodies and fragments of the present invention also encompass monovalent or multivalent, or monomeric or multimeric (e.g. tetrameric), CDR-derived binding domains with or without a scaffold (for example, protein or carbohydrate scaffolding).

The present IL-1β binding antibodies or fragments may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibodies and fragments comprising immunoadhesion molecules can be obtained using standard recombinant DNA techniques, as described herein. Preferred antigen binding portions are complete domains or pairs of complete domains.

The IL-1β binding antibodies and fragments of the present invention also encompass domain antibody (dAb) fragments (Ward et al., Nature 341:544-546, 1989) which consist of a $V_H$ domain. The IL-1β binding antibodies and fragments of the present invention also encompass diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

The IL-1β binding antibodies and fragments of the present invention also encompass single-chain antibody fragments (scFv) that bind to IL-1β. An scFv comprises an antibody heavy chain variable region ($V_H$) operably linked to an antibody light chain variable region ($V_L$) wherein the heavy chain variable region and the light chain variable region, together or individually, form a binding site that binds IL-1β. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

An scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in an scFv comprises the 5 amino acid sequence Gly-Gly-Gly-Gly-Ser (SEQ ID NO:37). Other examples comprise one or more tandem repeats of this sequence (for example, a polypeptide comprising two to four repeats of Gly-Gly-Gly-Gly-Ser (SEQ ID NO:37)) to create linkers.

The IL-1β binding antibodies and fragments of the present invention also encompass heavy chain antibodies (HCAb). Exceptions to the $H_2L_2$ structure of conventional antibodies occur in some isotypes of the immunoglobulins found in camelids (camels, dromedaries and llamas; Hamers-Casterman et al., 1993 Nature 363: 446; Nguyen et al., 1998 J. Mol. Biol. 275: 413), wobbegong sharks (Nuttall et al., Mol. Immunol. 38:313-26, 2001), nurse sharks (Greenberg et al., Nature 374:168-73, 1995; Roux et al., 1998 Proc. Nat. Acad. Sci. USA 95: 11804), and in the spotted ratfish (Nguyen, et al., "Heavy-chain antibodies in Camelidae; a case of evolutionary innovation," 2002 Immunogenetics 54(1): 39-47). These antibodies can apparently form antigen-binding regions using only heavy chain variable region, in that these functional antibodies are dimers of heavy chains only (referred to as "heavy-chain antibodies" or "HCAbs"). Accordingly, some embodiments of the present IL-1β binding antibodies and fragments may be heavy chain antibodies (HCAb) that specifically bind to IL-1β. For example, heavy chain antibodies that are a class of IgG and devoid of light chains are produced by animals of the genus Camelidae which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$. Muyldermans et al., J. Mol. Recognit. 12:131-140 (1999). The variable domain of the heavy-chain antibodies is sometimes referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999); Woolven et al., Immunogenetics 50:98-101 (1999)). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al., Immunogenetics 54:39-47 (2002). Sharks, including the nurse shark, display similar antigen receptor-containing single monomeric V-domains. Irving et al., J. Immunol. Methods 248:31-45 (2001); Roux et al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., J. Biol. Chem. 276:26285-90, 2001), with $V_{HH}$ affinities typically in the nanomolar range and comparable with those of Fab and scFv fragments. $V_{HH}$s are highly soluble and more stable than the corresponding derivatives of scFv and Fab fragments. $V_H$ fragments have been relatively difficult to produce in soluble form, but improvements in solubility and specific binding can be obtained when framework residues are altered to be more $V_{HH}$-like. (See, for example, Reichman et al., J Immunol Methods 1999, 231:25-38.) $V_{HH}$s carry amino acid substitutions that make them more hydrophilic and prevent prolonged interaction with BiP (Immunoglobulin heavy-chain binding protein), which normally binds to the H-chain in the Endoplasmic Reticulum (ER) during folding and assembly, until it is displaced by the L-chain. Because of the $V_{HH}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient compared to Fabs or scFvs, since only one domain needs to be cloned and expressed to obtain a functional antigen-binding fragment. Muyldermans, Biotechnol. 74:277-302 (2001); Ghahroudi et al., FEBS Lett. 414:521-526 (1997); and van der Linden et al., J. Biotechnol. 80:261-270 (2000). Methods for generating antibodies having camelid heavy chains are also described in U.S. Patent Publication Nos. 20050136049 and 20050037421.

Ribosome display methods may be used to identify and isolate scFv and/or $V_{HH}$ molecules having the desired binding activity and affinity. Irving et al., J. Immunol. Methods 248: 31-45 (2001). Ribosome display and selection has the potential to generate and display large libraries ($10^{14}$).

Other embodiments provide $V_{HH}$-like molecules generated through the process of camelisation, by modifying non-*Camelidae* $V_H$s, such as human $V_{HH}$s, to improve their solubility and prevent non-specific binding. This is achieved by replacing residues on the $V_L$ side of $V_H$s with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic applications. Davies et al., FEBS Lett. 339:285-290 (1994); Davies et al., Protein Eng. 9:531-537 (1996); Tanha et al., J. Biol. Chem. 276:24774-24780 (2001); and Riechmann et al., Immunol. Methods 231:25-38 (1999).

A wide variety of expression systems are available for the production of IL-1β fragments including Fab fragments, scFv, and $V_{HH}$s. For example, expression systems of both prokaryotic and eukaryotic origin may be used for the large-scale production of antibody fragments and antibody fusion proteins. Particularly advantageous are expression systems that permit the secretion of large amounts of antibody fragments into the culture medium.

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab. A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med. Hypotheses.* 64:1105-8, 2005).

The IL-1β binding antibodies and fragments of the present invention also encompass antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

The IL-1β binding antibodies and fragments of the present invention also encompass immunoadhesins. One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs disclosed herein permit the immunoadhesin to specifically bind to IL-1α.

The IL-1β binding antibodies and fragments of the present invention also encompass antibody mimics comprising one or more IL-1β binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties. (Tramontano et al., J. Mol. Recognit. 7:9, 1994; McConnell and Hoess, J. Mol. Biol. 250:460, 1995). Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995). Methods for employing scaffolds for antibody mimics are disclosed in U.S. Pat. No. 5,770,380 and US Patent Publications 2004/0171116, 2004/0266993, and 2005/0038229.

Thus, a variety of IL-1β binding antibodies and fragments comprising one, two, and/or three CDRs of a heavy chain variable region or a light chain variable region of an antibody (preferably one or more of the CDRs of SEQ ID NOS: 1-26) may be generated.

Preferred antibodies or fragments of the present invention bind to IL-1β with (i) an $IC_{50}$ of about 0.5 nM or less (e.g., about 0.4 or less, about 0.3 or less, or even about 0.2 or less), as determined by enzyme linked immunosorbent assay (ELISA), (ii) at least about 100 times (e.g., at least about 150 times, at least about 200 times, or even at least about 250 times) greater affinity relative to its binding of IL-1α (i.e., has a selectivity for IL-1β over IL-1α of at least about 100 times (e.g., at least about 150 times, at least about 200 times, or even at least about 250 times)), and/or (iii) an equilibrium binding dissociation constant ($K_D$) for IL-1β of about 20 pM or less (e.g., about 15 pM or less, about 10 pM or less, or even about 5 pM or less). Also preferred are antibodies or fragments of the invention that can inhibit IL-1β induced expression of serum IL-6 in an animal by at least 50% (e.g., at least 60%, at least 70%, or even at least 80%) as compared to the level of serum IL-6 in an IL-1β stimulated animal that has not been administered an antibody or fragment of the invention. Accordingly, the invention provides, in a related aspect, an IL-1β binding antibody or IL-1β binding antibody fragment that has at least one of the aforementioned characteristics.

Although the invention has been described herein with respect to IL-1β binding antibodies and fragments thereof (e.g., comprising a light and heavy chain), the invention also provides polypeptides other than IL-1β binding antibodies or antibody fragments, such as single-chain polypeptides (including fusion polypeptides, chimeric polypeptides, conjugates and the like). Thus, the invention provides, in this regard, a polypeptide comprising an amino acid sequence of any of SEQ ID NOS: 1-26, or a functionally equivalent fragment or variant thereof. The invention also provides a polypeptide comprising an amino acid sequence of any of SEQ ID NOS: 27-35 or 42-57, or a functionally equivalent fragment or variant thereof.

The antibodies and antibody fragments described herein can be prepared by any suitable method. Suitable methods for preparing such antibodies and antibody fragments are known in the art. Other methods for preparing the antibodies and antibody fragments are as described herein as part of the invention. The antibody, antibody fragment, or polypeptide of the invention, as described herein, can be isolated or purified to any degree. As used herein, an isolated compound is a compound that has been removed from its natural environment. A purified compound is a compound that has been increased in purity, such that the compound exists in a form that is more pure than it exists (i) in its natural environment or (ii) when initially synthesized and/or amplified under laboratory conditions, wherein "purity" is a relative term and does not necessarily mean "absolute purity."

Any of the foregoing antibodies, antibody fragments, or polypeptides of the invention can be humanized or human engineered, as described herein.

Methods of Preparing IL-1β Antibodies or Fragments

The invention provides a method of preparing an affinity matured IL-1β binding polypeptide, such as an antibody or antibody fragment (including an antibody region (e.g., a light or heavy chain variable region or any part thereof, such as a CDR)), which method comprises (a) providing a first nucleic acid comprising a nucleic acid sequence encoding an IL-1β binding polypeptide that comprises the amino acid sequence of any of SEQ ID NOs: 1-26 and a second nucleic acid comprising a nucleic acid sequence that differs from the first nucleic acid sequence by at least one nucleotide, (b) performing nucleic acid shuffling to provide two or more mutated nucleic acids, and (c) selecting for a mutated nucleic acid that encodes a polypeptide that either (i) binds to IL-1β with a greater affinity than the polypeptide encoded by the first nucleic acid, (ii) has a selectivity for IL-1β over IL-1α that is greater than that of the polypeptide encoded by the first nucleic acid, (iii) has an equilibrium binding dissociation constant ($K_D$) for IL-1β that is lower than that of the polypeptide encoded by the first nucleic acid, or (iv) inhibits IL-1β induced expression of serum IL-6 in an animal to a greater degree than the polypeptide encoded by the first nucleic acid, and (d) expressing the selected mutated nucleic acid to provide an affinity matured IL-1β polypeptide. Preferably, the polypeptide is an antibody or antibody fragment, such as any antibody or antibody fragment described herein as part of the invention.

The method of preparing an affinity matured IL-1β polypeptide optionally further comprises repeating steps (b) and (c) one or more times, wherein the nucleic acid shuffling of step (b) is performed using (i) at least one selected mutated nucleic acid of step (c) and (ii) at least one nucleic acid having a nucleic acid sequence that differs from the selected mutated nucleic acid by at least one nucleotide. Preferably, steps (b) and (c) are repeated until an optimized nucleic acid is selected. An optimized nucleic acid is selected when it is no longer possible to select a nucleic acid encoding a polypeptide that has binding characteristics with respect to IL-1β (e.g., characteristics (i)-(iv) of step (c)) that are superior to those of a polypeptide encoded by a nucleic acid previously selected.

Desirably, steps (b) and (c) are repeated until a nucleic acid is selected that encodes a polypeptide having at least one of the following properties: (i) binds to IL-1β with an $IC_{50}$ of about 0.5 nM or less (e.g., about 0.4 or less, about 0.3 or less, or even about 0.2 or less), as determined by enzyme linked immunosorbent assay (ELISA), (ii) binds to IL-1β with at least about 100 times (e.g., at least about 150 times, at least about 200 times, or even at least about 250 times) greater affinity relative to its binding of IL-1β (i.e., has a selectivity for IL-1β over IL-1α of at least about 100 times (e.g., at least about 150 times, at least about 200 times, or even at least about 250 times)), (iii) binds to IL-1β with an equilibrium binding dissociation constant ($K_D$) for IL-1β of about 20 pM or less (e.g., about 15 pM or less, about 10 pM or less, 5 pM or less, 3 pM or less, 2 pM or less, 1 pm or less, 0.7 pM or less, 0.5 pM or less, 0.3 pM or less, or 0.2 pM or less), or (iv) inhibits IL-1β induced expression of serum IL-6 in an animal by at least 50% (e.g., at least 60%, at least 70%, or even at least 80%) as compared to the level of serum IL-6 in an IL-1β stimulated animal that has not been administered an antibody or fragment of the invention.

Selecting for a mutated nucleic acid that encodes a polypeptide having the desired properties can be performed by any suitable method. Procedures for expressing encoded polypeptides and assaying the polypeptides for binding affinity, binding selectivity, equilibrium binding constants, and inhibition of IL-1β induced IL-6 expression are disclosed herein (see Examples). Other suitable methods are known in the art. When the polypeptide encoded by the mutated nucleic acid provided by step (b) is not an antibody or whole antibody fragment (e.g., Fab), it may be necessary to provide an antibody comprising the polypeptide in order to determine whether the polypeptide meets the selection criteria. Thus, the method of preparing an affinity matured IL-1β polypeptide can further comprise a step of providing an antibody comprising the polypeptide encoded by the mutated nucleic acid, wherein the step of selecting for the mutated nucleic acid encoding a polypeptide having the desired properties is performed by assaying the antibody.

Nucleic acid shuffling, as used herein, means fragmenting two or more nucleic acid sequences to provide a pool of random nucleic acid fragments and reassembling the fragments to create two or more mutated nucleic acids. In this regard, a mutated nucleic acid is merely a nucleic acid that has a nucleic acid sequence that has been changed. Nucleic acid shuffling can be performed by any suitable method. Many suitable methods are known in the art, such as those described in U.S. Pat. Nos. 6,489,145; 6,773,900; 6,764,835; 6,740,506; 6,713,282; 6,713,281; 6,713,279; 6,709,841; 6,696,275; 6,677,115; 6,673,552; 6,656,677; 6,605,449; 6,566,050; 6,562,594; 6,555,315; 6,537,776; 6,528,249; 6,479,258; 6,455,254; 6,440,668; 6,368,798; 6,361,974; 6,358,709; 6,352,842; 6,344,328; 6,335,179; 6,280,926; 6,238,884; 6,174,673; 6,171,820; 6,168,919; 6,057,103; 6,054,267; 6,030,779 6,001,574; 5,965,408; 5,958,672; 5,939,250; 5,763,239; 6,395,547; 6,376,246; 6,372,497; 6,368,861; 6,365,408; 6,365,377; 6,358,740; 6,358,742; 6,355,484; 6,344,356; 6,337,186; 6,335,160; 6,323,030; 6,319,714; 6,319,713; 6,303,344; 6,297,053; 6,291,242; 6,287,861; 6,277,638; 6,180,406; 6,165,793; 6,132,970; 6,117,679; 5,834,252; 5,830,721; 5,811,238; 5,605,793.

Nucleic Acids

The antibodies, antibody fragments, and polypeptides of the invention can be encoded by a single nucleic acid (e.g., a single nucleic acid comprising nucleotide sequences that encode the light and heavy chain polypeptides of the antibody), or by two or more separate nucleic acids, each of which encode a different part of the antibody or antibody fragment. In this regard, the invention provides one or more nucleic acids that encode any of the forgoing antibodies, antibody fragments, or polypeptides (e.g., any of the foregoing light or heavy chain variable regions).

According to one aspect of the invention, the invention provides a nucleic acid that encodes a heavy chain variable region of an antibody or a portion thereof. Exemplary nucleic acid sequences are provided in SEQ ID NOS: 39 and 40, which respectively encode the heavy chain variable region of SEQ ID NO: 15, and the light chain variable region of SEQ ID NO: 11. In this regard, the invention provides a nucleic acid encoding a polypeptide (e.g., a heavy chain variable region of an antibody) comprising the amino acid sequence of SEQ ID NO: 2, alternatively the sequence of SEQ ID NO: 28, and desirably encodes a polypeptide comprising the amino acid sequence of SEQ ID NO: 21 (e.g., a polypeptide comprising the amino acid sequence of any of SEQ ID NOs: 4-8). More preferred are nucleic acid sequences encoding a polypeptide (e.g., a heavy chain variable region) comprising the amino acid sequence of SEQ ID NO: 12 or SEQ ID NO: 13 (e.g., a polypeptide comprising the amino acid sequence of any of SEQ ID NOs: 14-15), or comprising the amino acid sequence of SEQ ID NO: 23 or SEQ ID NO: 24 (e.g., SEQ ID NO: 25 or SEQ ID NO: 26).

Alternatively, or in addition, the nucleic acid of the invention can comprise a nucleic acid sequence that encodes a light chain variable region of an antibody or a portion thereof. In this regard, the invention provides a nucleic acid that encodes a polypeptide (e.g., a light chain variable region) comprising the amino acid sequence of SEQ ID NO: 1. For example, the nucleic acid sequence can encode a polypeptide comprising the amino acid sequence of SEQ ID NO: 9. More preferably, the nucleic acid encodes a polypeptide (e.g., a light chain variable region) that comprises the amino acid sequence of SEQ ID NO: 10 or 11.

Also encompassed by the invention are nucleic acids encoding any of the foregoing amino acid sequences of the light or heavy chains that comprise one or more conservative substitutions (e.g., 1, 2, 3, 4, 5, 6, 7, 8, 9, 10, 11, 12, 13, 14, or 15 conservative substitutions), as discussed with respect to the antibody and antibody fragment of the invention, where the antibody or fragment comprising the substitution has the same or substantially the same affinity and specificity of epitope binding as one or more of the exemplary antibodies, fragments and sequences disclosed herein.

The nucleic acid sequences can be determined from the amino acid sequences of the antibodies, antibody fragments, and light or heavy chain variable regions described herein by any suitable method, such as by converting such amino acid sequences into the corresponding nucleic acid sequences using the genetic code. The nucleic acids encoding those amino acid sequences (such as the amino acid sequences described herein) can be prepared (e.g., the nucleic acid sequences isolated or synthesized) using methods known in the art, such as those described in, for example, Sambrook et al., *Molecular Cloning, a Laboratory Manual*, 3$^{rd}$ edition, Cold Spring Harbor Press, Cold Spring Harbor, N.Y., 2001; Ausubel et al., *Current Protocols in Molecular Biology*, Greene Publishing Associates and John Wiley & Sons, New York, N.Y., 1994; and Herdewijn, ed., *Oligonucleotide Synthesis: Methods and Applications* (*Methods in Molecular Biology*), Humana Press, Totowa, N.J., 2004. The nucleic acids described herein can be isolated or purified to any degree. As used herein, an isolated compound is a compound that has been removed from its natural environment. A purified compound is a compound that has been increased in purity, such that the compound exists in a form that is more pure than it exists (i) in its natural environment or (ii) when initially synthesized and/or amplified under laboratory conditions, wherein "purity" is a relative term and does not necessarily mean "absolute purity."

The nucleic acids can be purified using any of a variety of techniques including, but not limited to preparative gel electrophoresis or isoelectric focusing, affinity, immunoaffinity or ion exchange chromatography, molecular sieve chromatography, chromatofocusing, or high pressure liquid chromatography.

Vectors

The nucleic acids described herein can be inserted into vectors, e.g., nucleic acid expression vectors and/or targeting vectors. Such vectors can be used in various ways, e.g., for the expression of an IL-1β binding antibody or antibody fragment in a cell or transgenic animal. Accordingly, the invention provides a vector comprising any one or more of the nucleic acids of the invention. A "vector" is any molecule or composition that has the ability to carry a nucleic acid sequence into a suitable host cell where synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). Desirably, the vector is comprised of DNA. Examples of suitable DNA-based gene transfer vectors include plasmids and viral vectors. Suitable viral vectors include, for instance, parvoviral-based vectors (e.g., adeno-associated virus (AAV)-based vectors), retroviral vectors, herpes simplex virus (HSV)-based vectors, AAV-adenoviral chimeric vectors, HIV virus-based vectors, and adenovirus-based vectors. Any of these vectors can be prepared using standard recombinant DNA techniques described in, e.g., Sambrook et al., supra, and Ausubel et al., supra. However, vectors that are not based on nucleic acids, such as liposomes, are also known in the art and can be used in connection with the invention. The inventive vector can be based on a single type of nucleic acid (e.g., a plasmid) or non-nucleic acid molecule (e.g., a lipid or a polymer). Alternatively, the vector can be a combination of a nucleic acid and a non-nucleic acid (i.e., a "chimeric" vector). For example, a plasmid harboring the nucleic acid can be formulated with a lipid or a polymer as a delivery vehicle. Such a vector is referred to herein as a "plasmid-lipid complex" and a "plasmid-polymer" complex, respectively. The inventive gene transfer vector can be integrated into the host cell genome or can be present in the host cell in the form of an episome.

Nucleic acids of the invention can be inserted into immunoglobulin expression vectors, for example, the vectors described in McLean et al., *Mol. Immunol.*, 37: 837-45 (2000); Walls et al., *Nucleic Acids Res.*, 21: 2921-9 (1993); and Norderhaug et al., *J. Immunol. Meth.*, 204: 77-87 (1997).

Vectors are typically selected to be functional in the host cell in which the vector will be used (the vector is compatible with the host cell machinery such that amplification of the gene and/or expression of the gene can occur). A nucleic acid molecule encoding an IL-1β binding antibody or fragment may be amplified/expressed in prokaryotic, yeast, insect (baculovirus systems) and/or eukaryotic host cells. Selection of the host cell will depend in part on whether the IL-1β binding antibody or fragment is to be post-transitionally modified (e.g., glycosylated and/or phosphorylated). If so, yeast, insect, or mammalian host cells are preferable. Further information about expression vectors may be found in Meth. Enz. v. 185 (1990; Goeddel, ed.), Academic Press Inc., San Diego, Calif.

Expression vectors typically contain one or more of the following components: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element.

Vector components may be homologous (from the same species and/or strain as the host cell), heterologous (from a species other than the host cell species or strain), hybrid (a combination of different sequences from more than one source), synthetic, or native sequences which normally function to regulate immunoglobulin expression. Sources of vector components can be any prokaryotic or eukaryotic organism, any vertebrate or invertebrate organism, or any plant, provided that the components are functional in, and can be activated by, the host cell machinery.

An origin of replication is selected based upon the type of host cell being used for expression. By way of example, the origin of replication from the plasmid pBR322 (Product No. 303-3s, New England Biolabs, Beverly, Mass.) is useful for most Gram-negative bacteria while various origins from SV40, polyoma, adenovirus, vesicular stomatitis virus (VSV) or papillomaviruses (such as HPV or BPV) are useful for cloning vectors in mammalian cells. Generally, the origin of replication component is not needed for mammalian expression vectors (for example, the SV40 origin is often used because it contains the early promoter).

A transcription termination sequence is typically located 3' of the end of a polypeptide coding regions and serves to terminate transcription. Transcription termination sequences in prokaryotic cells often comprise a G-C rich fragment followed by a poly T sequence. Transcription termination sequences can be cloned from a library, purchased commercially as part of a vector, or synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is a process where genes which are in greater demand for the production of a protein critical for growth are reiterated in tandem within the chromosomes of successive generations of recombinant cells. Examples of selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes an IL-1β antibody or fragment. As a result, increased quantities of an antibody are synthesized from the amplified DNA.

A ribosome binding site is generally present for initiating mRNA translation. For example, such a site is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine (having a high A-G content). Many Shine-Dalgarno sequences have been identified, each of which can be readily synthesized using methods set forth above and used in a prokaryotic vector.

A leader, or signal, sequence may be used to direct secretion of a polypeptide. A signal sequence may be positioned within or directly at the 5' end of a polypeptide coding region. Many signal sequences have been identified and may be selected based upon the host cell used for expression. A signal sequence may be homologous (naturally occurring) or heterologous to a nucleic acid sequence encoding the protein to expressed (such as antibody or antigen binding fragment). A heterologous signal sequence selected should be one that is recognized and processed (cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, or heat-stable enterotoxin II leaders. For yeast secretion, a native antibody signal sequence may be substituted by the yeast invertase, alpha factor, or acid phosphatase leaders. In mammalian cell expression the native signal sequence is generally satisfactory, although other mammalian signal sequences may be suitable.

In most cases, secretion of an antibody or antigen binding fragment from a host cell will result in the removal of the signal peptide from the antibody or fragment. Thus the mature antibody or fragment will lack any leader or signal sequence.

In some cases, such as where glycosylation is desired in a eukaryotic host cell expression system, one may manipulate the various presequences to improve glycosylation or yield. For example, one may alter the peptidase cleavage site of a signal peptide, or add prosequences, which also may affect glycosylation. The final antibody or fragment may have, in the −1 position (relative to the first amino acid of the mature protein) one or more additional amino acids incident to expression, which may not have been totally removed. For example, the final antibody or fragment may have one or two amino acid found in the peptidase cleavage site, attached to the N-terminus. Alternatively, use of some enzyme cleavage sites may result in a slightly truncated form of the desired antibody or fragment, if the enzyme cuts at such area within the mature antibody or fragment.

The expression vectors will typically contain a promoter that is recognized by the host organism and operably linked to a nucleic acid molecule encoding an IL-1β binding antibody or antigen binding fragment. Either a native or heterologous promoter may be used depending the host cell used for expression and the yield desired.

Promoters for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, and they can be ligated to a desired nucleic acid sequence(s), using linkers or adapters as desired to supply restriction sites.

Promoters for use with yeast hosts are also known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be used for expressing the selective binding agents of the invention include, but are not limited to: the SV40 early promoter region (Bernoist and Chambon, Nature, 290:304-310, 1981); the CMV promoter; the promoter contained in the 3' long terminal repeat of Rous sarcoma virus (Yamamoto et al. (1980), Cell 22: 787-97); the herpes thymidine kinase promoter (Wagner et al. (1981), Proc. Natl. Acad. Sci. U.S.A. 78: 1444-5); the regulatory sequences of the metallothionine gene (Brinster et al, Nature, 296; 39-42, 1982); prokaryotic expression vectors such as the beta-lactamase promoter (Villa-Kamaroff, et al., Proc. Natl. Acad. Sci. U.S.A., 75; 3727-3731, 1978); or the tac promoter (DeBoer, et al. (1983), Proc. Natl. Acad. Sci. U.S.A., 80: 21-5). Also of interest are the following animal transcriptional control regions, which exhibit tissue specificity and have been utilized in transgenic animals: the elastase I gene control region which is active in pancreatic acinar cells (Swift et al. (1984), Cell 38: 639-46; Ornitz et al. (1986), Cold Spring Harbor Symp. Quant. Biol. 50: 399-409; MacDonald (1987), Hepatology 7: 425-515); the insulin gene control region which is active in pancreatic beta cells (Hanahan (1985), Nature 315: 115-22); the immunoglobulin gene control region which is active in lymphoid cells (Grosschedl et al. (1984), Cell 38; 647-58; Adames et al. (1985), Nature 318; 533-8; Alexander et al. (1987), Mol. Cell. Biol. 7: 1436-44); the mouse mammary tumor virus control region which is active in testicular, breast, lymphoid and mast cells (Leder et al. (1986), Cell 45: 485-95), albumin gene control region which is active in liver (Pinkert et al. (1987), Genes and Devel. 1: 268-76); the alphafetoprotein gene control region which is active in liver (Krumlauf et al. (1985), Mol. Cell. Biol. 5: 1639-48; Hammer et al. (1987), Science, 235: 53-8); the alpha 1-antitrypsin gene control region which is active in the liver (Kelsey et al. (1987), Genes and Devel. 1: 161-71); the beta-globin gene control region which is active in myeloid cells (Mogram et al., Nature, 315 338-340, 1985; Kollias et al. (1986), Cell 46: 89-94); the myelin basic protein gene control region which is active in oligodendrocyte cells in the brain (Readhead et al. (1987), Cell, 48: 703-12); the myosin light chain-2 gene control region which is active in skeletal muscle (Sani (1985), Nature, 314: 283-6); and the gonadotropic releasing hormone gene control region which is active in the hypothalamus (Mason et al. (1986), Science 234: 1372-8).

An enhancer sequence may be inserted into the vector to increase transcription in eucaryotic host cells. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters.

While an enhancer may be spliced into the vector at a position 5' or 3' to the polypeptide coding region, it is typically located at a site 5' from the promoter.

Vectors for expressing nucleic acids include those which are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (Blue-BacII; Invitrogen), pDSR-alpha (PCT Publication No. WO90/14363) and pFastBacDual (Gibco/BRL, Grand Island, N.Y.).

Additional possible vectors include, but are not limited to, cosmids, plasmids or modified viruses, but the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™. TA Cloning® Kit, PCR2.1 plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

Host Cells and Uses Thereof

The invention further provides a cell (e.g., an isolated or purified cell) comprising a nucleic acid or vector of the invention. The cell can be any type of cell capable of being transformed with the nucleic acid or vector of the invention so as to produce a polypeptide encoded thereby. The cell is preferably the cell of a mammal, such as a human, and is more preferably a hybridoma cell, an embryonic stem cell, or a fertilized egg.

To express the IL-1β binding or fragment, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the light or heavy chain sequences, the expression vector may already carry antibody constant region sequences. For example, one approach to converting the selected VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. The term regulatory sequence is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated that the design of the expression vector, including the selection of regulatory sequences may depend on such factors as the choice of the host cell to be transformed, the level of expression of protein desired, as well as other considerations. Preferred regulatory sequences for mammalian host cell expression include viral elements that direct high levels of protein expression in mammalian cells.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Methods of introducing nucleic acids and vectors into isolated cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra; Davis et al., *Basic Methods in Molecular Biology*, $2^{nd}$ ed., McGraw-Hill Professional, 1995; and Neumann et al., *EMBO J.*, 1: 841 (1982)).

The cell comprising the nucleic acid or vector of the invention can be used to produce the IL-1β binding antibody, fragment thereof, or a portion thereof (e.g., a heavy chain sequence, or a light chain sequence encoded by the nucleic acid or vector). After introducing the nucleic acid or vector of the invention into the cell, the cell is cultured under conditions suitable for expression of the encoded sequence. The antibody, antigen binding fragment, or portion of the antibody then can be isolated from the cell.

In certain embodiments, two or more vectors that together encode an IL-1β binding antibody, or antigen binding fragment thereof, can be introduced into the cell. For example, a first vector encoding a heavy chain variable region or a complete heavy chain sequence can be introduced to a host cell, and a second vector encoding a light chain variable region or complete light chain sequence also is introduced to the host cell. The cell is then cultured under conditions suitable for expression of the two sequences encoded by the first and second vectors, and the encoded polypeptides can be isolated from the host cell. If necessary, the isolated polypeptides then can be combined under conditions that promote their association and organization into an IL-1β binding antibody or antigen binding fragment thereof. Alternatively, the first and second vectors can be introduced into separate cells, and the products can be isolated from the respective cells and combined to provide an IL-1β binding antibody or antigen binding fragment thereof. Methods for promoting the association and organization of antibody constituents into antigen-binding polypeptides have been described in the art. Similarly, methods for isolating an antibody, antigen binding fragment thereof, or heavy chain and light chain fragments are known to ordinarily skilled artisans.

Embryonic stem cells or fertilized eggs that comprise a nucleic acid or vector of the invention can be used to generate a transgenic non-human animal. Methods for making transgenic animals are described in Hofker et al., *Transgenic Mouse. Methods and Portocols* (Methods in Molecular Biology), Humana Press, Clifton, N.J., 2002. Transgenic non-human animals that comprise a nucleic acid or vector disclosed herein can be used to express the encoded antibody, antigen binding fragment, or portion of the antibody. The antibody, antigen binding fragment, or portion then can be isolated from the animal. Portions of an antibody can subsequently be reconstituted (in combination with additional antibody portions) into an IL-1β binding antibody or antibody fragment of the invention.

The host cells may be prokaryotic host cells (such as *E. coli*) or eukaryotic host cells (such as a yeast cell, an insect cell, or a vertebrate cell). The host cell, when cultured under appropriate conditions, expresses an IL-1β binding antibody or fragment which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule. A number of suitable host cells are known in the art and many are available from the American Type Culture Collection (ATCC), Manassas, Va. Examples include mammalian cells, such as Chinese hamster ovary cells (CHO) (ATCC No. CCL61) CHO DHFR-cells (Urlaub et al. Proc. Natl. Acad. Sci. USA 97, 4216-4220

(1980)), human embryonic kidney (HEK) 293 or 293T cells (ATCC No. CRL1573), 3T3 cells (ATCC No. CCL92), or PER.C6 cells. The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines, avian cell lines, and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va.). Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of *B. subtilis*, *Pseudomonas* spp., other *Bacillus* spp., *Streptomyces* spp., and the like may also be employed in this method.

For expression of the light and heavy chains, the expression vector(s) encoding the heavy and light chains is transfected into a host cell by standard techniques. Transfection encompasses a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the IL-1β binding antibodies or fragments in either prokaryotic or eukaryotic host cells, expression of the antibodies or fragments in eukaryotic cells, and most preferably mammalian host cells, is the most preferred because such eukaryotic cells, and in particular mammalian cells, are more likely than prokaryotic cells to assemble and secrete a properly folded and immunologically active antibody. Mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:42164220, used with a DHFR selectable marker, e.g., as described in R. J. Kaufman and P. A. Sharp (1982) Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Many strains of yeast cells known in the art are also available as host cells for expression of the antibodies and fragments. Preferred yeast cells include, for example, *Saccharomyces cerivisae*. Additionally, where desired, insect cell systems may be utilized. Such systems are described for example in Kitts et al. (Biotechniques, 14, 810-817 (1993)), Lucklow (Curr. Opin. Biotechnol., 4, 564-572 (1993) and Lucklow et al. (J. Virol., 67, 4566-4579 (1993)). Preferred insect cells are Sf-9 and Hi5 (Invitrogen, Carlsbad, Calif.).

Transformation or transfection of a nucleic acid molecule encoding an IL-1β binding antibody or fragment into a selected host cell may be accomplished by well known methods including calcium chloride methods, electroporation methods, microinjection methods, lipofection methods or the DEAE-dextran methods. The method selected will in part depend on the type of host cell to be used. These methods and other suitable methods are well known, and are set forth, for example, in Sambrook et al. supra.

Transgenic animals can also be used to express glycosylated antibodies and fragments. For example, one may use a transgenic milk-producing animal (a cow or goat, for example) and obtain glycosylated binding agents in the animal milk. Alternatively, one may use plants to produce glycosylated selective binding agents.

Host cells comprising an expression vector encoding an IL-1β binding antibody or fragment may be cultured using media known in the art. The media will usually contain all nutrients necessary for the growth and survival of the cells. Examples of media for culturing *E. coli* cells include Luria Broth (LB) and/or Terrific Broth (TB). Suitable media for culturing eukaryotic cells are RPMI 1640, MEM, DMEM, which may be supplemented with serum and/or growth factors as desired for the particular cell line being cultured. An exemplary medium for insect cultures is Grace's medium supplemented with yeastolate, lactalbumin hydrolysate, and/or fetal calf serum as necessary.

An antibiotic or other compound useful for selective growth of transfected or transformed cells may be added as a supplement to the media. The compound will be chosen based on the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

The amount of IL-1β binding antibody or fragment produced by a host cell can be evaluated using methods known in the art. Such methods include, without limitation, Western blot analysis, SDS-polyacrylamide gel electrophoresis, non-denaturing gel electrophoresis, HPLC separation, immunoprecipitation, and/or activity assays.

Purification of an IL-1β binding antibody or fragment which has been secreted into the cell media can be accomplished using a variety of techniques including affinity, immunoaffinity or ion exchange chromatography, molecular sieve chromatography, preparative gel electrophoresis or isoelectric focusing, chromatofocusing, and high pressure liquid chromatography. For example, antibodies comprising a Fc region may be purified by affinity chromatography with Protein A, which selectively binds the Fc region. Modified forms of an antibody or antigen binding fragment may be prepared with affinity tags, such as hexahistidine or other small peptide such as FLAG (Eastman Kodak Co., New Haven, Conn.) or myc (Invitrogen) at either its carboxyl or amino terminus and purified by a one-step affinity column. For example, polyhistidine binds with great affinity and specificity to nickel, thus an affinity column of nickel (such as the Qiagen.®. nickel columns) can be used for purification of polyhistidine-tagged selective binding agents. (See for example, Ausubel et al, eds., Current Protocols in Molecular Biology, Section 10.11.8, John Wiley & Sons, New York (1993)). In some instances, more than one purification step may be employed.

IL-1β binding antibodies or fragments which are expressed in procaryotic host cells may be present in soluble form either in the periplasmic space or in the cytoplasm or in an insoluble form as part of intracellular inclusion bodies. IL-1β binding antibodies or fragments can be extracted from the host cell using any appropriate technique known in the art. For example, the host cells can be lysed to release the contents of the periplasm/cytoplasm by French press, homogenization, and/or sonication followed by centrifugation.

Soluble forms of an IL-1β binding antibody or fragment present either in the cytoplasm or released from the periplasmic space may be further purified using methods known in the art, for example Fab fragments are released from the bacterial periplasmic space by osmotic shock techniques.

If inclusion bodies comprising an antibody or fragment have formed, they can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The soluble antibody or fragment can then be analyzed using gel electrophoresis, immunoprecipitation or the like. If it is desired to isolate a solublized antibody or antigen binding fragment isolation may be accomplished using standard methods such as those set forth below and in Marston et al. (Meth. Enz., 182:264-275 (1990)).

In some cases, an IL-1β binding antibody or fragment may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

IL-1β binding antibodies or fragments of the present invention may also be prepared by chemical synthesis methods (such as solid phase peptide synthesis) using techniques known in the art such as those set forth by Merrifield et al. (1963), J. Am. Chem. Soc., 85: 2149, Houghten et al. (1985), Proc Natl Acad. Sci. USA, 82: 5132, and Stewart and Young (1984), Solid Phase Peptide Synthesis, Pierce Chemical Co., Rockford, Ill. Such antibodies or fragments may be synthesized with or without a methionine on the amino terminus. Chemically synthesized antibodies and antigen binding fragments may be oxidized using methods set forth in these references to form disulfide bridges. Antibodies and fragments so prepared will retain at least one biological activity associated with a native or recombinantly produced IL-1β binding antibody or fragment.

Pharmaceutical Compositions

IL-1β binding antibodies, antibody fragments, nucleic acids, or vectors of the invention can be formulated in compositions, especially pharmaceutical compositions. Such compositions comprise a therapeutically or prophylactically effective amount of an IL-1β binding antibody, antibody fragment, nucleic acid, or vector of the invention in admixture with a suitable carrier, e.g., a pharmaceutically acceptable agent. Typically, IL-1β binding antibodies, antibody fragments, nucleic acids, or vectors of the invention are sufficiently purified for administration to an animal before formulation in a pharmaceutical composition.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in *Remington's Pharmaceutical Sciences,* 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly(ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of IL-1β binding antibodies, antibody fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present invention. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see for example, Cortivo et al., Biomaterials (1991) 12:727-730; European Publication No. 517,565; International Publication No. WO 96/29998; Illum et al., J. Controlled Rel. (1994) 29:133-141). Exemplary hyaluronic acid containing compositions of the present invention comprise a hyaluronic acid ester polymer in an amount of approximately 0.1% to about 40% (w/w) of an IL-1β binding antibody or fragment to hyaluronic acid polymer.

Both biodegradable and non-biodegradable polymeric matrices can be used to deliver compositions of the present invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

Alternatively or additionally, the compositions can be administered locally via implantation into the affected area of a membrane, sponge, or other appropriate material on to which an IL-1β binding antibody, antibody fragment, nucleic acid, or vector of the invention has been absorbed or encapsulated. Where an implantation device is used, the device can be implanted into any suitable tissue or organ, and delivery of an IL-1β binding antibody, antibody fragment, nucleic acid, or vector of the invention can be directly through the device via bolus, or via continuous administration, or via catheter using continuous infusion.

A pharmaceutical composition comprising an IL-1β binding antibody, antibody fragment, nucleic acid, or vector of the invention can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 μm to 5 μm; however, larger particles may be used, for example, if each particle is fairly porous.

Certain formulations containing IL-1β binding antibodies, antibody fragments, nucleic acids, or vectors of the invention can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an IL-1β binding antibody, antibody fragment, nucleic acid, or vector of the invention in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

Additional formulations will be evident in light of the present disclosure, including formulations involving IL-1β binding antibodies, antibody fragments, nucleic acids, or vectors of the invention in combination with one or more other therapeutic agents. For example, in some formulations, an IL-1β binding antibody, antibody fragment, nucleic acid, or vector of the invention is formulated with a second inhibitor of an IL-1 signaling pathway Representative second inhibitors include, but are not limited to, antibodies, antibody fragments, peptides, polypeptides, compounds, nucleic acids, vectors and pharmaceutical compositions, such as, for example, those described in U.S. Pat. No. 6,899,878, US 2003022869, US 20060094663, US 20050186615, US 20030166069, WO/04022718, WO/05084696, WO/05019259. For example, a composition may comprise an IL-1β binding antibody, antibody fragment, nucleic acid, or vector of the invention in combination with an IL-1β binding antibody, fragment, or a nucleic acid or vector encoding such an antibody or fragment.

The pharmaceutical compositions can comprise IL-1β binding antibodies or fragments in combination with other active agents. Such combinations are those useful for their intended purpose. The active agents set forth below are illustrative for purposes and not intended to be limited. The combinations which are part of this invention can be the present antibodies and fragments and at least one additional agent selected from the lists below. The combination can also include more than one additional agent, e.g., two or three additional agents if the combination is such that the formed composition can perform its intended function.

Active agents or combinations with the present antibodies or fragments include a non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors. Other active agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies and fragments.

Additional examples of active agents for combinations with IL-1β binding antibodies or fragments for rheumatoid arthritis include cytokine suppressive anti-inflammatory drug(s) (CSAIDs); antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF. The IL-1β binding antibodies and fragments can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD 154 (gp39 or CD40L).

Preferred combinations of active agents may interfere at different points in the autoimmune and subsequent inflammatory cascade; preferred examples include TNF antagonists like chimeric, humanized or human TNF antibodies, D2E7, cA2 (Remicade™), CDP 571, anti-TNF antibody fragments (e.g., CDP870), and soluble p55 or p75 TNF receptors, derivatives thereof, (p75TNFRIgG (Enbrel™) or p55TNFR1gG (Lenercept), soluble IL-13 receptor (sIL-13), and also TNFα converting enzyme (TACE) inhibitors; similarly IL-1 inhibitors (e.g., Interleukin-1-converting enzyme inhibitors, such as Vx740, or IL-1RA etc.) may be effective for the same reason. Other preferred combinations include Interleukin 11, anti-P7s and p-selectin glycoprotein ligand (PSGL). Yet another combination are other key players of the autoimmune response which may act parallel to, dependent on or in concert with IL-1β function.

Active agents for Crohn's disease in which an antibody or an antigen binding portion can be combined include TNF antagonists, for example, anti-TNF antibodies, D2E7, cA2 (Remicade™), CDP 571, anti-TNF antibody fragments (e.g., CDP870), TNFR-Ig constructs (p75TNFRIgG (Enbrel™) and p55TNFRIgG (Lenercept)), anti-P7s, p-selectin glycoprotein ligand (PSGL), soluble IL-13 receptor (sIL-13), and PDE4 inhibitors. The IL-1β binding antibodies or fragments can be combined with corticosteroids, for example, budenoside and dexamethasone. The IL-1β binding antibodies or fragments may also be combined with agents such as sulfasalazine, 5-aminosalicylic acid and olsalazine, and agents which interfere with synthesis or action of proinflammatory cytokines such as IL-1, for example, IL-1 converting enzyme inhibitors (e.g., Vx740) and IL-1ra. The IL-1β binding antibodies or fragments may also be used with T cell signaling inhibitors, for example, tyrosine kinase inhibitors 6-mercaptopurines. The IL-1β binding antibodies or fragments can be combined with IL-11.

Other examples of active agents for multiple sclerosis with which the IL-1β binding antibodies or fragments can be combined include corticosteroids; prednisolone; methylprednisolone; azathioprine; cyclophosphamide; cyclosporine; methotrexate; 4-aminopyridine; tizanidine; interferon-β1a (Avonex; Biogen); interferon-β1b (Betaseron; Chiron/Berlex); Copolymer 1 (Cop-1; Copaxone; Teva Pharmaceutical Industries, Inc.); hyperbaric oxygen; intravenous immunoglobulin; clabribine; antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. The IL-1β binding antibodies or fragments can be combined with antibodies to cell surface molecules such as CD2, CD3, CD4, CD8, CD25, CD28, CD30, CD40, CD45, CD69, CD80, CD86, CD90 or their ligands. The IL-1β binding antibodies or fragments may be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R, soluble IL-13 receptor (sIL-13)) and antiinflammatory cytokines (e.g. IL-4, IL-10, IL-13 and TGFβ).

Preferred examples of active agents for multiple sclerosis in which the IL-1β binding antibodies or fragments can be combined to include interferon-β, for example, IFNβ1a and IFNβ1b; copaxone, corticosteroids, IL-1 inhibitors, TNF inhibitors, and antibodies to CD40 ligand and CD80.

The pharmaceutical compositions may include a therapeutically effective amount or a prophylactically effective amount of the present IL-1β binding antibodies or fragments. A therapeutically effective amount refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A prophylactically effective amount refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

IL-1β binding antibodies, antibody fragments, nucleic acids, or vectors of the invention, can be employed alone or in combination with other active agents, which can be in the same pharmaceutical composition or in a different pharmaceutical composition. For example, such other active agents can comprise (i) IL-1 antagonist (e.g., recombinant IL-1Ra or an IL-trap), (ii) an interleukin-1 receptor antagonist, (iii) a soluble TNF receptor-1, (iv) a soluble TNF receptor-2 (e.g., etanercept), (iv) TNF inhibitor (e.g., an antibody such as D2E7), and/or (v) a cancer therapy agent. Thus, for example, one or more of these components can be included in the composition of the invention with an IL-1β binding antibody, antibody fragment, nucleic acid, or vector of the invention.

It may be desirable in some instances to use a pharmaceutical composition comprising an IL-1β binding antibody, antibody fragment, nucleic acid or vector of the invention in an ex vivo manner. In this case, cells, tissues, or organs that have been removed from a patient are exposed to pharmaceutical compositions comprising an IL-1β binding antibody, antibody fragment, nucleic acid, or vector of the invention, after which the cells, tissues, and/or organs are subsequently implanted back into the patient.

In certain situations, a composition comprising an IL-1β binding antibody, antibody fragment, nucleic acid, or vector can be delivered by implanting into patients cells that have been genetically engineered, as described herein, to express and secrete the polypeptides, selective binding agents, fragments, variants, or derivatives. Such cells may be animal or human cells, and can be derived from the patient's own tissue or from another source, either human or non-human. Optionally, the cells can be immortalized cells. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are known, and the preparation of encapsulated cells and their implantation in patients has been described, for example, in U.S. Pat. Nos. 4,892,538, 5,011,472, and 5,106,627. A system for encapsulating living cells is described in PCT Application Publication WO 91/10425. Techniques for formulating a variety of other sustained or controlled delivery means, such as liposome carriers, bio-erodible particles, or beads, are also known to those in the art, and are described. The cells, with or without encapsulation, can be implanted into suitable body tissues or organs of the patient.

A therapeutically or prophylactically effective amount of a pharmaceutical composition comprising an IL-1β binding antibody, antibody fragment, nucleic acid, or vector of the invention will depend, for example, upon the therapeutic objectives such as the indication for which the composition is being used, the route of administration, and the condition of the subject. Pharmaceutical compositions are administered in a therapeutically or prophylactically effective amount to treat an IL-1 related condition. A "therapeutically or prophylactically effective amount" of an IL-1β binding antibody, antibody fragment, nucleic acid, or vector of the invention is that amount which can treat or prevent one or more symptoms of an IL-1 related disease in a subject.

Accordingly, it may be desirable to titer the dosage of the IL-1β binding antibody, antibody fragment, nucleic acid, or vector of the invention and modify the route of administration as required to obtain the optimal therapeutic effect. Dosage ranges include from about 0.1 ng/kg to up to about 100 mg/kg or more (in terms of active agent amount per unit of body weight of subject administered the active agent), depending on the factors mentioned above. In other embodiments, the dosage ranges from about 0.1 µg/kg to about 100 mg/kg, from about 1 µg/kg to about 100 mg/kg, from about 5 µg/kg to about 100 mg/kg, from about 0.5 mg/kg up to about 100 mg/kg, or from about 1 mg/kg up to about 100 mg/kg. Other dosages can be appropriate. The composition can be administered as a single dose, or as two or more doses (which may or may not contain the same amount of an IL-1β binding antibody, antibody fragment, nucleic acid, or vector of the invention) over time, or as a continuous infusion via, for example implantation device or catheter.

Methods of Use

The antibodies, antibody fragments, nucleic acids, vectors, cells, and compositions of the invention (collectively "the compounds and compositions of the invention") can be used for any purpose. For example, the compounds and compositions of the invention can be used to research IL-1 related mechanisms, as well as the diseases and conditions associated with IL-1 related mechanisms. However, the compounds and compositions of the invention are especially useful to treat a subject (e.g., a mammal or a human) in need of treatment for an IL-1 related condition, e.g., an autoimmune or inflammatory disease or disorder. Accordingly, the invention provides a method of treating or preventing a disease in a mammal comprising administering an effective amount of the antibody or antibody fragment, nucleic acid, or vector of the invention to a mammal in need thereof, whereby the disease is treated or prevented in the mammal. The term "effective amount" refers to the amount of the antibody or antibody fragment, nucleic acid, or vector of the invention needed to establish a prophylactic or therapeutic effect. As used herein, treating a disease or condition is defined as temporarily or permanently reducing or eliminating the symptoms or progression of a disease or condition. Similarly, preventing a disease or condition means temporarily or permanently inhibiting, slowing, or preventing the onset of a disease or condition (or the symptoms of a disease or condition).

The method of the invention can be used to treat or prevent any IL-1 related disease or condition. For example, the present antibodies and fragments are contemplated for use in the prophylaxis and treatment of IL-1 mediated diseases or medical conditions, e.g. inflammatory conditions, allergies and allergic conditions, cancers, hypersensitivity reactions, autoimmune diseases, severe infections, and organ or tissue transplant rejection. IL-1 related conditions include rheumatoid arthritis (RA), osteoarthritis, Crohn's disease, ulcerative colitis (UC), septic shock, chronic obstructive pulmonary disease (COPD), asthma, graft versus host disease, atherosclerosis, adult T cell leukemia, multiple myeloma, multiple sclerosis, stroke, Alzheimer's disease. The present antibodies and fragments can also be used to treat or prevent Neonatal Onset Multisystem Inflammatory Disorder (NOMID/CINCA), systemic onset juvenile idiopathic arthritis, Stills disease, CAPS, or Muckle-Wells syndrome.

In general, a disease or condition can be considered an IL-1β related disease or condition if it is associated with elevated levels of IL-1β in bodily fluids or tissue or if cells or tissues taken from the body produce elevated levels of IL-1β in culture.

For example, the present methods can be used to treat or prevent Neonatal Onset Multisystem Inflammatory Disorder (NOMID/CINCA), systemic onset juvenile idiopathic arthritis, CIAS1 Associated Periodic Syndromes (CAPS), Stills disease, or Muckle-Wells syndrome.

As another example, the present methods can be used to treat or prevent rheumatoid arthritis, osteoarthritis, Crohn's disease, ulcerative colitis, septic shock, chronic obstructive pulmonary disease, asthma, graft versus host disease, atherosclerosis, adult T cell leukemia, multiple myeloma, multiple sclerosis, stroke or Alzheimer's disease.

As yet another example, the present methods can be used to treat or prevent systemic onset juvenile idiopathic arthritis, rheumatoid arthritis, osteoarthritis, atherosclerosis, or myasthenia gravis.

Other examples of IL-1β related conditions are acute pancreatitis; ALS; cachexia/anorexia, including AIDS-induced cachexia; asthma and other pulmonary diseases; autoimmune vasculitis; CIAS1 Associated Periodic Syndromes (CAPS); chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancers, such as multiple myeloma and myelogenous (e.g., AML and CML) and other leukemias, as well as tumor metastasis; diabetes (e.g., insulin diabetes); endometriosis; familial Cold Autoinflammatory Syndrome (FCAS); familial mediterranean fever (FMF); fever; fibromyalgia; glomerulonephritis; graft versus host disease/transplant rejection; hemohorragic shock; hyperalgesia; inflammatory bowel disease; inflammatory conditions of a joint, including psoriatic arthritis (as well as osteoarthritis and rheumatoid arthritis); inflammatory eye disease, as may be associated with, for example, corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; side effects from radiation therapy; sleep disturbance; temporal mandibular joint disease; tumor necrosis factor receptor-associated periodic fever syndrome (TRAPS); uveitis; or an inflammatory condition resulting from strain, sprain, cartilage damage, trauma, orthopedic surgery, infection or other disease processes.

The present antibodies and fragments are also contemplated for use in the treatment recipients of heart, lung, combined heart-lung, liver, kidney, pancreatic, skin or corneal transplants, including allograft rejection or xenograft rejection, or for the prevention of graft-versus-host disease, such as following bone marrow transplant, or organ transplant associated arteriosclerosis.

The present antibodies and fragments are contemplated for use in the treatment or prevention of autoimmune disease or inflammatory conditions, in particular inflammatory conditions with an aetiology including an autoimmune component such as arthritis (for example rheumatoid arthritis, arthritis chronica progrediente and arthritis and rheumatic diseases, including inflammatory conditions and rheumatic diseases involving bone loss, inflammatory pain, hypersensitivity (including both airways hypersensitivity and dermal hypersensitivity) or allergies. Specific auto-immune diseases for which the present antibodies and fragments may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis or glomerulonephritis (with and without nephrotic syndrome, e.g. including idiopathic nephrotic syndrome or minimal change nephropathy).

The present antibodies and fragments are also contemplated for use in the treatment, prevention, or amelioration of asthma, bronchitis, pneumoconiosis, pulmonary emphysema, and other obstructive or inflammatory diseases of the airways. The antibodies or fragments for treating undesirable acute and hyperacute inflammatory reactions which are mediated by IL-1or involve production, especially or the promotion of TNF release by IL-1, e.g. acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

The present antibodies and fragments are also contemplated for use in treating diseases of bone metabolism including osteoarthritis, osteoporosis and other inflammatory arthritides, and bone loss in general, including age-related bone loss, and in particular periodontal disease.

The present antibodies and fragments are also contemplated for use in the treatment or prevention of CIAS1 Associated Periodic Syndromes (CAPS), including each of Neonatal Onset Multisystem Inflammatory Disorder (NOMID), Muckle-Wells Syndrome (MWS), and Familial Cold Autoinflammatory Syndrome (FCAS). Mutations in the gene CIAS1 are now recognized as being responsible for three rare genetic syndromes: Neonatal Onset Multisystem Inflammatory Disorder (NOMID), Muckle-Wells Syndrome (MWS), and Familial Cold Autoinflammatory Syndrome (FCAS). (Hoffman et al. 2001 Naure 29:301-305; Feldmann et al. 2002 Am J Hum Genet 71:198-203; Aksentijevich et al. 2002 Arthritis Rheum 46:3340-3348). In aggregate, these conditions are known as "CAPS." CIAS1 encodes a protein called NALP3 that is a component of the "inflammasome", a subcellular enzyme complex that regulates the activity of caspase 1. Caspase 1 is the enzyme that cleaves the inactive pro-form of the proinflammatory cytokine, IL-1, into its biologically active form (Agostini et al. 2004 supra). Mutations in CIAS1 lead to increased production of IL-1.

The antibody or antibody fragment, nucleic acid, or vector of the invention is typically administered to the mammal or human as a pharmaceutical composition comprising an antibody or antibody fragment, nucleic acid, or vector of the invention and a pharmaceutically acceptable carrier. Pharmaceutical compositions suitable for use in conjunction with the method of treating or preventing a disease are as previously described herein.

The antibody or antibody fragment, nucleic acid, or vector of the invention can be administered to the mammal as the sole active agent, or in conjunction with one or more other agents that disrupt IL-1 receptor signaling. An agent that disrupts IL-1 receptor signaling can be any compound or composition that inhibits an interaction between IL-1β and IL-1 receptor. For example, agents that disrupt IL-1 receptor signaling include antibodies that bind to IL-1β or to the IL-1 receptor, recombinant IL-1Ra (e.g., from Amgen Inc., Thousand Oaks, Calif.), and IL-1 receptor "trap" peptides (e.g., from Regeneron Inc., Tarrytown, N.Y.). When two or more agents that disrupt IL-1 receptor signaling are used, they can be administered together (e.g., in a single pharmaceutical composition), or they can each be administered separately (e.g., in separate pharmaceutical compositions).

The antibody, fragment, nucleic acid, or vector of the invention can be administered to a mammal in combination or in conjunction with one or more other active agents for treating or preventing IL-1 mediated conditions or diseases are set forth above.

Diagnostic Uses

In addition to therapeutic uses, the present antibodies and fragments can be used in diagnostic methods to detect IL-1β (for example, in a biological sample, such as serum or plasma), using a conventional immunoassay, such as an enzyme linked immunosorbent assays (ELISA), an radioimmunoassay (RIA) or tissue immunohistochemistry. A method for detecting IL-1β in a biological sample can comprise the steps of contacting a biological sample with one or more of the present antibodies or fragments and detecting either the antibody or fragment bound to IL-1β or unbound antibody or fragment, to thereby detect IL-1β in the biological sample. The antibody or fragment can be directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Rather than labeling the antibody, IL-1β can be assayed in biological fluids by a competition immunoassay utilizing IL-1β standards labeled with a detectable substance and an unlabeled anti-IL-1β antibody. In this assay, the biological sample, the labeled rIL-1β standards and the anti-IL-1β antibody are combined and the amount of labeled IL-1β standard bound to the unlabeled antibody is determined. The amount of IL-1β in the biological sample is inversely proportional to the amount of labeled IL-1β standard bound to the anti-IL-1β antibody.

EXAMPLES

The following examples further illustrate the invention but, of course, should not be construed as in any way limiting its scope.

In the following Examples, reference is made to various antibodies of the present invention, including the antibodies designated AB1, AB5, and AB7. As mentioned above, AB1 comprises a heavy chain variable region comprising the amino acid sequence of SEQ ID NO:4 and a light chain variable region comprising the amino acid sequence of SEQ ID NO:9. AB5 comprises a heavy chain variable region comprising the amino acid sequence of SEQ ID NO:8 and a light chain variable region comprising the amino acid sequence of SEQ ID NO:9. AB7 comprises a heavy chain variable region comprising the amino acid sequence of SEQ ID NO:15 and a light chain variable region comprising the amino acid sequence of SEQ ID NO:11.

For various comparisons in the following Examples, reference is made to an antibody designated AB-control, a commercially available antibody with relatively high affinity for IL-1β. AB-control is a murine antibody which is believed to have a heavy chain comprising the sequence of SEQ ID NO:40 and a light chain comprising the sequence of SEQ ID NO:41. These murine sequences are set forth in U.S. Patent Application Publication No. 2003/0026806, at FIGS. 6A and 6B.

In several of the Examples that follow, AB5 and AB7 are shown to have unexpectedly higher affinity to human IL-1β than AB-control.

Example 1

This example illustrates the binding affinities of certain antibodies of the invention to IL-1β.

Antibodies designated AB1 and AB5 were assayed for IL-1β binding properties using a KINEXA™ device (from Sapidyne Instruments Inc., Boise, Id.). The amino acid sequences of the heavy and light chain variable regions of antibodies AB1 and AB5 are provided in FIGS. 2 and 3. A commercially available antibody with relatively high affinity for IL-1β (herein AB-control) was assayed for comparison.

IL-1β binding assay results are summarized in Table 1. $K_D$ values represent the binding dissociation constants for the respective antibody-IL-1β complexes. $K_D$ was calculated as the ratio of "off rate" (rate of dissociation for the antibody-IL-1β complex) to "on rate" (rate of association for the antibody-IL-1β complex). A lower $K_D$ rate is indicative of higher antibody affinity.

TABLE 1

IL-1β Binding Results

| Antibody | $K_D$ (pM) |
|---|---|
| AB-control | 3.06 |
| AB1 (invention) | 18.63 |
| AB5 (invention) | 0.261 |

The results of these experiments show that AB1 and AB5 bind IL-1β with high affinity. The affinities for IL-1β of the antibodies of the invention are comparable to, or better than, the binding affinity of AB-control for IL-1β.

Example 2

This example illustrates the in vitro inhibition of IL-1β using antibodies of the invention.

The IL-1β inhibitory potencies of AB1 and AB5 antibodies (see Example 1) were evaluated using a bioassay that measures the IL-1β stimulated release of IL-6 from human fibroblasts. As in Example 1, AB-control was used as a comparative sample. Details of the assay are described in Dinarello et al., Current Protocols in Immunology, Ch. 6.2.1-6.2.7, John Wiley and Sons Inc., Hoboken, N.J., 2000. Briefly, human MRC5 human fibroblasts from the American Type Culture Collection (ATCC) Manassas, Va. (ATCC #CCL-171) were grown to confluency in multi-well plates. Cells were treated with titrated doses of AB5 antibody. Cells were subsequently contacted with (i) 100 pg/ml of IL-1β or (ii) 100 pg/ml of IL-1β and AB1 or AB5 antibody (from Example 1). Negative control cells were not stimulated with IL-1β. The amounts of IL-6 released in each group of treated cells were measured using an IL-6 ELISA kit from BD Pharmingen (Franklin Lakes, N.J.) according to the manufacturer's instructions. ELISA results are depicted in FIG. 5 and summarized in Table 2. $IC_{50}$ is the concentration of antibody required to inhibit 50% of IL-6 released by IL-1β stimulation.

TABLE 2

ELISA Results

| Antibody | $IC_{50}$ (nM) |
|---|---|
| AB-control | 0.017 |
| AB1 (invention) | 0.15 |
| AB5 (invention) | 0.014 |

These results demonstrate the in vitro potency of the antibodies of the invention to inhibit IL-1β. Furthermore, inhibition of IL-1β-stimulated cytokine release in MRC 5 has been shown to correlate with the agent's ability to inhibit IL-1 mediated activity in vivo. Thus, these results indicate that the antibodies of the invention will have IL-1β inhibitory efficacy in vivo.

Example 3

This example illustrates the in vivo inhibition of IL-1β using antibodies of the invention.

To confirm the in vivo efficacy of AB5, its ability to block the biological activity of human IL-1β was tested in mice. Details of the assay are described in Economides et al., Nature Med., 9: 47-52 (2003). Briefly, male C57/B16 mice (Jackson Laboratory Bar Harbor, Me.) were injected intraperitoneally with titrated doses of AB5 (Example 1), AB-control (Example 1), or control IgG (Jackson ImmunoResearch Laboratories, West Grove, Pa.). Twenty-four hours after antibody injection, mice were injected subcutaneously with recombinant human IL-1β (rhIL-1β) (from PeproTech Inc., Rocky Hill, N.J.) at a dose of 1 μg/kg. Two hours post-rhIL-1β injection (peak IL-6 response time), mice were sacrificed, and blood was collected and processed for serum. Serum IL-6 levels were assayed by ELISA (BD Pharmingen, Franklin Lakes, N.J.) according to the manufacturer's protocol. Percent inhibition was calculated from the ratio of IL-6 detected in experimental animal serum to IL-6 detected in control (multiplied by 100).

Figure 6:
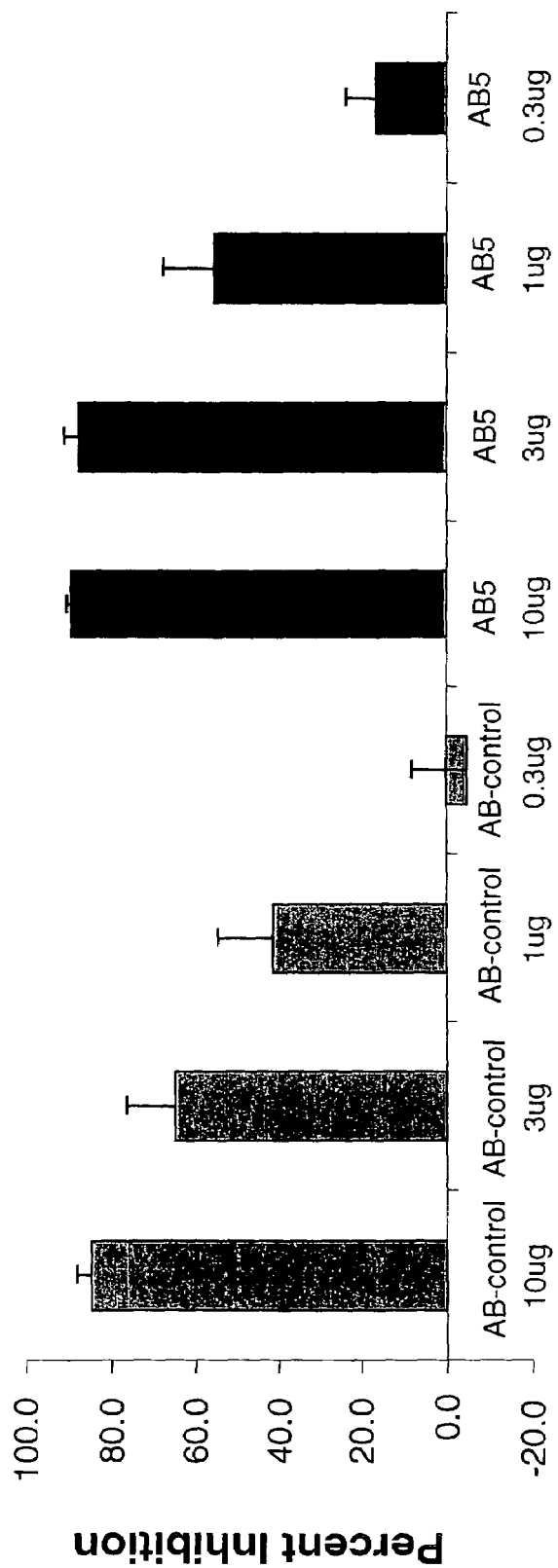
FIG. 6 is a histogram showing the results of an in vivo IL-1β stimulation experiment.

The results are set forth in FIG. 6. The ability to inhibit the in vivo activity of IL-1β is assessed as a function of IL-1β stimulated IL-6 levels in serum. As illustrated by FIG. 6, the AB5 antibody was as effective, if not more effective, than AB-control for inhibiting the in vivo activity of human IL-1β. 3 μg of AB5 was as effective as a 10 μg of AB-control in this assay.

Thus, the results indicate that the tested antibodies are useful for the inhibition of IL-1β activity in vivo. These results also show that a single injection of AB5 can block the systemic action to IL-1β stimulation over a prolonged period of time.

Example 4

The following example illustrates the preparation of an antibody in accordance with the invention.

A number of human engineered antibody sequences were generated using HUMAN ENGINEERING™ technology as described in Studnicka et al., Protein Engineering, 7: 805-814 (1994), and in U.S. Pat. Nos. 5,766,886, 5,770,196, 5,821, 123, and 5,869,619, and PCT Application Publication WO 93/11794. Generated human engineered antibody sequences include AB5.1, AB5.2, AB5.3 and AB5.4. As shown in FIGS. 3 and 4, each of these sequences comprise two variable positions in the CDR-3H region indicated by $X_1$ and $X_2$. Thus, in certain examples of each one of these human engineered antibodies, $X_1$ and $X_2$ of the CDR3 correspond to alanine and arginine, valine and arginine, phenylalanine and arginine, lysine and lysine, or asparagine and arginine, respectively.

Example 5

Antibodies designated AB5 and AB7 (a human engineered antibody sequence) were assayed for IL-1β binding properties using a kinetic exclusion assay performed on a KINEXA™ device in a manner like that described in Example 1. Additional description about KINEXA™ devices and operation for antibody characterization is available from the manufacturer and can be found in the published literature, for example U.S. Pat. No. 6,664,114 (Sapidyne, Inc.); and Darling et al., "Kinetic Exclusion Assay Technology: Characterization of Molecular Interactions." ASSAY and Drug Development Technologies, 2004, 2, 647-657. The KINEXA™ device performs a kinetic exclusion assay, and fits the data to various theoretical curves and thus determines $K_D$ as well as other properties, such as 95% confidence intervals for $K_D$. The KINEXA™ device is generally more sensitive than other devices (e.g., a BiaCore device) for analysis of affinity characteristics such as dissociation constants and off-rates.

The amino acid sequences of the heavy and light chain variable regions of AB5 and AB7 are provided in FIGS. 3 and 4A, respectively. IL-1β binding assay results are summarized in Table 3. As in Example 1, $K_D$ was calculated as the ratio of "off rate" to "on rate", and a lower $K_D$ rate is indicative of higher antibody affinity.

TABLE 3

| Antibody | $K_D$ (pM) |
|---|---|
| AB5 | 0.24 |
| AB7 | 0.30 |

The results of these experiments show that AB5 (consistent with results observed in Example 1) and AB7 bind IL-1β with unexpectedly high affinity, which is represented by the unexpectedly low values for their dissociation constants.

Figure 7:
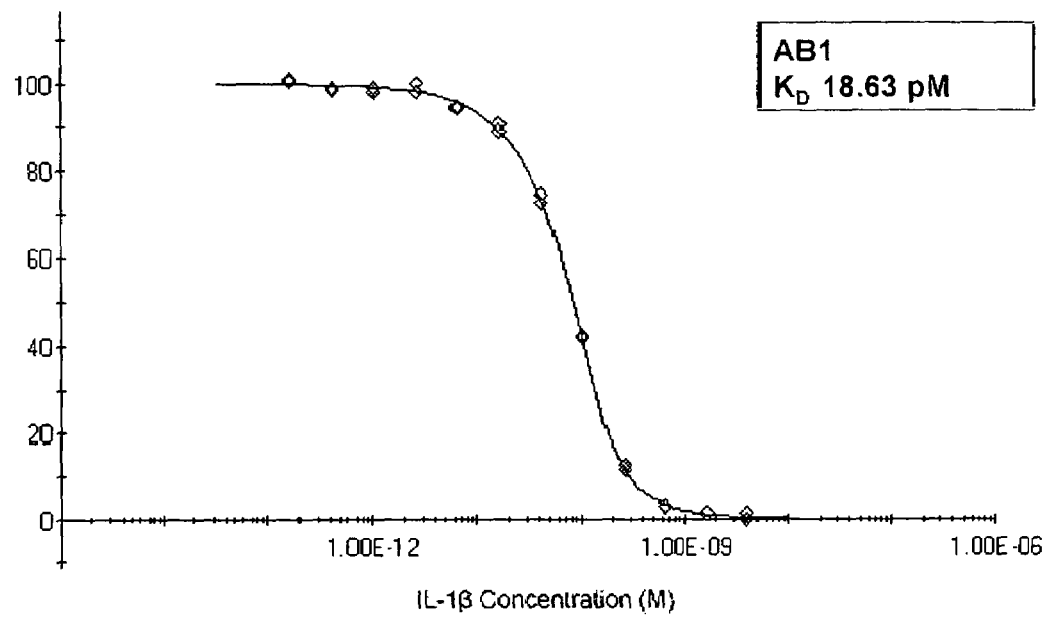
FIG. 7 is a graph showing kinetic exclusion assay results for the antibody designated AB1.
Figure 8:
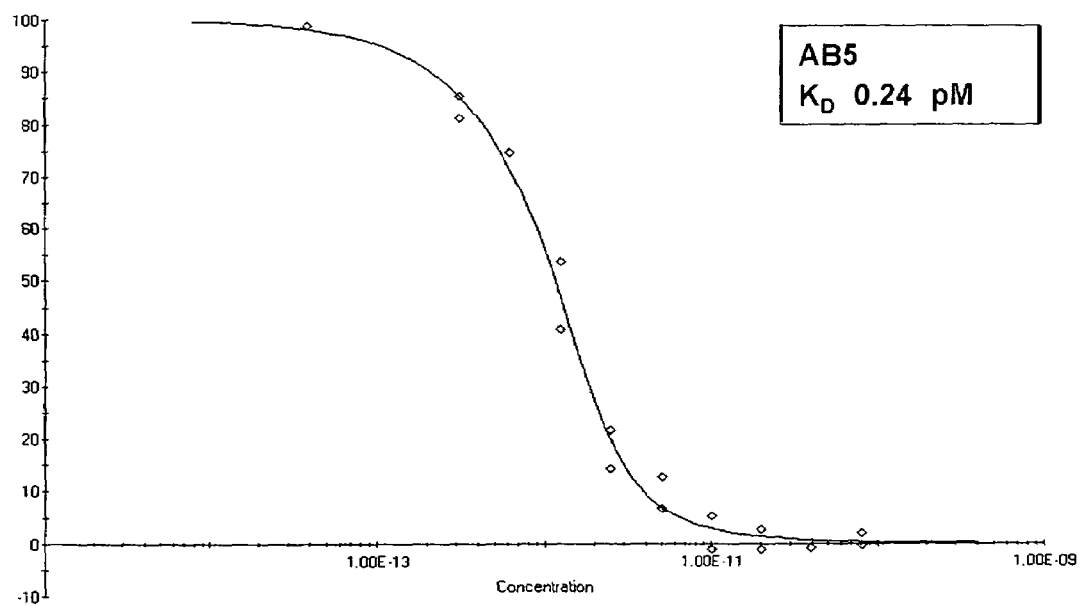
FIG. 8 is a graph showing kinetic exclusion assay results for the antibody designated AB5.
Figure 9:
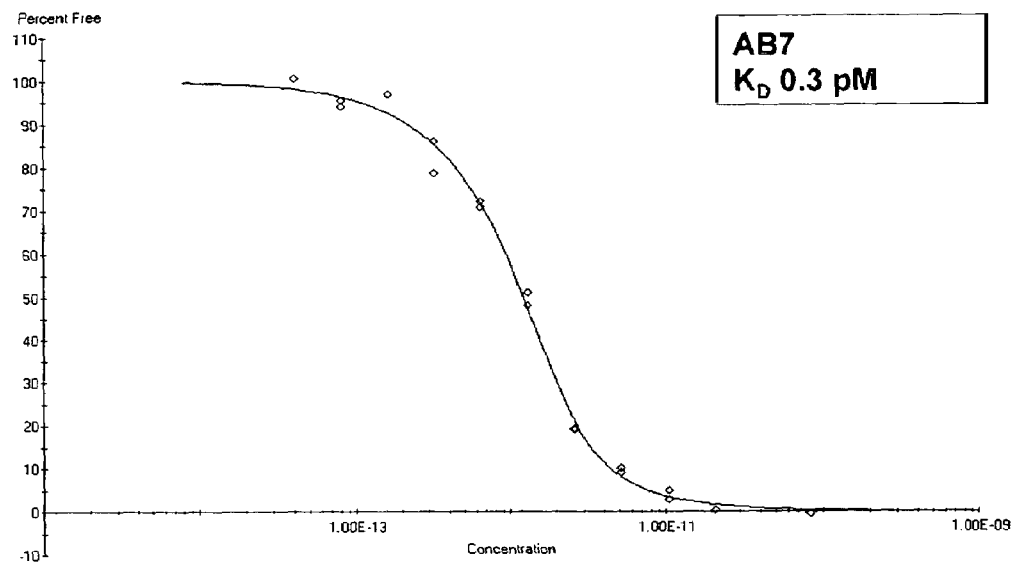
FIG. 9 is a graph showing kinetic exclusion assay results for the antibody designated AB7.

FIGS. 7, 8, and 9 show the binding affinities of antibodies designated AB1, AB5, and AB7, respectively, as determined from one representative experiment for each using KINEXA analysis. FIG. 7 reflects the results set forth in Table 1, while FIGS. 8 and 9 reflects the results set forth in Table 3.

In addition to the values set forth in Table 3, the KINEXA assay results also indicate low and high 95% confidence intervals ($K_D$-low and $K_D$-high). For AB5, $K_D$-low was 0.07 pM, and $K_D$-high was 0.72 pM. For AB7, $K_D$-low was 0.11 pM, and $K_D$-high was 0.74 pM.

Similar $K_D$-low and $K_D$-high values were found in the assay set forth in Example 1. For AB-control, $K_D$-low was 1.62 pM, and $K_D$-high was 5.23 pM. For AB1, $K_D$-low was 13.38 pM, and $K_D$-high was 24.84 pM. For AB5, $K_D$-low was 0.11 pM, and $K_D$-high was 0.56 pM.

The KINEXA assay results indicate that AB5 and AB7 had an unexpectedly-lower dissociation constant than AB-control.

Example 6

This example illustrates the in vitro inhibition of IL-1β stimulated release of IL-6. $IC_{50}$ for inhibiting IL-1β stimulated release of IL-6 from human fibroblasts was assayed for several antibodies of the present invention as follows.

Figure 10:
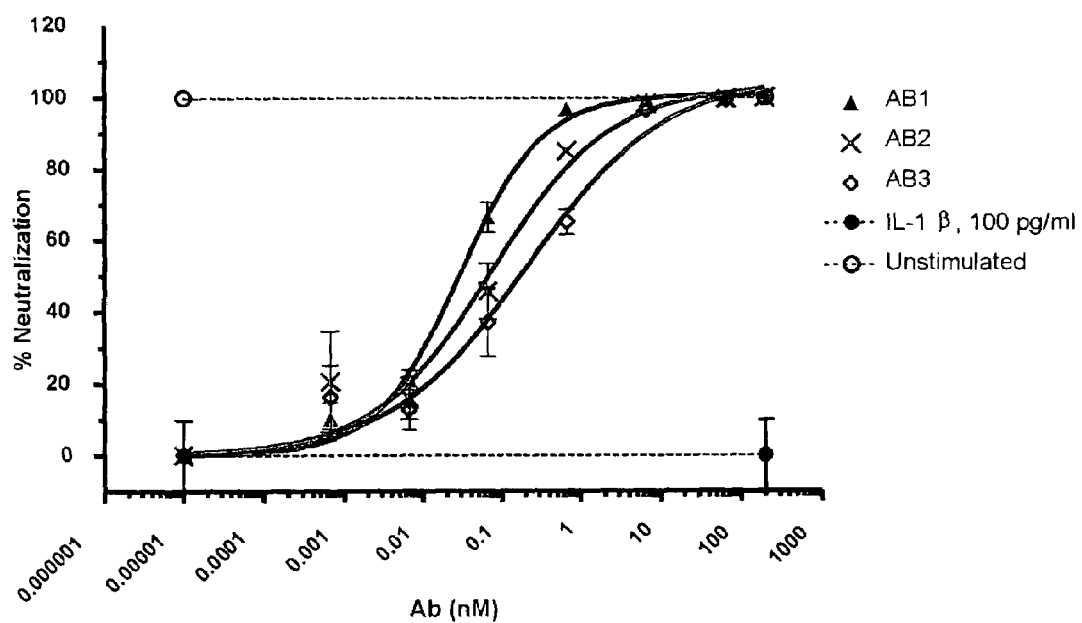
FIG. 10 is a graph showing the results of an in vitro IL-1β stimulation experiment for the antibodies designated AB1, AB2, and AB3.
Figure 11:
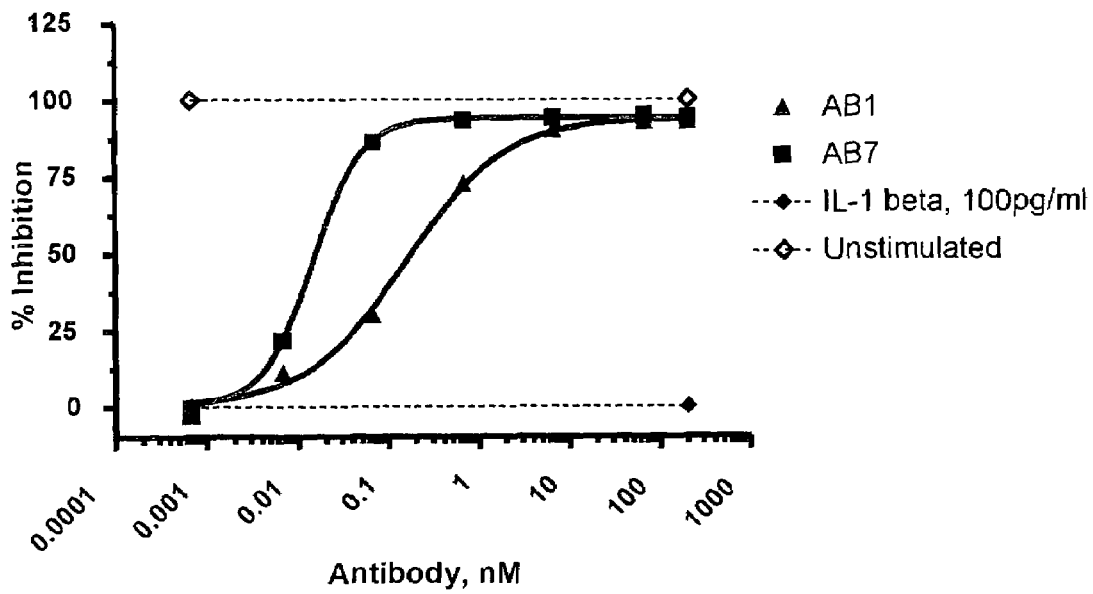
FIG. 11 is a graph showing the results of an in vitro IL-1β stimulation experiment for the antibodies designated AB1 and AB7.
Figure 12:
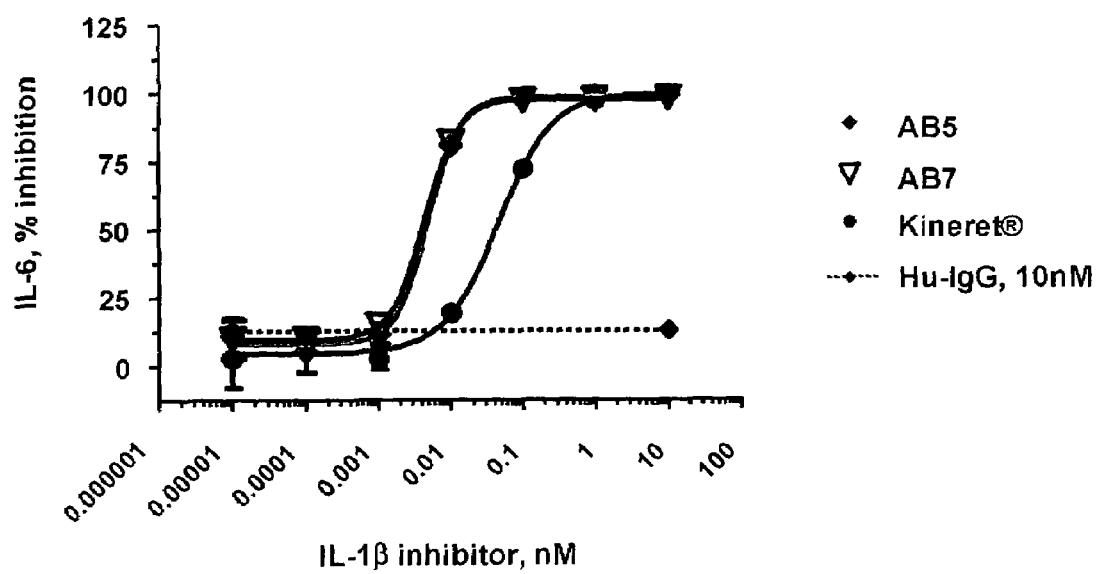
FIG. 12 is a graph showing the results of an in vitro IL-1β stimulation experiment for the antibodies designated AB5 and AB7, as well as for Kineret®.

The IL-1β inhibitory potency of AB5 and AB7 was evaluated in a manner like that described in Example 2, using a bioassay that measures the IL-1β stimulated release of IL-6 from human fibroblasts. FIGS. 10-12 show binding curves for individual assays on various antibodies. FIG. 10 shows the inhibition of IL-6 release from human fibroblasts by antibodies designated AB1, AB2 and AB3, and the results of these three individual assays indicated that AB1 had an $IC_{50}$ of 0.029 nM (29 pM), AB2 had an $IC_{50}$ of 0.076 pM (76 pM), and AB3 had an $IC_{50}$ of 0.214 nM (214 pM). FIG. 11 shows the inhibition of IL-6 release from human fibroblasts by antibodies designated AB1 and AB7 in an additional assay. FIG. 12 shows the inhibition of IL-6 release from human fibroblasts by antibodies AB5 and AB7, as well as the commercially available Kineret®. The results indicated that AB5 and AB7 had substantially better potency with respect to inhibiting IL-1β than Kineret®, based on $IC_{50}$ determinations in the assays. Kineret® is a man-made protein that is similar to a naturally occurring protein called interleukin-1 receptor antagonist (IL-1ra) found in the body. FIGS. 10-12 show individual assay results for the potency of the antibodies or Kineret® in terms of percent inhibition of IL-6 without the antibody, and Table 4 shows the $IC_{50}$ calculated from those individual assays. $IC_{50}$ is the concentration of antibody or Kineret® required to inhibit 50% of IL-6 released by IL-1β stimulation.

TABLE 4

| Antibody | $IC_{50}$ (Nm) |
|---|---|
| AB5 | 0.0049 (4.9 pM) |
| AB7 | 0.0044 (4.4 pM) |
| Kineret | 0.0454 (45.4 pM) |

In addition to the individual assay results reported in Tables 2 and 4 and shown in FIGS. 6, 10, 11 and 12, other individual assays were conducted for each of AB1, AB7 and AB-control. A mean $IC_{50}$ can be calculated from individual assay results. A mean $IC_{50}$ for AB1 of 66.7 pM was calculated from individual assay results of 35 pM, 30 pM, 150 pM (this value is also shown in Table 2), and 52 pM. A mean $IC_{50}$ for AB7 of 5.6 pM was calculated from individual assay results of 7.3 pM, 4.2 pM, 4.5 pM, 4.4 pM (this value is also shown in Table 4), 6.0 pM, 5.0 pM, and 7.8 pM. A mean $IC_{50}$ for AB-control of 8.9 pM was calculated from individual assay results of 5.0 pM, 17.0 pM (this value is also shown in Table 2), and 4.9 pM.

These results demonstrate the in vitro potency of the AB1, AB5 and AB7 to inhibit IL-1β. Furthermore, inhibition of IL-1β-stimulated cytokine release in human fibroblasts has been shown to correlate with the inhibiting agent's ability to inhibit IL-1 mediated activity in vivo. Thus, these results indicate that the antibodies of the invention will have IL-1β inhibitory efficacy in vivo.

Example 7

This example illustrates the in vivo inhibition of IL-1β using IL-1β binding antibodies.

Figure 13:
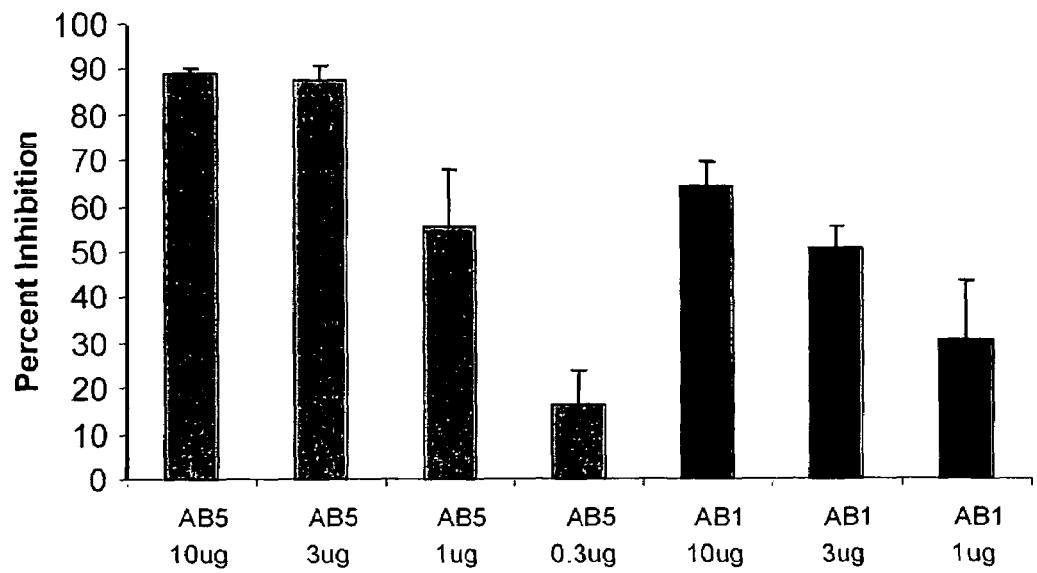
FIG. 13 is a histogram showing the results of an in vivo IL-1β stimulation experiment for the antibodies designated AB5 and AB1.
Figure 14:
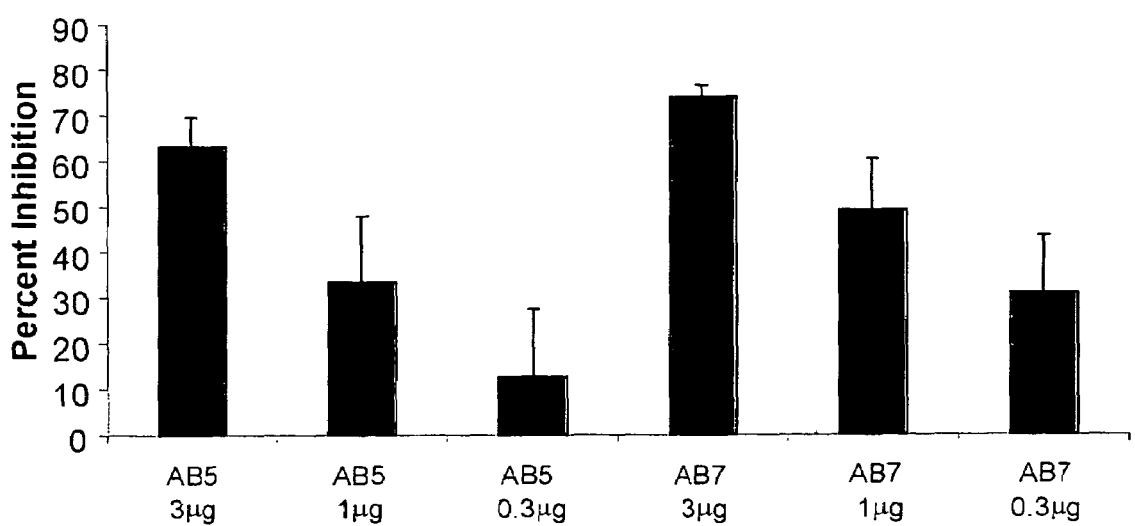
FIG. 14 is a histogram showing the results of an in vivo stimulation experiment for the antibodies designated AB5 and AB7.

The in vivo efficacy of AB5, AB1 and AB7 and their ability to block the biological activity of human IL-1β were tested in mice in a manner like that described in Example 3. Results from testing AB5 and AB1 are set forth in FIG. 13, and results from testing AB5 and AB7 are set forth in FIG. 14. The ability to inhibit the in vivo activity of IL-1β was assessed as a function of IL-1β stimulated IL-6 levels in serum. As illustrated by FIGS. 13 and 14, the AB1, AB5 and AB7 antibodies were effective for inhibiting the in vivo activity of human IL-1β.

These results indicate that the tested antibodies are useful for the inhibition of IL-1β activity in vivo.

Example 8

This Example illustrates that at least some IL-1β binding antibodies according to the present invention are cross-reactive with IL-1β from some mammals other than humans, and are not cross-reactive with IL-1β from other non-human mammals. Antibody designated AB7 (an antibody that binds to human IL-1β with high affinity) was assayed for binding to IL-1β from non-human mammals, namely rhesus macaque, cynomolgus monkey, dog, guinea pig, and rabbit.

Fresh heparanized whole blood from rhesus macaque, cynomolgus monkey, dog, guinea pig and rabbit was obtained from Charles River Labs. The whole blood was separated by Ficoll density gradient centrifugation and peripheral blood mononuclear cells (PBMC's) were isolated. For each species' PBMC, $2.5 \times 10^5$ cells/ml were incubated in peripheral RPMI media with and without 50 ng/ml Lipopolysaccharide LPS (E. Coli 055:B5), and supernatants were collected at 24 hours post-stimulation. LPS is intended to stimulate the production of IL-1β by the PBMC's. 2 ml of each supernatant was incubated for 3 hours with 2 μg of AB7 followed by addition of 50 μl protein A-Sepharose bead slurry to immunoprecipitate the AB7/IL-1 complex. Human IL-1β (Peprotech) was spiked into RPMI and run as immunoprecipliation/Western blot controls. After centrifugation and washing of the Protein A-Sepharose beads, all samples were loaded onto a SDS-PAGE gel and run at 120V for 1 hour. Following transfer to Immobilon-P membrane at 22V overnight and blocking with 5% nonfat milk, AB7 was incubated at 2 μg/ml with the membrane for 2 hours. A secondary goat anti-human IgG antibody conjugated with horseradish peroxidase (HRP) was added following wash steps and detection was with one step tetramethyl benzidine (TMB) solution.

Figure 15:
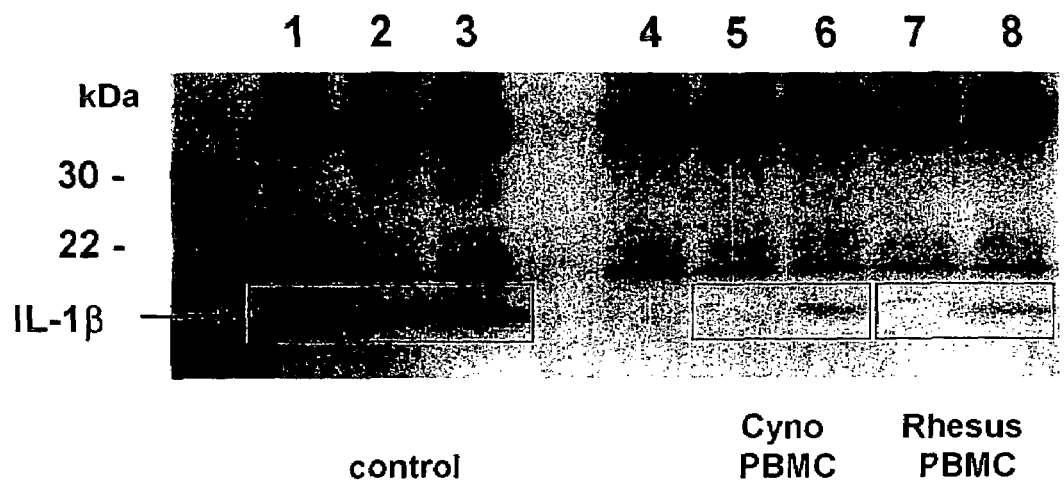
FIG. 15 is a Western blot showing the results of cross-reactivity experiments for the antibody designated AB7 with IL-1β from cynomolgus monkey and rhesus macaque.
Figure 16:
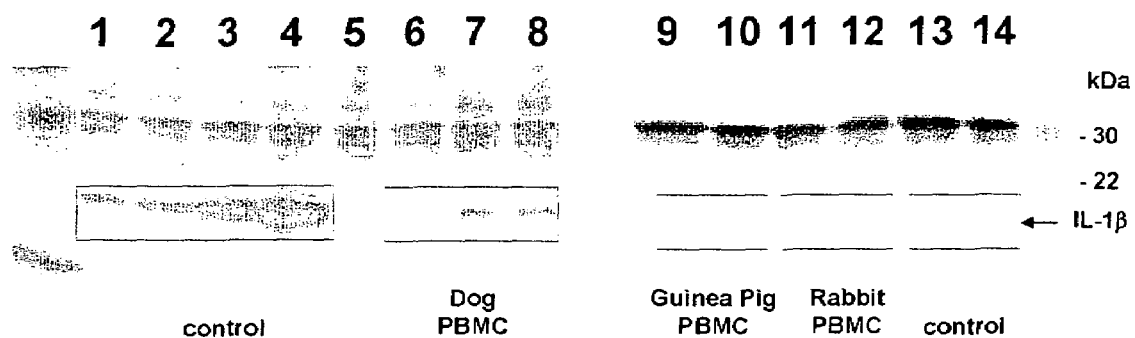
FIG. 16 is a Western blot showing the results of cross-reactivity experiments for the antibody designated AB7 with IL-1β from dog, guinea, pig, and rabbit.

FIGS. 15 and 16 show the Western blots obtained from this procedure. On the left side of the blot shown in FIG. 15 (lanes 1-3) are the controls in which varying amounts (5 ng, 10 ng, and 20 ng) of human IL-1β were added to the RPMI media. Near the bottom of the blot, bands can be seen in each of the lanes at a region corresponding to a molecular weight of approximately 17 kDa. These bands are indicative of the binding of AB7 to human IL-1β. The middle lane (lane 4) is the RPMI media. On the right side of the blot shown in FIG. 15 (lanes 5-8), the results for the samples from cynomolgus monkey and rhesus macaque are shown. Lanes 5 and 6 are the cynomolgus monkey samples without LPS and with 50 ng LPS added to the RPMI media, respectively. Lanes 7 and 8 are the rhesus macaque samples without LPS and with 50 ng LPS added to the RPMI media, respectively. Near the bottom of the Western blot, bands can be seen in Lanes 6 and 8 (the samples to which LPS was added) at a region corresponding to a molecular weight of approximately 17 kDa. These bands in Lanes 6 and 8 are indicative of cross-reactivity of AB7 with primate IL-1β, namely IL-1β from cynomolgus monkey and rhesus macaque.

FIG. 16 shows Western blots for controls and samples from PBMC's of dog, guinea pigs, and rabbits. On the left side of the blots shown in FIG. 16 (lanes 1-4) are the controls in which varying amounts (5 ng, 10 ng, 50 ng, and 200 ng) of human IL-1β were added to the RPMI media. Near the bottom of the blot, bands can be seen in each of the lanes at a region corresponding to a molecular weight of approximately 17 kDa. These bands are indicative of the binding of AB7 to human IL-1β. Lane 5 in FIG. 15 is the RPMI media. Lanes 6-8 are the results for the samples from dog PBMC's, with no LPS, 50 ng LPS and 200 ng LPS, respectively. Lanes 9 and 10 are the results for the samples from guinea pig PBMC's, with no LPS and 50 ng LPS, respectively. Lanes 11 and 12 are the results for the samples from rabbit PBMC's, with no LPS and 50 ng, respectively. Near the bottom of the Western blot, bands can be seen in Lanes 7, 8 and 12 (the dog and rabbit samples to which LPS was added) at a region corresponding to a molecular weight of approximately 17 kDa. These bands in Lanes 7, 8 and 12 are indicative of cross-reactivity of AB7 with dog IL-1β and rabbit IL-1β. The absence of a visible band in Lane 10 (guinea pig PBMC with 50 ng LPS added) indicates that AB7 was not cross-reactive with guinea pig IL-1β.

These results indicate that AB7 is cross-reactive with IL-1β from several non-human mammals, namely rhesus macaque, cynomolgus monkey, dog, and rabbit, but is not cross-reactive with IL-1β from at least one other non-human mammal, namely guinea pig.

Example 9

This Example further illustrates that at least some IL-1β binding antibodies according to the present invention are cross-reactive with IL-1β from other non-human mammals. Antibody AB7 was assayed for binding to IL-1β from non-human mammals, namely mouse and rat.

Recombinant human, mouse and rat IL-1β (Peprotech) were loaded in reducing and non-reducing condition onto a SDS-PAGE gel and run at 120V for 1 hr. Following transfer to Immobilon-P membrane at 22V overnight and blocking with 5% nonfat milk, AB7 was incubated at 2 μg/ml with the membrane for 2 hours. A secondary goat anti-human IgG HRP conjugated antibody was added following wash steps and detection was with one step TMB solution.

Figure 17:
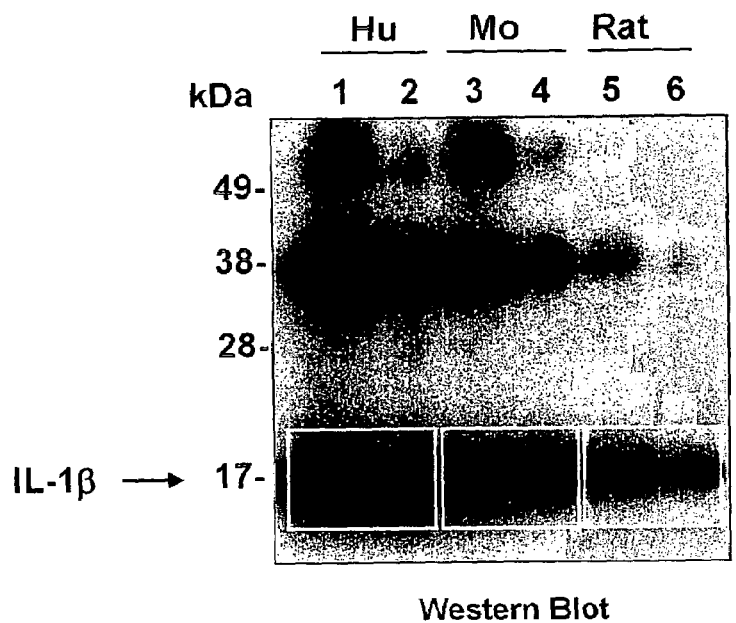
FIG. 17 is a Western blot showing the results of cross-reactivity experiments for the antibody designated AB7 with recombinant human, mouse, and rat IL-1β.

FIG. 17 shows the Western blot obtained by the foregoing procedures. Lanes 1 and 2 are for non-reduced and reduced human IL-1β, respectively. Lanes 3 and 4 are for non-reduced and reduced mouse IL-1β, respectively. Lanes 5 and 6 are for non-reduced and reduced rat IL-1β, respectively. At the bottom of the blot, bands can be seen in each of the lanes at a region corresponding to a molecular weight of approximately 17 kDa. These bands are indicative of the presence IL-1β, which in turn is indicative of the binding of AB7 to human IL-1β, mouse IL-1β, and rat IL-1β. These results indicate that AB7 is cross-reactive with rodent IL-1β.

Example 10

This Example further illustrates that at least some IL-1β binding antibodies according to the present invention are inhibitors of IL-1β from humans and at least some non-human mammals. Antibody AB7 was assayed for inhibiting the proliferation of D10 cells stimulated by human, rhesus macaque, mouse and rat IL-1β.

D10.G4.1 (D10) cells are murine T helper cells with specificity for the conalbumin antigen from egg white. This cell line was derived from the AKR/J mouse (H-$2^k$ MHC haplotype) and requires IL-1 and antigen receptor activation for growth, proliferation, and survival. The D10 cell line is highly sensitive to IL-1 and can respond to IL-1 from several species (including human, monkey, mouse, and rat) which allows for testing the cross-reactive neutralizing potential of an IL-1β binding antibody or fragment, such as AB7. D10 proliferation is not affected by LPS or by macrophage-derived cytokines such as IL-6 and TNF-a. As a result, D10 assays can be used to assess the specific IL-1 activity from endogenous sources (i.e., LPS-activated macrophages).

D10 cells were activated with Concanavalin A (Con A) and a constant level of recombinant or native source of IL-1 in the presence or absence of several concentrations of AB7. Cells were plated at $2 \times 10^4$/well and stimulated with 2.5 μg/ml Con A and different concentrations of IL-1β. Cells were cultured for 72 hours and proliferation was measured by adding the redox viability dye Alamar Blue during the last 8-14 hours of culture and assessing the O.D.$_{570-600}$.

To test the potency and species cross-reactivity of AB7, the D10 bioassay was performed using the following concentrations of recombinant or native IL-1β: 10 pg/ml recombinant human IL-1β; 10 pg/ml recombinant rhesus IL-1β; 10 pg/ml mouse IL-1β; and 100 pg/ml rat IL-1β. For the D10 assay employing endogenous human IL-1β, a 1:360 dilution of supernatant from LPS-activated human PBMC's was used. Different concentrations of AB7 were tested with each IL-1β. $IC_{50}$ measurements were determined using Graphpad Prism. Mean, standard deviation (SD), and standard error (SEM) for $IC_{50}$ were calculated using Microsoft Excel.

Results from the D10 assay are summarized in Table 5, which includes the mean $IC_{50}$ and the SEM (based on 4 experiments for recombinant human IL-1β and 3 experiments for the IL-1β from other sources). AB7 was highly potent in neutralizing recombinant human IL-1β and endogenously produced (native) human IL-1β. AB7 was also highly potent in neutralizing recombinant rhesus macaque IL-1β. AB7 also neutralized recombinant mouse IL-1β with lower potency, having an $IC_{50}$ that was 1000-fold higher compared to human. AB7 did not have significant activity against rat IL-1β in this assay.

TABLE 5

ELISA Results

|  | $IC_{50}$ (pM) | SEM (pM) |
|---|---|---|
| recombinant human IL-1β | 2.4 | ±0.52 |
| endogenously produced (native) human IL-1β | 2.6 | ±0.11 |
| recombinant rhesus macaque IL-1β | 2.7 | ±0.73 |
| recombinant mouse IL-1β | 2618 | ±60.9 |

These results indicate that AB7 is a highly potent neutralizing antibody against human IL-1β, with similar potency against recombinant and native forms of the cytokine. Activity against the non-human primate rhesus macaque IL-1β was similar as that against human IL-1β. Thus, at least some antibodies and fragments of the present invention encompass antibodies and fragments having substantially the same potency against human IL-1β and primate IL-1β and/or having substantially the same potency against recombinant human IL-1β and endogenous human IL-1β. These results also indicate that AB7 also neutralizes mouse IL-1β.

Example 11

This Example illustrates the mapping of the IL-1β epitope to which at least some antibodies of the present invention (for example, the antibody designated AB7) bind.

A PepSpot™ peptide array (JPT Peptide Technologies, Berlin, Germany) was used to identify the IL-1β key amino-acid residues (epitope) involved in the binding of AB7. A scan of twelve amino-acid peptides, spanning the entire IL-1β amino-acid sequence, each peptide overlapping by 11 amino acid to the previous one, were synthesized directly on a membrane. The membrane carrying the peptides was probed with AB7 at a concentration of 2 μg/ml, for 2 hr at room temperature. Binding of AB7 to membrane bound peptides was detected using a secondary HRP-conjugated goat anti-human antibody, followed by enhanced chemiluminescence (ECL). The peptides spots corresponding to IL-1β residues 83-105 scored positive for binding to AB7.

This mapping indicates that AB7 binds to an epitope within the sequence corresponding to residues 83-105 of the mature IL-1β protein. The sequence comprises the amino acids ESVDPKNYPKKKMEKRFVFNKIE, and AB7 is exemplary of antibodies that bind to an epitope within this sequence. It is expected that the antibodies designated AB6, AB8, AB9, and others, such as antibodies having the heavy chain of SEQ ID NO:29 and the light chain of SEQ ID NO:27, also bind to an epitope contained in this sequence.

Example 12

This example illustrates the in vitro inhibition of IL-1β using an antibody of the invention in an cell based assay IL-8.

Figure 18:
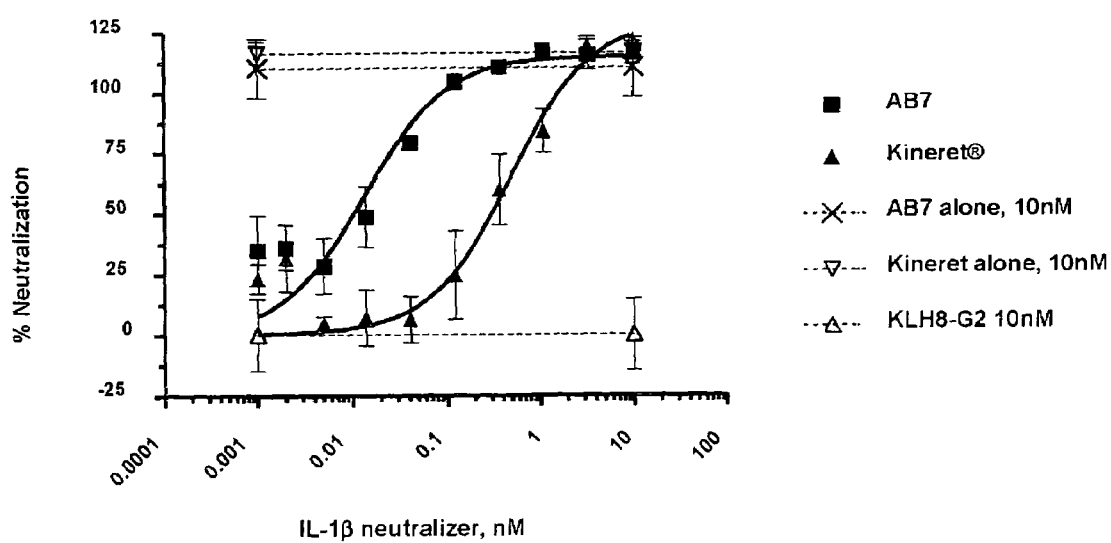
FIG. 18 is a graph showing the results of an in vitro experiment for the antibody designated AB7 and for Kineret involving IL-1 induced production of IL-8.

Fresh, heparinized peripheral blood was collected from healthy donors. 180 μl of whole blood was plated in a 96-well plate and incubated with various concentrations of the antibody AB7 and 100 pM rhIL-1β. For Kineret®-treated samples, Kineret® and rhIL-1β were combined 1:1 prior to mixing with blood. Samples were incubated for 6 hours at 37° C. with 5% $CO_2$. Whole blood cells were then lysed with 50 μl 2.5% Triton X-100. The concentration of interleukin-8 (IL-8) in cleared lysates was assayed by ELISA (Quantikine human IL-8 ELISA kit, R&D Systems) according to manufacturer's instructions. IL-8 concentrations in AB7 and Kineret® treated samples were compared to a control sample treated with anti-KLH control. The results are depicted in FIG. 18 and summarized in Table 6. $IC_{50}$ is the concentration of antibody required to inhibit 50% of IL-8 released by IL-1β stimulation.

TABLE 6

|  | $IC_{50}$ (pM) |
|---|---|
| AB7 | 1.9 pM |
| Kineret ® | 53.4 pM |

These results demonstrate the in vitro potency of the AB7, as measured by inhibition of IL-1β stimulated release of IL-8. These results showing greater potency compared with Kineret® indicate that the antibodies of the invention will have IL-1β inhibitory efficacy in vivo.

Example 13

This example illustrates that the antibodies of the invention have surprisingly high affinity in comparison to an antibody having a similar sequence.

AB5 was compared to AB-control in terms of sequence and binding affinity. AB5 comprises the heavy chain variable region set forth in SEQ ID NO:8 and the light chain variable region set forth in SEQ ID NO:9. AB-control is believed to comprise the heavy chain variable region set forth in SEQ ID NO:38 and the light chain variable region set forth in SEQ ID NO:39. Those sequence set forth in U.S. Patent Application Publication No. 2003/0026806, at FIGS. 6A and 6B. AB5 and AB-control have the same complementarity determining regions in their heavy and light chain variable regions. Their heavy chains differ by three amino acid residues in framework region 3, located at positions 68, 74 and 86 in SEQ ID NOS: 8 and 38. Their respective light chains differ by one amino acid residue in framework region 3, located at position 72 in SEQ ID NOS: 9 and 39. Despite the similarities in the sequences of their heavy and light chain variable regions, including the same CDRs, AB5 and AB-control differ significantly and unexpectedly in their binding affinity. As discussed in Examples 1 and 5 above, AB5 was found to have a dissociation constant of less than 0.3 pM (with a $K_D$-low of 0.11 pM, and a $K_D$-high of 0.56 pM), and AB-control was found to have a dissociation constant of 3 pM (with a $K_D$-low of 1.62 pM, and a $K_D$-high of 5.23 pM). Given the similarities in amino acid sequence, it is surprising that AB5 has higher affinity by an order of magnitude.

AB7 was generated using HUMAN ENGINEERING™ technology, as described in Example 4. The light and heavy chain variable regions of AB7 include low and moderate risk positions in the sequences of light and heavy chain variable regions AB5. AB7 comprises the heavy chain variable region set forth in SEQ ID NO:15 and the light chain variable region set forth in SEQ ID NO:11.

AB7 was compared to AB-control and AB5 in terms of sequence and binding affinity. AB7 and AB-control have the same complementarity determining regions in their heavy and light chain variable regions. Their heavy chains differ at two of the three positions in framework region 3 (positions 74 and 86 in SEQ ID NOS: 15 and 38) where AB5 differed from AB-control; however, at position 68 in SEQ ID NO: 15, AB7 has the same amino acid as AB-control. In the light chain of AB7, position 72 in SEQ ID NO: 11 differs from both AB-control and AB5. AB7 includes several other differences in the light and heavy chain variable regions when compared to AB-control and AB5 by virtue of the HUMAN ENGINEERING™ process. Despite the inclusion of changes at moderate risk positions, and particularly in view of the changes in AB7 compared to AB5 at position 68 in the heavy chain variable region and at position 72 in the light chain variable region, AB7 and AB5 have similar dissociation constants, and AB7 differs significantly and unexpectedly from AB-control with respect to binding affinity. As discuss in Example 5 above, AB7 was found to have a dissociation constant of 0.3 pM (with a $K_D$-low of 0.11 pM, and a $K_D$-high of 0.74 pM). AB5 was found to have a dissociation constant of 0.24 pM (with a $K_D$-low of 0.07 pM, and a $K_D$-high of 0.72 pM). Given the changes made in moderate risk positions, and the overall similarities in amino acid sequence, particularly in the CDRs, it is surprising that AB7 has similar affinity to AB5 and higher affinity than AB-control by an order of magnitude.

Example 14

This example shows that at least one antibody of the present invention binds to an IL-1β epitope such that the bound antibody does not substantially prevent the antibody-bound IL-1β from binding to IL-1 receptor type I. This Example employs a Biacore® kinetic analysis instrument to examine whether IL-1β bound to one of the present antibodies (AB7) can still bind to IL-1 receptor type I.

For this Example, AB7 was immobilized on the surface of a CM-5 sensor chip in a Biacore instrument as follows. Using HBS-EP (Biacore®, Inc.) as running buffer, the temperature was set to 25° C., the flow rate was set to 10 µL/min, and the flow path was directed to flow cell 2 only. 135 µL of each of NHS and ECD solutions (Biacore®, Inc.) were mixed, and 70 µL of the NHS/ECD solution was immediately injected in the flow path. Then 91 µL of an AB7 solution (~20 µg/mL in 10 mM sodium acetate buffer (Biacore®, Inc.)) was injected, followed by 70 µL of 1M Ethanolamine (Biacore®, Inc.). Approximately 5650 RU of AB7 was thus immobilized. To prepare a reference surface, the flow path was changed to flow cell 1 only. 135 µL of each of NHS and ECD solutions (Biacore®, Inc.) were mixed, and 70 µL of the NHS/ECD solution was immediately injected in the flow path, followed by 70 µL 1M Ethanolamine (Biacore®, Inc.).

The Biacore® instrument was then ready for the analysis of whether IL-1β bound to AB7 would still bind to IL-1 receptor type I. For this analysis, soluble IL-1 receptor type I (IL-1 sRI) was used, and the binding of IL-1 sRI to a complex of AB7/IL-1β was tested as follows. IL-1 sRI (RnDSystems cat #269-1R-100/CF) and IL-1β (Peprotech, cat #200-01B) were separately diluted to 10 ug/mL in HBS-EP. The flow rate was set to 10 µL/min. The flow path for the Biacore® instrument was set to flow cells 1 and 2, and reference subtraction of flowcell 2 from flowcell 1 was used to determine a response differential. FIG. 19 shows the measured response differential from the Biacore® instrument over the course of the analysis. FIG. 20 provides an illustration of the steps used in the analysis, indicating the separate additions to the flow cell of (A) IL-1 sRI, (B) IL-1β, and (C) IL-1 sRI, in that order.

At 200 seconds, 20 µL of IL-1 sRI was injected to verify absence of binding directly to immobilized AB7 (injection A in FIGS. 19 and 20). As shown in FIG. 19, IL-1 sRI did not increase the response units, which indicates that IL-1 sRI did not bind directly to the immobilized AB7.

At 600 seconds, approximately 1000 RU of IL-1b was bound by AB7, forming a AB7/IL-1β complex on the chip surface (injection B in FIGS. 19 and 20). The increase in response units indicates that the IL-1β bound to the immobilized AB7. 20 µL of IL-1 sRI was next injected at 1200 seconds to test binding of IL-1 sRI to the complex of AB7 and IL-1β. Approximately 1500 RU of IL-1 sRI bound to the AB7/IL-1β complex (injection C in FIGS. 19 and 20). This increase in response units indicates that IL-1 sRI bound to the IL-1β/AB7 complex.

This Example indicates that IL-1 sRI binds to IL-1β but does not bind to AB7, and that AB7 binds to an IL-1β epitope such that the bound AB7 does not substantially prevent the IL-1β from binding to IL-1 sRI.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those working in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated IL-1β binding antibody or IL-1β binding fragment thereof comprising a heavy chain variable region of SEQ ID NO: 15 and a light chain variable region of SEQ ID NO: 11.

2. The antibody or antibody fragment of claim 1, wherein the antibody or antibody fragment comprises a lambda light chain.

3. The antibody or antibody fragment of claim 1, wherein the antibody or antibody fragment comprises an IgG2 region.

4. The antibody or antibody fragment of claim 1, wherein the antibody or antibody fragment is an Fab, an F(ab')2, an Fv.

5. An isolated IL-1β binding antibody or IL-1β binding fragment thereof, wherein the antibody or fragment binds to human IL-1β with a dissociation constant less than 1 pM, and the antibody or fragment competes with the binding of an antibody comprising the light chain variable region of SEQ ID NO: 11 and the heavy chain variable region of SEQ ID NO: 15.

6. A composition comprising (a) the antibody or antibody fragment of claim 1 or 5, and (b) a suitable carrier.

7. The composition of claim 6, wherein the carrier is a pharmaceutically acceptable carrier.

8. The composition of claim 7, wherein the composition is in a form suitable for intraarticular, subcutaneous, intravenous, intraperitoneal, intracerebral, intraparenchymal, intracerebroventricular, intramuscular, intraocular, intraarterial, intralesional, oral or inhalation administration.

9. The composition of claim 7, wherein the composition comprises a lyoprotectant, a surfactant, a filler, a binder, and/or bulking agent.

10. The composition of claim 7, wherein the composition is a controlled-release or sustained-release pharmaceutical composition.

* * * * *

SEQUENCE LISTING

<160> NUMBER OF SEQ ID NOS: 57

<210> SEQ ID NO 1
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: "Xaa" is Thr or Ser
<220> FEATURE:
<221> NAME/KEY: MISC_FEATURE
<222> LOCATION: (15)..(15)
<223> OTHER INFORMATION: "Xaa" is Leu or Val
<220> FEATURE:
<221> NAME/KEY: MISC_FEATURE
<222> LOCATION: (22)..(22)
<223> OTHER INFORMATION: "Xaa" is Thr or Ser
<220> FEATURE:
<221> NAME/KEY: MISC_FEATURE
<222> LOCATION: (41)..(41)
<223> OTHER INFORMATION: "Xaa" is Asp or Gly
<220> FEATURE:
<221> NAME/KEY: MISC_FEATURE
<222> LOCATION: (42)..(42)
<223> OTHER INFORMATION: "Xaa" is Gly or Lys
<220> FEATURE:
<221> NAME/KEY: MISC_FEATURE
<222> LOCATION: (43)..(43)
<223> OTHER INFORMATION: "Xaa" is Thr or Ala
<220> FEATURE:
<221> NAME/KEY: MISC_FEATURE
<222> LOCATION: (72)..(72)
<223> OTHER INFORMATION: "Xaa" is Thr or Ser

<400> SEQUENCE: 1

Asp Ile Gln Met Thr Gln Xaa Thr Ser Ser Leu Ser Ala Ser Xaa Gly
 1               5                  10                  15

Asp Arg Val Thr Ile Xaa Cys Arg Ala Ser Gln Asp Ile Ser Asn Tyr
                20                  25                  30

Leu Ser Trp Tyr Gln Gln Lys Pro Xaa Xaa Xaa Val Lys Leu Leu Ile
            35                  40                  45

Tyr Tyr Thr Ser Lys Leu His Ser Gly Val Pro Ser Arg Phe Ser Gly
        50                  55                  60

Ser Gly Ser Gly Thr Asp Tyr Xaa Leu Thr Ile Ser Asn Leu Glu Gln
65                  70                  75                  80

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 2
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: "Xaa" is Thr or Gln
<220> FEATURE:
<221> NAME/KEY: MISC_FEATURE
<222> LOCATION: (5)..(5)
<223> OTHER INFORMATION: "Xaa" is Lys or Gln
<220> FEATURE:

```
<221> NAME/KEY: MISC_FEATURE
<222> LOCATION: (11)..(11)
<223> OTHER INFORMATION: "Xaa" is Ile or Leu
<220> FEATURE:
<221> NAME/KEY: MISC_FEATURE
<222> LOCATION: (12)..(12)
<223> OTHER INFORMATION: "Xaa" is Leu or Val
<220> FEATURE:
<221> NAME/KEY: MISC_FEATURE
<222> LOCATION: (67)..(67)
<223> OTHER INFORMATION: "Xaa" is Thr or Ser
<220> FEATURE:
<221> NAME/KEY: MISC_FEATURE
<222> LOCATION: (68)..(68)
<223> OTHER INFORMATION: "Xaa" is Gln or Arg
<220> FEATURE:
<221> NAME/KEY: MISC_FEATURE
<222> LOCATION: (77)..(77)
<223> OTHER INFORMATION: "Xaa" is Arg or Lys
<220> FEATURE:
<221> NAME/KEY: MISC_FEATURE
<222> LOCATION: (81)..(81)
<223> OTHER INFORMATION: "Xaa" is Phe or Ser
<220> FEATURE:
<221> NAME/KEY: MISC_FEATURE
<222> LOCATION: (88)..(88)
<223> OTHER INFORMATION: "Xaa" is Asp or Thr
<220> FEATURE:
<221> NAME/KEY: MISC_FEATURE
<222> LOCATION: (89)..(89)
<223> OTHER INFORMATION: "Xaa" is Thr or Ala
<220> FEATURE:
<221> NAME/KEY: MISC_FEATURE
<222> LOCATION: (90)..(90)
<223> OTHER INFORMATION: "Xaa" is Val or Ala
<220> FEATURE:
<221> NAME/KEY: MISC_FEATURE
<222> LOCATION: (94)..(94)
<223> OTHER INFORMATION: "Xaa" is Thr or Val
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 2

Gln Val Xaa Leu Xaa Glu Ser Gly Pro Gly Xaa Xaa Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Xaa Xaa Leu Thr Ile Ser Lys Asp Thr Ser Xaa Asn Gln Val
65                  70                  75                  80

Xaa Leu Lys Ile Thr Ser Val Xaa Xaa Xaa Asp Thr Ala Xaa Tyr Phe
                85                  90                  95

Cys Ala Arg Xaa Xaa Tyr Asp Pro Pro Trp Phe Val Trp Gly Gln
            100                 105                 110

Gly Thr Leu Val Thr Val Ser Ser
        115                 120

<210> SEQ ID NO 3
<211> LENGTH: 10
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: "Xaa" is Ala, Val, Phe, Lys, or Asn
<220> FEATURE:
<221> NAME/KEY: MISC_FEATURE
<222> LOCATION: (2)..(2)
<223> OTHER INFORMATION: "Xaa" is Arg or Lys

<400> SEQUENCE: 3

Xaa Xaa Tyr Asp Pro Pro Trp Phe Val Asp
1               5                   10

<210> SEQ ID NO 4
<211> LENGTH: 120
<212> TYPE: PRT
<213> ORGANISM: Artificial
<220> FEATURE:
<223> OTHER INFORMATION: Synthetic

<400> SEQUENCE: 4

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Ala Arg Tyr Asp Pro Pro Trp Phe Val Asp Trp Gly Gln
            100                 105                 110

Gly Thr Leu Val Thr Val Ser Ser
        115                 120

<210> SEQ ID NO 5
<211> LENGTH: 120
<212> TYPE: PRT
<213> ORGANISM: Artificial
<220> FEATURE:
<223> OTHER INFORMATION: Synthetic

<400> SEQUENCE: 5

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Val Arg Tyr Asp Pro Pro Trp Phe Val Asp Trp Gly Gln
```

Gly Thr Leu Val Thr Val Ser Ser
        115                 120

<210> SEQ ID NO 6
<211> LENGTH: 120
<212> TYPE: PRT
<213> ORGANISM: Artificial
<220> FEATURE:
<223> OTHER INFORMATION: Synthetic

<400> SEQUENCE: 6

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Phe Arg Tyr Asp Pro Pro Trp Phe Val Asp Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial
<220> FEATURE:
<223> OTHER INFORMATION: Synthetic

<400> SEQUENCE: 7

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Lys Lys Tyr Asp Pro Pro Trp Phe Val Asp Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial
<220> FEATURE:

-continued

<223> OTHER INFORMATION: Synthetic

<400> SEQUENCE: 8

```
Gln Val Thr Leu Lys Glu Ser Gly Pro Gly Ile Leu Lys Pro Ser Gln
1               5                   10                  15
Thr Leu Ser Leu Thr Cys Ser Phe Ser Gly Phe Ser Leu Ser Thr Ser
            20                  25                  30
Gly Met Gly Val Gly Trp Ile Arg Gln Pro Ser Gly Lys Gly Leu Glu
        35                  40                  45
Trp Leu Ala His Ile Trp Trp Asp Gly Asp Glu Ser Tyr Asn Pro Ser
    50                  55                  60
Leu Lys Thr Gln Leu Thr Ile Ser Lys Asp Thr Ser Arg Asn Gln Val
65                  70                  75                  80
Phe Leu Lys Ile Thr Ser Val Asp Thr Val Asp Thr Ala Thr Tyr Phe
                85                  90                  95
Cys Ala Arg Asn Arg Tyr Asp Pro Pro Trp Phe Val Asp Trp Gly Gln
            100                 105                 110
Gly Thr Leu Val Thr Val Ser Ser
        115                 120
```

<210> SEQ ID NO 9
<211> LENGTH: 107
<212> TYPE: PRT
<213> ORGANISM: Artificial
<220> FEATURE:
<223> OTHER INFORMATION: Synthetic

<400> SEQUENCE: 9

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
            20                  25                  30
Leu Ser Trp Tyr Gln Gln Lys Pro Asp Gly Thr Val Lys Leu Leu Ile
        35                  40                  45
Tyr Tyr Thr Ser Lys Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Leu Gln Gly Lys Met Leu Pro Trp
                85                  90                  95
Thr Phe Gly Gly Gly Thr Lys Leu Glu Ile Lys
            100                 105
```

<210> SEQ ID NO 10
<211> LENGTH: 107
<212> TYPE: PRT
<213> ORGANISM: Artificial
<220> FEATURE:
<223> OTHER INFORMATION: Synthetic

<400> SEQUENCE: 10

```
Asp Ile Gln Met Thr Gln Ser Thr Ser Ser Leu Ser Ala Ser Leu Gly
1               5                   10                  15
Asp Arg Val Thr Ile Thr Cys Arg Ala Ser Gln Asp Ile Ser Asn Tyr
            20                  25                  30
Leu Ser Trp Tyr Gln Gln Lys Pro Gly Lys Thr Val Lys Leu Leu Ile
        35                  40                  45
Tyr Tyr Thr Ser Lys Leu His Ser Gly Val Pro Ser Arg Phe Ser Gly
```

```
                    50                  55                  60
Ser Gly Ser Gly Thr Asp Tyr Thr Leu Thr Ile Ser Ser Leu Gln Gln
 65                  70                  75                  80

Glu Asp Phe Ala Thr Tyr Phe Cys Leu Gln Gly Lys Met Leu Pro Trp
                    85                  90                  95

Thr Phe Gly Gln Gly Thr Lys Leu Glu Ile Lys
                100                 105

<210> SEQ ID NO 11
<211> LENGTH: 107
<212> TYPE: PRT
<213> ORGANISM: Artificial
<220> FEATURE:
<223> OTHER INFORMATION: Synthetic

<400> SEQUENCE: 11

Asp Ile Gln Met Thr Gln Ser Thr Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Ser Trp Tyr Gln Gln Lys Pro Gly Lys Ala Val Lys Leu Leu Ile
            35                  40                  45

Tyr Tyr Thr Ser Lys Leu His Ser Gly Val Pro Ser Arg Phe Ser Gly
        50                  55                  60

Ser Gly Ser Gly Thr Asp Tyr Thr Leu Thr Ile Ser Ser Leu Gln Gln
 65                  70                  75                  80

Glu Asp Phe Ala Thr Tyr Phe Cys Leu Gln Gly Lys Met Leu Pro Trp
                    85                  90                  95

Thr Phe Gly Gln Gly Thr Lys Leu Glu Ile Lys
                100                 105

<210> SEQ ID NO 12
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 12

Gln Val Gln Leu Gln Glu Ser Gly Pro Gly Leu Leu Lys Pro Ser Gln
 1               5                  10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Gly Asp Glu Ser Tyr Asn Pro Ser
        50                  55                  60

Leu Lys Ser Gln Leu Thr Ile Ser Lys Asp Thr Ser Lys Asn Gln Val
 65                  70                  75                  80

Ser Leu Lys Ile Thr Ser Val Thr Ala Ala Asp Thr Ala Thr Tyr Phe
                    85                  90                  95

Cys Ala Arg Xaa Xaa Tyr Asp Pro Pro Trp Phe Val Asp Trp Gly Gln
```

```
                    100             105             110
Gly Thr Leu Val Thr Val Ser Ser
        115             120

<210> SEQ ID NO 13
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
        115             120

<210> SEQ ID NO 14
<211> LENGTH: 120
<212> TYPE: PRT
<213> ORGANISM: Artificial
<220> FEATURE:
<223> OTHER INFORMATION: Synthetic

<400> SEQUENCE: 14

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asp Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
```

<210> SEQ ID NO 15
<211> LENGTH: 120
<212> TYPE: PRT
<213> ORGANISM: Artificial
<220> FEATURE:
<223> OTHER INFORMATION: Synthetic

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Ala Arg Tyr Asp Pro Pro Trp Phe Val Asp
1               5                   10

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

Val Arg Tyr Asp Pro Pro Trp Phe Val Asp
1               5                   10

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Phe Arg Tyr Asp Pro Pro Trp Phe Val Asp
1               5                   10

<210> SEQ ID NO 19
<211> LENGTH: 10
<212> TYPE: PRT

```
<213> ORGANISM: Artificial
<220> FEATURE:
<223> OTHER INFORMATION: Synthetic

<400> SEQUENCE: 19

Lys Lys Tyr Asp Pro Pro Trp Phe Val Asp
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Asn Arg Tyr Asp Pro Pro Trp Phe Val Asp
1               5                   10

<210> SEQ ID NO 21
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 21

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Gln Leu Thr Ile Ser Lys Asp Thr Ser Arg Asn Gln Val
65                  70                  75                  80

Phe Leu Lys Ile Thr Ser Val Asp Thr Val Asp Thr Ala Thr Tyr Phe
                85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
            115                 120

<210> SEQ ID NO 22
<211> LENGTH: 8
<212> TYPE: PRT
<213> ORGANISM: Artificial
<220> FEATURE:
<223> OTHER INFORMATION: Synthetic

<400> SEQUENCE: 22

Tyr Asp Pro Pro Trp Phe Val Asp
1               5

<210> SEQ ID NO 23
```

```
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 23

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Xaa Xaa Tyr Asp Pro Pro Trp Phe Val Asp Trp Gly Gln
            100                 105                 110
```

Gly Thr Leu Val Thr Val Ser Ser
        115                 120

<210> SEQ ID NO 25
<211> LENGTH: 120
<212> TYPE: PRT
<213> ORGANISM: Artificial
<220> FEATURE:
<223> OTHER INFORMATION: Synthetic

<400> SEQUENCE: 25

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 26
<211> LENGTH: 120
<212> TYPE: PRT
<213> ORGANISM: Artificial
<220> FEATURE:
<223> OTHER INFORMATION: Synthetic

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 27
<211> LENGTH: 107
<212> TYPE: PRT
<213> ORGANISM: Artificial
<220> FEATURE:
<223> OTHER INFORMATION: Synthetic
<220> FEATURE:

```
<221> NAME/KEY: MISC_FEATURE
<222> LOCATION: (7)..(7)
<223> OTHER INFORMATION: "Xaa" is Thr or Ser
<220> FEATURE:
<221> NAME/KEY: MISC_FEATURE
<222> LOCATION: (15)..(15)
<223> OTHER INFORMATION: "Xaa" is Leu or Val
<220> FEATURE:
<221> NAME/KEY: MISC_FEATURE
<222> LOCATION: (22)..(22)
<223> OTHER INFORMATION: "Xaa" is Thr or Ser
<220> FEATURE:
<221> NAME/KEY: MISC_FEATURE
<222> LOCATION: (41)..(41)
<223> OTHER INFORMATION: "Xaa" is Asp or Gly
<220> FEATURE:
<221> NAME/KEY: MISC_FEATURE
<222> LOCATION: (42)..(42)
<223> OTHER INFORMATION: "Xaa" is Gly or Lys
<220> FEATURE:
<221> NAME/KEY: MISC_FEATURE
<222> LOCATION: (43)..(43)
<223> OTHER INFORMATION: "Xaa" is Thr or Ala
<220> FEATURE:
<221> NAME/KEY: MISC_FEATURE
<222> LOCATION: (72)..(72)
<223> OTHER INFORMATION: "Xaa" is Thr or Ser
<220> FEATURE:
<221> NAME/KEY: MISC_FEATURE
<222> LOCATION: (77)..(77)
<223> OTHER INFORMATION: "Xaa" is Asn or Ser
<220> FEATURE:
<221> NAME/KEY: MISC_FEATURE
<222> LOCATION: (79)..(79)
<223> OTHER INFORMATION: "Xaa" is Glu or Gln
<220> FEATURE:
<221> NAME/KEY: MISC_FEATURE
<222> LOCATION: (83)..(83)
<223> OTHER INFORMATION: "Xaa" is Ile or Phe
<220> FEATURE:
<221> NAME/KEY: MISC_FEATURE
<222> LOCATION: (100)..(100)
<223> OTHER INFORMATION: "Xaa" is Gly or Gln

<400> SEQUENCE: 27

Asp Ile Gln Met Thr Gln Xaa Thr Ser Ser Leu Ser Ala Ser Xaa Gly
1               5                   10                  15

Asp Arg Val Thr Ile Xaa Cys Arg Ala Ser Gln Asp Ile Ser Asn Tyr
            20                  25                  30

Leu Ser Trp Tyr Gln Gln Lys Pro Xaa Xaa Xaa Val Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Xaa Leu Thr Ile Ser Xaa Leu Xaa Gln
65                  70                  75                  80

Glu Asp Xaa Ala Thr Tyr Phe Cys Leu Gln Gly Lys Met Leu Pro Trp
                85                  90                  95

Thr Phe Gly Xaa Gly Thr Lys Leu Glu Ile Lys
            100                 105

<210> SEQ ID NO 28
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: "Xaa" is Thr or Gln
<220> FEATURE:
```

```
<221> NAME/KEY: MISC_FEATURE
<222> LOCATION: (5)..(5)
<223> OTHER INFORMATION: "Xaa" is Lys or Gln
<220> FEATURE:
<221> NAME/KEY: MISC_FEATURE
<222> LOCATION: (11)..(11)
<223> OTHER INFORMATION: "Xaa" is Ile or Leu
<220> FEATURE:
<221> NAME/KEY: MISC_FEATURE
<222> LOCATION: (12)..(12)
<223> OTHER INFORMATION: "Xaa" is Leu or Val
<220> FEATURE:
<221> NAME/KEY: MISC_FEATURE
<222> LOCATION: (67)..(67)
<223> OTHER INFORMATION: "Xaa" is Thr or Ser
<220> FEATURE:
<221> NAME/KEY: MISC_FEATURE
<222> LOCATION: (68)..(68)
<223> OTHER INFORMATION: "Xaa" is Gln or Arg
<220> FEATURE:
<221> NAME/KEY: MISC_FEATURE
<222> LOCATION: (74)..(74)
<223> OTHER INFORMATION: "Xaa" is Asp or Asn
<220> FEATURE:
<221> NAME/KEY: MISC_FEATURE
<222> LOCATION: (77)..(77)
<223> OTHER INFORMATION: "Xaa" is Arg or Lys
<220> FEATURE:
<221> NAME/KEY: MISC_FEATURE
<222> LOCATION: (81)..(81)
<223> OTHER INFORMATION: "Xaa" is Phe or Ser
<220> FEATURE:
<221> NAME/KEY: MISC_FEATURE
<222> LOCATION: (88)..(88)
<223> OTHER INFORMATION: "Xaa" is Asp or Thr
<220> FEATURE:
<221> NAME/KEY: MISC_FEATURE
<222> LOCATION: (89)..(89)
<223> OTHER INFORMATION: "Xaa" is Thr or Ala
<220> FEATURE:
<221> NAME/KEY: MISC_FEATURE
<222> LOCATION: (90)..(90)
<223> OTHER INFORMATION: "Xaa" is Val or Ala
<220> FEATURE:
<221> NAME/KEY: MISC_FEATURE
<222> LOCATION: (94)..(94)
<223> OTHER INFORMATION: "Xaa" is Thr or Val
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys

<400> SEQUENCE: 28

Gln Val Xaa Leu Xaa Glu Ser Gly Pro Gly Xaa Xaa Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Xaa Xaa Leu Thr Ile Ser Lys Xaa Thr Ser Xaa Asn Gln Val
65                  70                  75                  80

Xaa Leu Lys Ile Thr Ser Val Xaa Xaa Asp Thr Ala Xaa Tyr Phe
                85                  90                  95

Cys Ala Arg Xaa Xaa Tyr Asp Pro Pro Trp Phe Val Asp Trp Gly Gln
            100                 105                 110
```

Gly Thr Leu Val Thr Val Ser Ser
          115                 120

<210> SEQ ID NO 29
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: "Xaa" is Thr or Gln
<220> FEATURE:
<221> NAME/KEY: MISC_FEATURE
<222> LOCATION: (5)..(5)
<223> OTHER INFORMATION: "Xaa" is Lys or Gln
<220> FEATURE:
<221> NAME/KEY: MISC_FEATURE
<222> LOCATION: (11)..(11)
<223> OTHER INFORMATION: "Xaa" is Ile or Leu
<220> FEATURE:
<221> NAME/KEY: MISC_FEATURE
<222> LOCATION: (12)..(12)
<223> OTHER INFORMATION: "Xaa" is Leu or Val
<220> FEATURE:
<221> NAME/KEY: MISC_FEATURE
<222> LOCATION: (67)..(67)
<223> OTHER INFORMATION: "Xaa" is Thr or Ser
<220> FEATURE:
<221> NAME/KEY: MISC_FEATURE
<222> LOCATION: (68)..(68)
<223> OTHER INFORMATION: "Xaa" is Gln or Arg
<220> FEATURE:
<221> NAME/KEY: MISC_FEATURE
<222> LOCATION: (74)..(74)
<223> OTHER INFORMATION: "Xaa" is Asp or Asn
<220> FEATURE:
<221> NAME/KEY: MISC_FEATURE
<222> LOCATION: (77)..(77)
<223> OTHER INFORMATION: "Xaa" is Arg or Lys
<220> FEATURE:
<221> NAME/KEY: MISC_FEATURE
<222> LOCATION: (81)..(81)
<223> OTHER INFORMATION: "Xaa" is Phe or Ser
<220> FEATURE:
<221> NAME/KEY: MISC_FEATURE
<222> LOCATION: (88)..(88)
<223> OTHER INFORMATION: "Xaa" is Asp or Thr
<220> FEATURE:
<221> NAME/KEY: MISC_FEATURE
<222> LOCATION: (89)..(89)
<223> OTHER INFORMATION: "Xaa" is Thr or Ala
<220> FEATURE:
<221> NAME/KEY: MISC_FEATURE
<222> LOCATION: (90)..(90)
<223> OTHER INFORMATION: "Xaa" is Val or Ala
<220> FEATURE:
<221> NAME/KEY: MISC_FEATURE
<222> LOCATION: (94)..(94)
<223> OTHER INFORMATION: "Xaa" is Thr or Val
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 29

Gln Val Xaa Leu Xaa Glu Ser Gly Pro Gly Xaa Xaa Lys Pro Ser Gln
1               5                   10                  15

Thr Leu Ser Leu Thr Cys Ser Phe Ser Gly Phe Ser Leu Ser Thr Ser
            20                  25                  30

```
Gly Met Gly Val Gly Trp Ile Arg Gln Pro Ser Gly Lys Gly Leu Glu
            35                  40                  45

Trp Leu Ala His Ile Trp Trp Asp Gly Asp Glu Ser Tyr Asn Pro Ser
 50                  55                  60

Leu Lys Xaa Xaa Leu Thr Ile Ser Lys Xaa Thr Ser Xaa Asn Gln Val
 65              70                  75                  80

Xaa Leu Lys Ile Thr Ser Val Xaa Xaa Xaa Asp Thr Ala Xaa Tyr Phe
                 85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
            115                 120

<210> SEQ ID NO 30
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: "Xaa" is Ala, Val, Phe, Lys, or Asn
<220> FEATURE:
<221> NAME/KEY: MISC_FEATURE
<222> LOCATION: (2)..(2)
<223> OTHER INFORMATION: "Xaa" is Arg or Lys, but is not Lys if position
      (1) is Lys

<400> SEQUENCE: 30

Xaa Xaa Tyr Asp Pro Pro Trp Phe Val Asp
 1               5                  10

<210> SEQ ID NO 31
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 31

Gln Val Gln Leu Gln Glu Ser Gly Pro Gly Leu Leu Lys Pro Ser Gln
 1               5                  10                  15

Thr Leu Ser Leu Thr Cys Ser Phe Ser Gly Phe Ser Leu Ser Thr Ser
             20                  25                  30

Gly Met Gly Val Gly Trp Ile Arg Gln Pro Ser Gly Lys Gly Leu Glu
            35                  40                  45

Trp Leu Ala His Ile Trp Trp Asp Gly Asp Glu Ser Tyr Asn Pro Ser
 50                  55                  60

Leu Lys Ser Gln Leu Thr Ile Ser Lys Asp Thr Ser Lys Asn Gln Val
 65              70                  75                  80

Ser Leu Lys Ile Thr Ser Val Thr Ala Ala Asp Thr Ala Thr Tyr Phe
                 85                  90                  95

Cys Ala Arg Xaa Xaa Tyr Asp Pro Pro Trp Phe Val Asp Trp Gly Gln
```

```
                    100                 105                 110
Gly Thr Leu Val Thr Val Ser Ser
            115                 120

<210> SEQ ID NO 32
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
            85                  90                  95

Cys Ala Arg Xaa Xaa Tyr Asp Pro Pro Trp Phe Val Asp Trp Gly Gln
        100                 105                 110

Gly Thr Leu Val Thr Val Ser Ser
            115                 120

<210> SEQ ID NO 33
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 33

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60
```

```
Leu Lys Thr Gln Leu Thr Ile Ser Lys Asp Thr Ser Arg Asn Gln Val
 65                  70                  75                  80

Phe Leu Lys Ile Thr Ser Val Asp Thr Val Asp Ala Thr Tyr Phe
                 85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
            115                 120

<210> SEQ ID NO 34
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 34

Gln Val Gln Leu Gln Glu Ser Gly Pro Gly Leu Leu Lys Pro Ser Gln
  1               5                  10                  15

Thr Leu Ser Leu Thr Cys Ser Phe Ser Gly Phe Ser Leu Ser Thr Ser
                 20                  25                  30

Gly Met Gly Val Gly Trp Ile Arg Gln Pro Ser Gly Lys Gly Leu Glu
             35                  40                  45

Trp Leu Ala His Ile Trp Trp Asp Gly Asp Glu Ser Tyr Asn Pro Ser
 50                  55                  60

Leu Lys Ser Gln Leu Thr Ile Ser Lys Asn Thr Ser Lys Asn Gln Val
 65                  70                  75                  80

Ser Leu Lys Ile Thr Ser Val Thr Ala Ala Asp Thr Ala Thr Tyr Phe
                 85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
            115                 120

<210> SEQ ID NO 35
<211> LENGTH: 120
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (100)..(100)
<223> OTHER INFORMATION: "Xaa" is Ala, Val, Phe, Lys, or Asn
<220> FEATURE:
<221> NAME/KEY: MISC_FEATURE
<222> LOCATION: (101)..(101)
<223> OTHER INFORMATION: "Xaa" is Arg or Lys, but is not Lys if position
      (100) is Lys

<400> SEQUENCE: 35

Gln Val Gln Leu Gln Glu Ser Gly Pro Gly Leu Val Lys Pro Ser Gln
  1               5                  10                  15

Thr Leu Ser Leu Thr Cys Ser Phe Ser Gly Phe Ser Leu Ser Thr Ser
                 20                  25                  30
```

```
Gly Met Gly Val Gly Trp Ile Arg Gln Pro Ser Gly Lys Gly Leu Glu
            35                  40                  45

Trp Leu Ala His Ile Trp Trp Asp Gly Asp Glu Ser Tyr Asn Pro Ser
        50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Xaa Xaa Tyr Asp Pro Pro Trp Phe Val Asp Trp Gly Gln
            100                 105                 110

Gly Thr Leu Val Thr Val Ser Ser
        115                 120

<210> SEQ ID NO 36
<211> LENGTH: 23
<212> TYPE: PRT
<213> ORGANISM: Homo Sapiens

<400> SEQUENCE: 36

Glu Ser Val Asp Pro Lys Asn Tyr Pro Lys Lys Met Glu Lys Arg
1               5                   10                  15

Phe Val Phe Asn Lys Ile Glu
            20

<210> SEQ ID NO 37
<211> LENGTH: 5
<212> TYPE: PRT
<213> ORGANISM: Artificial
<220> FEATURE:
<223> OTHER INFORMATION: Linker Sequence

<400> SEQUENCE: 37

Gly Gly Gly Gly Ser
1               5

<210> SEQ ID NO 38
<211> LENGTH: 360
<212> TYPE: DNA
<213> ORGANISM: Artificial
<220> FEATURE:
<223> OTHER INFORMATION: Synthetic

<400> SEQUENCE: 38
caagtacaac ttcaagaaag cggtccaggc cttgttaaac cctcccaaac tctttctctt      60
acctgttctt tctctggatt ctctctctct acctctggca tgggcgtcgg ctggatacgt     120
caaccaagtg gaaaaggact cgaatggctt gcacatatat ggtgggatgg cgacgaatct     180
tataaccctt ctcttaaatc tcgacttaca atttctaaag acacttccaa aaaccaagtt     240
tccctcaaaa taacctccgt cactgctgca gatactgctg tctattttg cgcacgaaac      300 agatatgatc cccctggtt cgttgattgg ggccaaggaa cactcgtaac cgttagctca     360

<210> SEQ ID NO 39
<211> LENGTH: 321
<212> TYPE: DNA
<213> ORGANISM: Artificial
<220> FEATURE:
<223> OTHER INFORMATION: Synthetic

<400> SEQUENCE: 39
gacatccaaa tgactcaatc cacttcctca ctctcagcct ctgtcggaga ccgtgtaact      60
```

```
atcacctgcc gtgcttccca agacatctct aattatctct cctggtatca acaaaaacct    120
ggtaaagctg ttaaacttct catttattat acttctaaac ttcactccgg tgtgccttct    180
cgtttctcag gatcaggctc aggaaccgac tatacactca ccatctcctc cctccaacaa    240
gaagacttcg ctacttactt ttgccttcaa ggaaaaatgc tccctggac tttcggacaa     300 ggaacaaagc tcgaaattaa a                                              321
```

<210> SEQ ID NO 40
<211> LENGTH: 120
<212> TYPE: PRT
<213> ORGANISM: Artificial
<220> FEATURE:
<223> OTHER INFORMATION: Synthetic

<400> SEQUENCE: 40

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Thr Arg Leu Thr Ile Ser Lys Asn Thr Ser Arg Asn Gln Val
65                  70                  75                  80

Phe Leu Lys Ile Thr Thr Val Asp Thr Val Asp Thr Ala Thr Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 41
<211> LENGTH: 107
<212> TYPE: PRT
<213> ORGANISM: Artificial
<220> FEATURE:
<223> OTHER INFORMATION: Synthetic

<400> SEQUENCE: 41

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Phe Leu Thr Ile Ser Asn Leu Glu Gln
65                  70                  75                  80

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 42
<211> LENGTH: 120

```
<212> TYPE: PRT
<213> ORGANISM: Artificial
<220> FEATURE:
<223> OTHER INFORMATION: Synthetic

<400> SEQUENCE: 42

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asp Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Ala Arg Tyr Asp Pro Pro Trp Phe Val Asp Trp Gly Gln
            100                 105                 110

Gly Thr Leu Val Thr Val Ser Ser
        115                 120

<210> SEQ ID NO 43
<211> LENGTH: 120
<212> TYPE: PRT
<213> ORGANISM: Artificial
<220> FEATURE:
<223> OTHER INFORMATION: Synthetic

<400> SEQUENCE: 43

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asp Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Val Arg Tyr Asp Pro Pro Trp Phe Val Asp Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial
<220> FEATURE:
<223> OTHER INFORMATION: Synthetic

<400> SEQUENCE: 44

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
```

```
                    20                  25                  30
Gly Met Gly Val Gly Trp Ile Arg Gln Pro Ser Gly Lys Gly Leu Glu
            35                  40                  45
Trp Leu Ala His Ile Trp Trp Asp Gly Asp Glu Ser Tyr Asn Pro Ser
        50                  55                  60
Leu Lys Ser Gln Leu Thr Ile Ser Lys Asp Thr Ser Lys Asn Gln Val
 65                  70                  75                  80
Ser Leu Lys Ile Thr Ser Val Thr Ala Ala Asp Thr Ala Thr Tyr Phe
                    85                  90                  95
Cys Ala Arg Phe Arg Tyr Asp Pro Pro Trp Phe Val Asp Trp Gly Gln
                100                 105                 110
Gly Thr Leu Val Thr Val Ser Ser
            115                 120

<210> SEQ ID NO 45
<211> LENGTH: 120
<212> TYPE: PRT
<213> ORGANISM: Artificial
<220> FEATURE:
<223> OTHER INFORMATION: Synthetic

<400> SEQUENCE: 45

Gln Val Gln Leu Gln Glu Ser Gly Pro Gly Leu Leu Lys Pro Ser Gln
 1               5                  10                  15
Thr Leu Ser Leu Thr Cys Ser Phe Ser Gly Phe Ser Leu Ser Thr Ser
                20                  25                  30
Gly Met Gly Val Gly Trp Ile Arg Gln Pro Ser Gly Lys Gly Leu Glu
            35                  40                  45
Trp Leu Ala His Ile Trp Trp Asp Gly Asp Glu Ser Tyr Asn Pro Ser
        50                  55                  60
Leu Lys Ser Gln Leu Thr Ile Ser Lys Asp Thr Ser Lys Asn Gln Val
 65                  70                  75                  80
Ser Leu Lys Ile Thr Ser Val Thr Ala Ala Asp Thr Ala Thr Tyr Phe
                    85                  90                  95
Cys Ala Arg Lys Lys Tyr Asp Pro Pro Trp Phe Val Asp Trp Gly Gln
                100                 105                 110
Gly Thr Leu Val Thr Val Ser Ser
            115                 120

<210> SEQ ID NO 46
<211> LENGTH: 120
<212> TYPE: PRT
<213> ORGANISM: Artificial
<220> FEATURE:
<223> OTHER INFORMATION: Synthetic

<400> SEQUENCE: 46

Gln Val Gln Leu Gln Glu Ser Gly Pro Gly Leu Val Lys Pro Ser Gln
 1               5                  10                  15
Thr Leu Ser Leu Thr Cys Ser Phe Ser Gly Phe Ser Leu Ser Thr Ser
                20                  25                  30
Gly Met Gly Val Gly Trp Ile Arg Gln Pro Ser Gly Lys Gly Leu Glu
            35                  40                  45
Trp Leu Ala His Ile Trp Trp Asp Gly Asp Glu Ser Tyr Asn Pro Ser
        50                  55                  60
Leu Lys Ser Arg Leu Thr Ile Ser Lys Asp Thr Ser Lys Asn Gln Val
 65                  70                  75                  80
```

```
Ser Leu Lys Ile Thr Ser Val Thr Ala Ala Asp Thr Ala Val Tyr Phe
            85                  90                  95

Cys Ala Arg Ala Arg Tyr Asp Pro Pro Trp Phe Val Asp Trp Gly Gln
           100                 105                 110

Gly Thr Leu Val Thr Val Ser Ser
       115                 120

<210> SEQ ID NO 47
<211> LENGTH: 120
<212> TYPE: PRT
<213> ORGANISM: Artificial
<220> FEATURE:
<223> OTHER INFORMATION: Synthetic

<400> SEQUENCE: 47

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
            85                  90                  95

Cys Ala Arg Val Arg Tyr Asp Pro Pro Trp Phe Val Asp Trp Gly Gln
           100                 105                 110

Gly Thr Leu Val Thr Val Ser Ser
       115                 120

<210> SEQ ID NO 48
<211> LENGTH: 120
<212> TYPE: PRT
<213> ORGANISM: Artificial
<220> FEATURE:
<223> OTHER INFORMATION: Synthetic

<400> SEQUENCE: 48

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
            85                  90                  95

Cys Ala Arg Phe Arg Tyr Asp Pro Pro Trp Phe Val Asp Trp Gly Gln
           100                 105                 110

Gly Thr Leu Val Thr Val Ser Ser
       115                 120

<210> SEQ ID NO 49
```

```
<211> LENGTH: 120
<212> TYPE: PRT
<213> ORGANISM: Artificial
<220> FEATURE:
<223> OTHER INFORMATION: Synthetic

<400> SEQUENCE: 49

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Lys Lys Tyr Asp Pro Pro Trp Phe Val Asp Trp Gly Gln
            100                 105                 110

Gly Thr Leu Val Thr Val Ser Ser
        115                 120

<210> SEQ ID NO 50
<211> LENGTH: 120
<212> TYPE: PRT
<213> ORGANISM: Artificial
<220> FEATURE:
<223> OTHER INFORMATION: Synthetic

<400> SEQUENCE: 50

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Ala Arg Tyr Asp Pro Pro Trp Phe Val Asp Trp Gly Gln
            100                 105                 110

Gly Thr Leu Val Thr Val Ser Ser
        115                 120

<210> SEQ ID NO 51
<211> LENGTH: 120
<212> TYPE: PRT
<213> ORGANISM: Artificial
<220> FEATURE:
<223> OTHER INFORMATION: Synthetic

<400> SEQUENCE: 51

Gln Val Gln Leu Gln Glu Ser Gly Pro Gly Leu Leu Lys Pro Ser Gln
1               5                   10                  15
```

```
Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Val Arg Tyr Asp Pro Pro Trp Phe Val Asp Trp Gly Gln
                100                 105                 110

Gly Thr Leu Val Thr Val Ser Ser
        115                 120

<210> SEQ ID NO 52
<211> LENGTH: 120
<212> TYPE: PRT
<213> ORGANISM: Artificial
<220> FEATURE:
<223> OTHER INFORMATION: Synthetic

<400> SEQUENCE: 52

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80

Ser Leu Lys Ile Thr Ser Val Thr Ala Ala Asp Thr Ala Thr Tyr Phe
                85                  90                  95

Cys Ala Arg Phe Arg Tyr Asp Pro Pro Trp Phe Val Asp Trp Gly Gln
                100                 105                 110

Gly Thr Leu Val Thr Val Ser Ser
        115                 120

<210> SEQ ID NO 53
<211> LENGTH: 120
<212> TYPE: PRT
<213> ORGANISM: Artificial
<220> FEATURE:
<223> OTHER INFORMATION: Synthetic

<400> SEQUENCE: 53

Gln Val Gln Leu Gln Glu Ser Gly Pro Gly Leu Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Gln Leu Thr Ile Ser Lys Asn Thr Ser Lys Asn Gln Val
65                  70                  75                  80
```

```
Ser Leu Lys Ile Thr Ser Val Thr Ala Ala Asp Thr Ala Thr Tyr Phe
                85                  90                  95

Cys Ala Arg Lys Lys Tyr Asp Pro Pro Trp Phe Val Asp Trp Gly Gln
            100                 105                 110

Gly Thr Leu Val Thr Val Ser Ser
        115                 120

<210> SEQ ID NO 54
<211> LENGTH: 120
<212> TYPE: PRT
<213> ORGANISM: Artificial
<220> FEATURE:
<223> OTHER INFORMATION: Synthetic

<400> SEQUENCE: 54

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Ala Arg Tyr Asp Pro Pro Trp Phe Val Asp Trp Gly Gln
            100                 105                 110

Gly Thr Leu Val Thr Val Ser Ser
        115                 120

<210> SEQ ID NO 55
<211> LENGTH: 120
<212> TYPE: PRT
<213> ORGANISM: Artificial
<220> FEATURE:
<223> OTHER INFORMATION: Synthetic

<400> SEQUENCE: 55

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Val Arg Tyr Asp Pro Pro Trp Phe Val Asp Trp Gly Gln
            100                 105                 110

Gly Thr Leu Val Thr Val Ser Ser
        115                 120
```

```
<210> SEQ ID NO 56
<211> LENGTH: 120
<212> TYPE: PRT
<213> ORGANISM: Artificial
<220> FEATURE:
<223> OTHER INFORMATION: Synthetic

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Phe Arg Tyr Asp Pro Pro Trp Phe Val Asp Trp Gly Gln
            100                 105                 110

Gly Thr Leu Val Thr Val Ser Ser
            115                 120

<210> SEQ ID NO 57
<211> LENGTH: 120
<212> TYPE: PRT
<213> ORGANISM: Artificial
<220> FEATURE:
<223> OTHER INFORMATION: Synthetic

<400> SEQUENCE: 57

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
    50                  55                  60

Leu Lys Ser Arg Leu Thr Ile Ser Lys Asn Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Lys Lys Tyr Asp Pro Pro Trp Phe Val Asp Trp Gly Gln
            100                 105                 110

Gly Thr Leu Val Thr Val Ser Ser
            115                 120
```